(12) United States Patent
Honjo et al.

(10) Patent No.: US 7,083,966 B2
(45) Date of Patent: Aug. 1, 2006

(54) CYTIDINE DEAMINASE

(75) Inventors: Tasuku Honjo, Kyoto (JP); Masamichi Muramatsu, Kyoto (JP)

(73) Assignee: Kyoto University, Kyoto (JP)

( * ) Notice: Subject to any disclaimer, the term of this patent is extended or adjusted under 35 U.S.C. 154(b) by 44 days.

(21) Appl. No.: 10/884,878

(22) Filed: Jul. 2, 2004

(65) Prior Publication Data

US 2005/0054073 A1 Mar. 10, 2005

Related U.S. Application Data

(60) Division of application No. 09/966,880, filed on Sep. 28, 2001, now Pat. No. 6,815,194, which is a continuation-in-part of application No. PCT/JP00/01918, filed on Mar. 28, 2000.

(30) Foreign Application Priority Data

Mar. 29, 1999 (JP) .................................. 11/87192
Jun. 24, 1999 (JP) ................................. 11/178999
Dec. 27, 1999 (JP) ................................. 11/371382

(51) Int. Cl.
  C12N 9/78 (2006.01)
  C12Q 1/68 (2006.01)
  C12P 21/06 (2006.01)
  C07H 21/04 (2006.01)
  A23J 1/00 (2006.01)

(52) U.S. Cl. .......................... 435/227; 435/6; 435/69.1; 536/23.2; 530/412

(58) Field of Classification Search ..................... None
See application file for complete search history.

(56) References Cited

OTHER PUBLICATIONS

Whisstock et al, Prediction of protein function from protein sequence and structure. Q Rev Biophys. Aug. 2003;36(3):307-40. Review.*
Galye et al, Identification of regions in interleukin-1 alpha important for activity. J Biol Chem. Oct. 15, 1993;268(29):22105-11.*
A_Geneseq_Dec. 16, 2004 Database Accession No. AAW30763 May 7, 1998 Agen, Inc. from JP09266792 PD Oct. 14, 1997.*
Anant et al. "apobec-1, the Catalytic Subunit of the Mammalian Apolipoprotein B mRNA Editing Enzyme, Is a Novel RNA-binding Protein" *J. Biol. Chem.* 270(24);14762-14767 (1995).
Adams et al. "CIT-HSP-2326M11.TR CIT-HSP Homo sapiens genomic clone 2326M11, DNA sequence" *EMBL*Acc#AQ42682 alingment with SEQ ID No. 9 (1998).
Adams et al. EST04465 Fetal brain, Stratagene (cat#936206) Homo sapiens cDNA clone HFBDV37. *EMBL*Acc# T06576 or HS5762 alignment with SEQ ID No. 9 (1993).
Ausubel "Protein Expression In; Current Protocols in Molecular Biology" *Chapter 16* (1987).
Database EMBL [online] Accession No. AAK81088 (2001).
Database EMBL [online] Accession No. AAK81089 (2001).
Demontis et al. "Isolation and Characterization of the Gene Coding for Human Cytidine Deaminase" *Biochimica Et Biophysica Acta.* 1443: 323-333 (1998).
GenBank Accession No. AA178778 (1997).
International Preliminary Search Report *PCT* (2000).
Muramatsu et al. "Class Switch Recombination and Hypermutation Require Activation-Induced Cytidine Deaminase (AID), a Potential RNA Editing Enzyme" *Cell* 102(5):553-563 (2000).
Muramatsu et al. "Specific Expression of Activation-induced Cytidine Deaminase (AID), a Novel Member of the RNA-editing Deaminase Family in Germinal Center B Cells" *J. of Bio. Chem.* 274(26):18470-18476 (1999).
Revy et al. "Activation-Induced Cytidine Deaminase (AID) Deficiency Causes the Autosomal Recessive Form of the Hyper-IgM Syndrome (HIGM2)" *Cell* 102(5):565-575 (2000).
Strausberg (AA954956) GenBank. Alignment with SEQ ID No. 7 (1998).
Strausberg (AI016902) GenBank. Alignment with SEQ ID No. 7 (1999).
Strausberg (AW135547) GenBank. Alignment with SEQ ID No. 7 (1999).
Vincenzetti et al. "Recombinant Human Cytidine Deaminase: Expression, Purification, and Characterization" *Protein Expression and Purification* 8: 247-253 (1996).
Liao et al., "APOBEC-2, a Cardiac- and Skeletal Muscle-Specific Member of the Cytidine Deaminase Supergene Family," *Biochem. Biophys. Res. Commun.*, 260(2):398-404 (1999).

* cited by examiner

*Primary Examiner*—Sheridan Swope
(74) *Attorney, Agent, or Firm*—Fish & Richardson P.C.

(57) ABSTRACT

Genes encoding novel proteins named AID (Activation-Induced cytidine Deaminase) are described. The AID proteins are structurally related to APOBEC-1, an RNA editing enzyme, and have a cytidine deaminase activity similar to APOBEC-1. The AID genes were found by preparing cDNA libraries from mouse B cell clone CH12F3-2 (which undergoes class switch recombination from IgM to IgA at an extremely high rate after activation of the cells by stimulation with cytokines), with and without stimulation with cytokines, and performing subtraction cloning using the libranes.

7 Claims, 17 Drawing Sheets

| | | |
|---|---|---|
| mAID | 1 | M--D--SL-L-MK-QKKF-LYHFKN-RW-AKG-RETYLCVVKRRDSATSCSLDFGHLR 50 |
| mAPOBEC-1 | 1 | MSSETGPVAVDPTLRRRIEPHEF-EVFDPRELRKETCLLYEIN-W-GGRH-SV-WRITS 55 |
| mAID | 51 | NKSGCHVELLFL-RYISDWDLDP-GRCYRVTWFTSWSPCYDCARHVAEFLRWNPNLSLRI 108 |
| mAPOBEC-1 | 56 | QNTSNHVEVNFLEKFTTERYFRPNTRG-SITWFLSWSPCGECSRAITEFLSRHPYVTLFI 114 |
| mAID | 109 | FTARLYFCEDRKAEPEGLRRLHRAGVQIGIMTFKDYFYCWNTFVENRERTFKAW**EGLHEN 168 |
| mAPOBEC-1 | 115 | YIARLYLLHHTDQR-NRQGLRDLISSGVTLQIMTEQEYCYCWRNFVNYPPSNEAYWPRYPHL 173 |
| mAID | 169 | SVRL-TRQLRRILLPLYE-VDDLRDAFRMLGF----------------- 198 |
| mAPOBEC-1 | 174 | WVKLYVLELYCIILGLPPCLKILRRKQPQLTFFTITLQTCHYQRIPPHLLWATGLK 229 |

FIG. 5

Day 0

Sense probe

AS probe

PNA receptor

Day 5

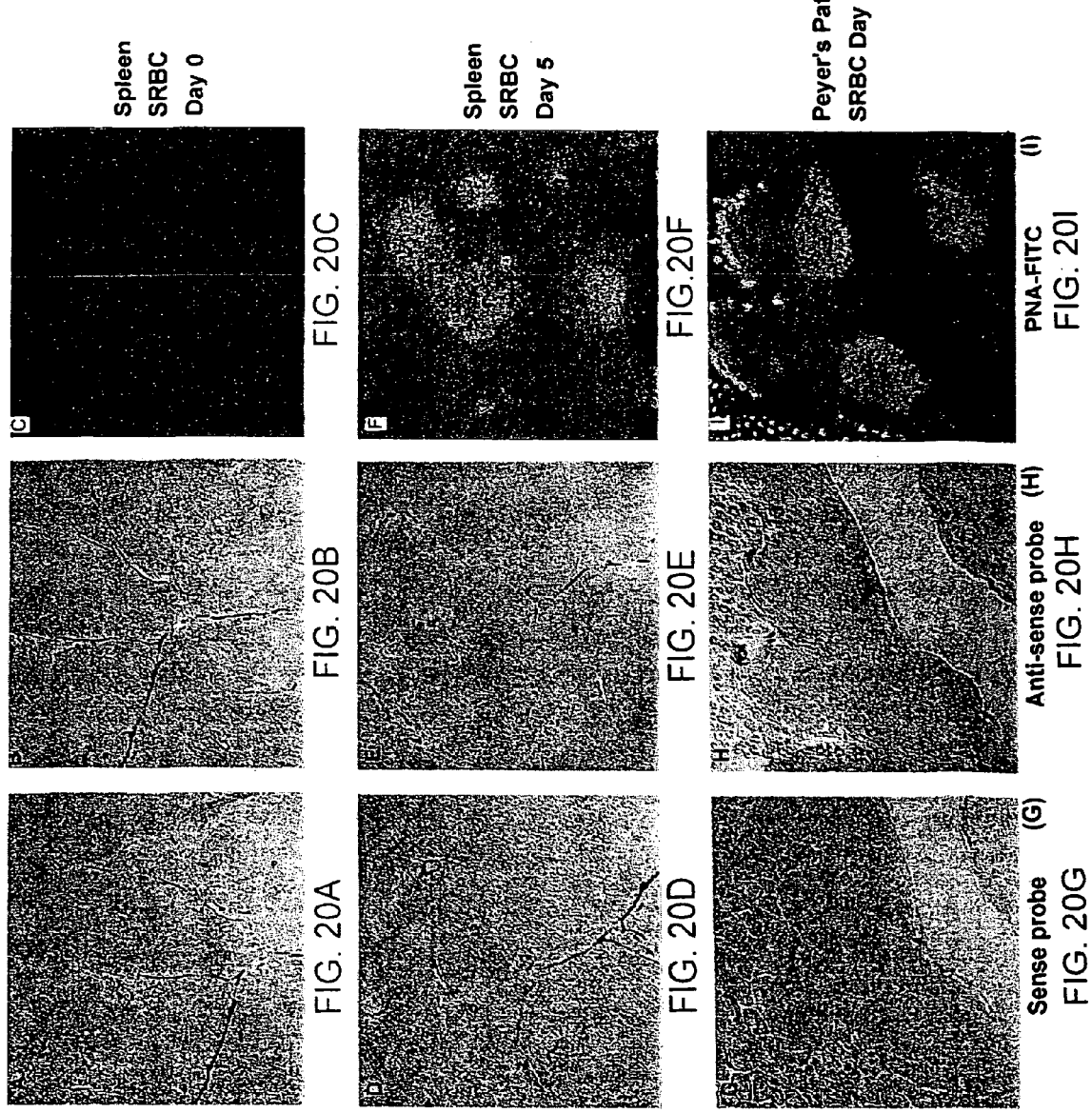

Human :   1 MDSLLMNRRKFLYQFKNVRWAKGRRETYLCYVVKRRDSATSFSLDFGYLRNKNGCHVELL  60
             ***++ ****** ************** *++|****
Mouse :   1 MDSLLMKQRKFLYHFKNVRWAKGRHETYLCYVVKRRDSATSCSLDFGHLRNKSGCHVELL  60

Human :  61 FLRYISDWDLDPGRCYRVTWFTSWSPCYDCAREV ADFLRGNPNLSLRIFTARLYFCEDRK 120
            **********************************|*+* *****************
Mouse :  61 FLRYISDWDLDPGRCYRVTWFTSWSPCYDCAREV AEFLRWNPNLSLRIFTARLYFCEDRK 120

Human : 121 AEPEGLRRLHRAGVQIAIMTFKDYFYCWNTFVENHERTFKAWEGLHENSVRLSRQLRRIL 180
            *************  ********* ***********+*****
Mouse : 121 AEPEGLRRLHRAGVQIGIMTFKDYFYCWNTFVENRERTFKAWEGLHENSVRLTRQLRRIL 180

Human : 181 LPLYEVDDLRDAFRTLGL  198
            ************ 
Mouse : 181 LPLYEVDDLRDAFRMLGF  198

FIG. 22

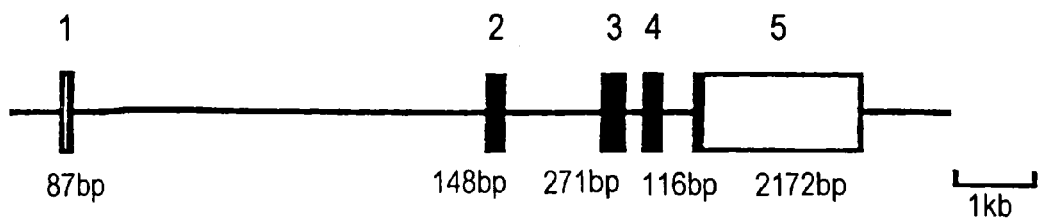

| Exons | 5' Splice Donor | 3' Splice Acceptor | Exons |
|---|---|---|---|
| 1 | GACAGgt | agCCTCT | 2 |
| 2 | ATAAGgt | agAACGG | 3 |
| 3 | CAAAGgt | agATTAT | 4 |
| 4 | TTTTGgt | agCCCCT | 5 |

FIG. 23

CYTIDINE DEAMINASE

CLAIM OF PRIORITY

This application is a divisional of U.S. patent application Ser. No. 09/966,880, filed on Sep. 28, 2001, and issued as U.S. Pat. No. 6,815,194 on Nov. 9, 2004, which is a continuation-in-part of PCT/JP00/01918, filed Mar. 28, 2000, and published as WO/200058480 on Oct. 5, 2000, which claims priority from Japanese Patent Application No. 11-87192, filed Mar. 29, 1999; Japanese Patent Application No. 11-178999, filed Jun. 24, 1999; and Japanese Patent Application No. 11-371382, filed Dec. 27, 1999. The disclosures of the prior applications are hereby incorporated by reference.

FIELD OF INVENTION

The present invention relates to novel proteins having a cytidine deaminase activity; DNAs and fragments thereof (cDNAs, genomic DNAs, and primer DNAs) encoding the proteins; expression vectors comprising the DNAs; transformants transformed with the expression vectors; antibodies reactive to the proteins or fragments thereof; cells producing the antibodies; and methods for identifying substances that regulate production of the proteins, transcription of genes encoding the proteins into mRNAs, or enzyme activities of the proteins.

BACKGROUND

The germinal center of mammals comprises a highly specialized microenvironment required for the final process of maturation towards antigen specific memory cells and long-lived plasma cells (Embo J., 16:2996–3006, 199; Semin. Immunol., 4:11–17, 1992). In this microenvironment, two fundamental editings of the immunoglobulin genes take place (J. Exp. Med., 173:1165–1175, 1991; Embo. J., 12:4955–4967, 1993; Adv. Exp. Med. Biol., 186:145–151, 1985; Nature, 342:929–931, 1989; Cell, 67:1121–1129).

The first fundamental editing is somatic hypermutation (Curr. Opin. Immunol., 7:248–254, 1995; Annu. Rev. Immunol., 14:441–457, 1996; Science, 244:1152–1157, 1989), a phenomenon in which extensive point mutation in the exons of genes encoding variable regions of immunoglobulins occurs. Accumulation of point mutations leads to selection of B cells expressing high affinity immunoglobulins on their cell surface, accompanied by the affinity maturation of antibodies (Embo. J., 4:345–350, 1985; Proc. Natl. Acad. Sci. USA, 85:8206–8210, 1988). As a result, immunoglobulin genes are edited as new functional genes.

Another fundamental editing process is the class switch recombination (CSR). In CSR, effector functions of antibodies, such as complement fixation, are selected by exchanging exons encoding constant regions of immunoglobulin heavy chains (Curr. Top. Microbiol. Immunol., 217:151–169, 1996; Annu. Rev. Immunol., 8:717–735, 1990).

These two types of genetic editing are very important for effective humoral immunoreaction to eliminate harmful microbes. The molecular mechanisms of the genetic phenomena have not yet been elucidated despite extensive study for several decades.

The present inventors isolated a mouse B cell clone, CH12F3-2, as a research tool to elucidate the molecular mechanism of class switch recombination of immunoglobulin. In this B cell line, class switch recombination (CSR) from IgM to IgA begins several hours after stimulation with IL-4, TGF-β, and CD40L; ultimately, over 80% of the cells become IgA positive (Immunity, 9:1–10, 1998; Curr. Biol., 8:227–230, 1998; Int. Immunol., 8:193–201, 1996).

Using the mouse B cell clone CH12F3-2, the present inventors previously reported that the breakpoints of CSR distribute not only in the switch region (or "S region"), characterized by repeated sequences, but also in neighboring sequences (Curr. Biol., 8:227–230, 1998). However, the breakpoints were rarely seen in I exon and C exon, which are located upstream and downstream of the S region, respectively. Also, according to accumulated scientific evidence, it has been shown that transcription of I exon and C exon and splicing of the transcripts are essential for CSR (Cell, 73:1155–1164, 1993; Science, 259:984–987, 1993; Proc. Natl. Acad. Sci, USA, 90:3705–3709, 1993; Cell, 81:833–836, 1995).

This suggests that the transcripts are involved in CSR either directly or indirectly. Accordingly, the present inventors propose a theory that class switch is initiated by the recognition of DNA-RNA complex structure and not by the recognition of nucleotide sequences of the switch region. This idea is further fortified by the fact that even when the Sa region is substituted with an Sα region or an Sγ region by introducing a mini-chromosome into the above-mentioned mouse B cell clone CH12F3-2, CSR in the mini-chromosome efficiently occurs after stimulation with cytokines (Immunity, 9:1–10, 1998).

In plants and protozoa, RNA editing, another type of genetic editing, is widely used as a mean for producing functional genes from a limited genome (Cell, 81:833–836, 1995; Cell, 81:837–840, 1995). mRNA editing of many molecules such as the mRNA for apolipoprotein B (apoB), AMPA receptors, Wilmstumor-1, α-galactosidase and neurofibromatosis type-1, and tRNA-Asp, have been reported (Trends Genet., 12:418–424, 1996; Curr. Opin. Genet. Dev., 6:221–231, 1996). Although the molecular mechanism of mammalian RNA editing has not yet been elucidated, one performed by APOBEC-1 (apolipoprotein B mRNA editing enzyme, catalytic polypeptide-1) is becoming understood by degrees (Science, 260:1816–1819, 1993; J. Biol. Chem., 268:20709–20712, 1993).

In apoB RNA editing, the first base C (cytosine) of codon CAA, which encodes glutamine, is converted to U (uridine), which alters the codon to UAA. As a result, an in-frame stop codon is made in the apoB mRNA (J. Cell., 81:187–195, 1995; J. Cell., 50:831–840, 1987; Science, 238:363–266, 1987). apoB-48 and apoB-100 are transcripts of edited mRNA and unedited mRNA of apoB, respectively, and these proteins possess totally different physiological functions from each other (J. Biol. Chem., 271:2353–2356, 1996).

In site-specific RNA-editing, auxiliary factors are required (Science, 260:1816–1819, 1993; J. Biol. Chem., 268:20709–20712, 1993). In the absence of auxiliary factors, APOBEC-1 shows only a cytidine deaminase activity, possessing non-specific low affinity to RNA (J. Biol. Chem., 268:20709–20712, 1993; J. Cell., 81:187–195, 1995; J. Biol. Chem., 270:14768–14775, 1995; J. Biol. Chem., 270:14762–14767, 1995). The expression and activity of the auxiliary factors are found not only in organs with apoB mRNA editing, but also in organs with undetectable levels of APOBEC-1 expression, or organs without apoB mRNA editing (Science, 260:1816–1819, 1993; J. Biol. Chem., 268:20709–20712, 1993; Nucleic Acids Res., 22:1874–1879, 1994; Proc Natl. Acad. Sci, USA, 91:8522–8526, 1994; J. Biol. Chem., 269:21725–21734, 1994).

The unexpected expression of the auxiliary factors involved in apoB mRNA editing suggests that the auxiliary factors may be involved in more general cellular functions or other yet unknown RNA editing. Since the possibility exists that CSR and hypermutation, which are involved in genetic editing of immunoglobulin genes, may be accomplished by RNA editing, it would be very interesting to elucidate whether RNA editing takes place or not in the genetic editing of immunoglobulin genes as mentioned above.

SUMMARY

The present invention provides AID (Activation-Induced cytidine Deaminase), a novel cytidine deaminase that is structurally related to APOBEC-1, an RNA editing enzyme, and is involved in RNA editing in germinal center B cells, where genetic editing of immunoglobulin genes occur, and DNA encoding the new enzyme.

The present inventors intensively searched for novel genes involved in class switch recombination (CSR), one of the major types of genetic editing of immunoglobulin genes. As a result, by preparing cDNA libraries for the mouse B cell clone CH12F3-2 (in which class switch recombination from IgM to IgA is shown to occur at an extremely high rate upon activation of the cells by stimulation with cytokines), with and without stimulation with cytokines, and performing subtraction cloning using the libraries, the present inventors found genes encoding mouse- and human-derived novel proteins named AID (Activation-Induced cytidine Deaminase), having a structural relationship to APOBEC-1, one of the RNA editing enzymes, and having a cytidine deaminase activity similar to APOBEC-1.

The AID protein in the present invention possesses features described below, and is considered to be a very important RNA-modifying deaminase involved in regulating B cell activation, CSR of immunoglobulin genes, somatic hypermutation, and affinity maturation, which are all involved in genetic editing specific to germinal center function:

(1) The ORF of the cDNA encoding the AID protein comprises 198 amino acids, with a 24 kDa calculated molecular weight (mouse: SEQ ID NO:2, and human: SEQ ID NO:8). The mouse AID protein shows an approximately 28 kDa molecular weight by SDS-PAGE.

(2) The amino acid sequence of the AID protein is 34% and 26% identical to APOBEC-1 (apolipoprotein B mRNA editing enzyme, catalytic polypeptide-1) at the amino acid sequence level, for mouse and human derived proteins, respectively.

(3) The AID protein has a cytidine/deoxycytidine deaminase motif, which is the active center of the deaminase activity and is conserved in amino acid sequences of proteins belonging to the cytosine nucleoside/nucleotide deaminase family.

(4) The cytidine deaminase motif of the AID protein is allied with an RNA editing deaminase subgroup.

(5) The AID protein has a leucine-rich region considered to be important in protein-protein interaction, similar to APOBEC-1. Four leucines in this leucine-rich region of the AID protein are conserved in the leucine-rich region of APOBEC-1 in rabbit, rat, mouse and human.

(6) In the primary structure of the AID protein, all of the amino acid residues reported to be necessary for APOBEC-1 to bind RNA (Phe66, Phe87, His61, Glu63 and Cys93) are conserved.

(7) The AID protein has a pseudoactive site domain in its C terminal for forming homodimers, similar to APOBEC-1 and ECDDA, an *E. coli* derived cytidine deaminase. There is a possibility that the AID protein forms homodimers, or associates with other auxiliary proteins.

(8) The AID protein shows a concentration-dependent cytidine deaminase activity. The activity can be inhibited dose dependently by tetrahydrouridine (THU), a specific inhibitor of cytidine deaminase. Also, a zinc chelator, 1,10-o-phenanthroline, inhibits the cytidine deaminase activity of the AID protein while 1,7-o-phenanthroline, the inactive isomer, shows a weak inhibition. Thus, the AID protein can considered to be a zinc-dependent cytidine deaminase, as is APOBEC-1.

(9) Strong expression of AID mRNA is seen in lymph nodes (mesenteric and amygdaline). Also, weak expression in spleen is seen.

(10) Expression of AID mRNA is seen in a variety of lymphoid tissues (Peyer's patches, mesenteric lymph node, axillary lymph node, spleen, and bone marrow). Especially notable expression is seen in peripheral lymphoid organs, such as lymphatic nodes and Peyer's patches. In contrast, expression in primary lymphoid organs is lower than the peripheral lymphoid organs.

(11) Expression of AID mRNA is at the lower limit of detection without cytokine (IL-4, CD40L, TGF-$\beta$) stimulation in mouse B cell clone CH12F3-2, in which the cytokines stimulate class switch from IgM to IgA in the cells. Expression is induced 3 hours after stimulation, and maximal expression is seen after 12 hours, with cytokine stimulation.

(12) AID mRNA expression in mouse B cell clone CH12F3-2 can be induced more strongly when stimulated with all three cytokines, IL-4, CD40L and TGF-$\beta$, simultaneously, than with any one of them alone. Also, it can be considered that de novo protein synthesis is necessary for augmentation of AID mRNA expression, as the AID mRNA expression induction by cytokines in mouse B cell clone CH12F3-2 can be inhibited by cycloheximide, a protein synthesis inhibitor.

(13) In in vitro tests, an augmentation of AID mRNA expression can be seen when normal mouse spleen B cells are stimulated with LPS alone, LPS+IL-4, or LPS+TGF-$\beta$.

(14) In in vivo tests, when normal mice are immunized with sheep red blood cells (SRBC), a significant augmentation of AID mRNA expression can be seen 5 days after immunization, in which SRBC are known to induce clonal expansion, germinal center formation, and class switch recombination and affinity maturation of immunoglobulin genes.

(15) The in vivo augmentation of AID mRNA expression by SRBC immunization is specifically seen in splenic CD19 positive B cells.

(16) AID mRNA expression in lymphoid organs is specifically seen in the germinal center, enriched with B cells activated by antigen stimulation.

(17) The human AID gene is located at locus 12p13, close to locus 12p13.1, where the APOBEC-1 gene is located.

According to the characteristics described above, the AID protein of the present invention can be considered to have a function of regulating various biological mechanisms required for generation of antigen-specific immunoglobulins (specific antibodies), which eliminate non-self antigens (foreign antigen, self-reacting cells, etc.) that trigger various diseases. The mechanism for generation of immunoglobulin having high specificity to antigens includes germinal center functions such as activation of B cells, class switch recombination of immunoglobulin genes, somatic hypermutation, and affinity maturation. The AID protein of the present invention can be considered to be one of the enzymes that play an important role in the genetic editing occurring in germinal center B cells (e.g. class switch recombination and somatic mutation).

The dysfunction of the AID protein of the present invention can be the cause of humoral immunodeficiency since it induces failure of germinal center B cell function, such as antigen-specific B cell activation, class switch recombination, and somatic mutation. Conversely, the hyperfunction of the AID protein may induce allergy disease or autoimmune disease since it can cause inappropriate B cell activation and needless class switch recombination and somatic mutation.

Therefore, regulation of the function of AID protein and the gene encoding it enables prevention and treatment of various immunodeficiencies, autoimmune diseases, and allergies, which result from, for example, B cell dysfunctions (e.g., IgA deficiency, IgA nephropathy, γ globulinemia, hyper IgM syndrome, etc.) or class switch deficiency of immunoglobulin. Thus, the AID protein and the gene encoding the AID protein can be targets for the development of drugs for therapy of diseases mentioned above.

Examples of diseases whose onset prevention, symptom remission, therapy and/or symptomatic treatment effect is expected by regulating the function of the AID protein of the present invention or the gene encoding it include, for example, primary immunodeficiency syndrome with congenital disorder of immune system, mainly various immunodeficiencies considered to develop by B cell deficiency, decrease, or dysfunction (e.g., sex-linked agammaglobulinemia, sex-linked agammaglobulinemia with growth hormone deficiency, immunoglobulin deficiency with high IgM level, selective IgM deficiency, selective IgE deficiency, immunoglobulin heavy chain gene deletion, K chain deficiency, IgA deficiency, IgG subclass selective deficiency, CVID (common variable immunodeficiency), infantile transient dysgammaglobulinemia, Rosen syndrome, severe combined immunodeficiency (sex-linked, autosomal recessive), ADA (adeno sine deaminase) deficiency, PNP (purine nucleoside phosphorylase) deficiency, MHC class II deficiency, reticular dysplasia, Wiskott-Aldrich syndrome, ataxia telangiectasia, DiGeorge syndrome, chromosomal aberration, familial Ig hypermetabolism, hyper IgE syndrome, Gitlin syndrome, Nezelof syndrome, Good syndrome, osteodystrophy, transcobalamin syndrome, secretory bead syndrome, etc.), various diseases with antibody production deficiency that are secondary immunodeficiency syndromes with a disorder of immune system caused by an acquired etiology (for example, AIDS, etc.), and/or various allergic diseases (e.g., bronchial asthma, atopic dermatitis, conjunctivitis, allergic rhinitis, allergic enteritis, drug-induced allergy, food allergy, allergic urticaria, glomerulonephritis, etc.).

The AID proteins of the present invention, a fragment thereof, a DNA encoding the AID protein, a fragment thereof, and an antibody against the AID protein are useful as reagents for developing drugs for prevention and therapy of such diseases.

Also, the DNA itself is useful as an antisense drug regulating the function of the AID gene at a gene level and in gene therapy. The protein or the fragments thereof (e.g. enzyme active site) themselves are useful as drugs.

Furthermore, a DNA comprising a nucleotide sequence that is complementary to an arbitrary partial nucleotide sequence in the nucleotide sequence of genomic DNA encoding AID protein of the present invention (especially human AID protein) is useful as a primer DNA for polymerase chain reaction (PCR).

An arbitrary partial nucleotide sequence of genomic DNA encoding the AID protein (especially human AID protein) of the present invention can be amplified by PCR using the primer DNA pair. For example, in the case that mutation or deletion of the nucleotide sequence of genomic DNA (especially exon) encoding AID protein is presumed to cause a certain immunodeficiency or an allergy, mutations and deletions in the genomic DNA can be identified by amplifying an arbitrary partial nucleotide sequence of genomic DNA encoding the AID protein obtained from tissue or cells of immunodeficiency or allergy patients by PCR using a pair of primer DNAs, by analyzing the presence and the size of PCR products and the nucleotide sequence of the PCR products, and by comparing the nucleotide sequence with the corresponding nucleotide sequence in the genomic DNA encoding the AID protein derived from a normal human. That is to say, this method is capable of not only, for example, elucidating relationships between immunodeficiency or allergy and AID protein, but also, in the case where the AID protein is the cause of onset of a sort of disease (e.g. immunodeficiency and/or allergy), diagnosing the disease by the methods mentioned above.

Furthermore, an antibody reactive to the AID protein of the present invention or a fragment thereof is extremely useful as an antibody drug by regulating functions of the AID protein.

Furthermore, the gene (DNA), protein, and antibody of the present invention are useful as reagents for searching for substrates (e.g. RNA, etc.) that interact (binding) with the protein (enzyme) of the present invention, or other auxiliary proteins associated with the protein of the present invention, and for developing drugs targeting the substrates and auxiliary proteins.

Also, model animals can be generated by disrupting (inactivating) the AID gene based on the genetic information on the AID protein derived from mammals (e.g. mouse, etc.), which is one embodiment of the DNA of present invention. By analyzing the physical, biological, pathological, and genetic features of the model animal, it is possible to elucidate functions of the genes and the proteins of the present invention.

Furthermore, by introducing a normal human AID gene or mutant human AID gene (e.g. mutant human AID genes derived from immunodeficiency patients), which is one embodiment of the present invention, into the model animal whose endogenous gene has been disrupted, model animals having only normal or mutant human AID genes of the present invention can be generated. By administering drugs (compounds, antibodies, etc.) targeting the introduced human AID genes to the model animals, therapeutic effects of the drugs can be evaluated.

Furthermore, a method for identifying a substance that regulates production of the AID protein of the present invention or transcription of a gene encoding the AID protein into mRNA, or a substrate that inhibits the enzyme activity of the AID protein (e.g. cytidine deaminase activity) is extremely useful as a means to develop drugs for therapy and prevention of various diseases (especially, immunodeficiency and/or allergy) in which the above-mentioned AID protein or AID gene is considered to be involved.

Thus, the present invention, for the first time, provides the below-mentioned DNAs (cDNAs, genomic DNAs, and an arbitrary fragment thereof), proteins, expression vectors, transformants, antibody pharmaceutical compositions, cells, the use of the DNA fragments as primer DNAs, and methods for screening.

(1) A DNA or a fragment thereof encoding a protein comprising the amino acid sequence of SEQ ID NO:2 or 8.

(2) The DNA or the fragment of (1), wherein the protein has a cytidine deaminase activity.

(3) A DNA or a fragment thereof comprising the nucleotide sequence of SEQ ID NO:1 or 7.

(4) A DNA or a fragment thereof comprising a nucleotide sequence of (a) or (b) below:
  (a) a nucleotide sequence comprising the nucleotide residues 93 to 689 of SEQ ID NO:1 or
  (b) a nucleotide sequence comprising the nucleotide residues 80 to 676 of SEQ ID NO:7.

(5) A DNA or a fragment thereof of (a) or (b) below:
  (a) a DNA or a fragment thereof that hybridizes under stringent conditions with a DNA comprising the nucleotide sequence of SEQ ID NO:1 and that encodes a mammal-derived protein being homologous to a protein that comprises the amino acid sequence of SEQ ID NO:2 and having a cytidine deaminase activity or
  (b) a DNA or a fragment thereof that hybridizes under stringent conditions with a DNA comprising the nucleotide sequence of SEQ ID NO:7 and that encodes a mammal-derived protein being homologous to a protein that comprises the amino acid sequence of SEQ ID NO:8 and having a cytidine deaminase activity.

(6) A protein or a fragment thereof comprising the amino acid sequence of SEQ ID NO:2 or 8.

(7) A protein or a fragment thereof comprising substantially the same amino acid sequence as that of SEQ ID NO:2 or 8 and having a cytidine deaminase activity.

(8) A protein of (a) or (b) below.
  (a) a mammal-derived protein that comprises an amino acid sequence encoded by a DNA hybridizing under stringent conditions with a DNA comprising the nucleotide sequence of SEQ ID NO:1, that is homologous to a protein comprising the amino acid sequence of SEQ ID NO:2, and that has a cytidine deaminase activity, or
  (b) a mammal-derived protein that comprises an amino acid sequence encoded by a DNA hybridizing under stringent conditions with a DNA comprising the nucleotide sequence of SEQ ID NO:7, that is homologous to a protein comprising the amino acid sequence of SEQ ID NO:8, and that has a cytidine deaminase activity.

(9) An expression vector comprising the DNA or the fragment of any one of (1) to (5).

(10) A transformant transformed with the expression vector of (9).

(11) An antibody or a portion thereof reactive to the protein of any one of (6) to (8) or to a fragment of the protein.

(12) The antibody or the portion thereof of (11), wherein the antibody is a monoclonal antibody.

(13) A pharmaceutical composition comprising the antibody or the portion thereof of (11) or (12), and a pharmaceutically acceptable carrier.

(14) A cell producing a monoclonal antibody reactive to the protein of any one of (6) to (8) or to a fragment of the protein.

(15) The cell of (14), wherein the cell is a hybridoma obtained by fusing, with a mammal-derived myeloma cell, a non-human mammal-derived B cell that produces a monoclonal antibody.

(16) The cell of (15), wherein the cell is a transgenic cell transformed by introducing, into a cell, either or both of a DNA encoding a heavy chain of the monoclonal antibody and a DNA encoding a light chain of the monoclonal antibody.

(17) A genomic DNA or a fragment thereof comprising a nucleotide sequence of any one of (a) to (c) below:
  (a) SEQ ID NO:9,
  (b) SEQ ID NO:10, or
  (c) SEQ ID NO:35.

(18) A genomic DNA or a fragment thereof comprising a nucleotide sequence of any one of (a) to (e) below:
  (a) SEQ ID NO:11,
  (b) SEQ ID NO:12,
  (c) SEQ ID NO:13,
  (d) SEQ ID NO:14, or
  (e) SEQ ID NO:15.

(19) A DNA comprising a nucleotide sequence complementary to an arbitrary partial nucleotide sequence of a nucleotide sequence of any one of (a) to (h) below:
  (a) SEQ ID NO:9,
  (b) SEQ ID NO:10,
  (c) SEQ ID NO:11,
  (d) SEQ ID NO:12,
  (e) SEQ ID NO:13,
  (f) SEQ ID NO:14,
  (g) SEQ ID NO:15, or
  (h) SEQ ID NO:25.

(20) The DNA of (19), wherein the DNA comprises a nucleotide sequence of any one of (a) to (q) below:
  (a) SEQ ID NO:18,
  (b) SEQ ID NO:19,
  (c) SEQ ID NO:20,
  (d) SEQ ID NO:21,
  (e) SEQ ID NO:22,
  (f) SEQ ID NO:23,
  (g) SEQ ID NO:24,
  (h) SEQ ID NO:25,
  (i) SEQ ID NO:26,
  (j) SEQ ID NO:27,
  (k) SEQ ID NO:28,
  (l) SEQ ID NO:29,
  (m) SEQ ID NO:30,
  (n) SEQ ID NO:31,
  (O) SEQ ID NO:32,
  (p) SEQ ID NO:33, or
  (q) SEQ ID NO:34.

(21) Use of the DNA of (19) or (20) as a primer DNA in polymerase chain reaction.

(22) Use of a pair of DNAs of any one of (a) to (n) below as primer DNAs in polymerase chain reaction:
  (a) a DNA comprising the nucleotide sequence of SEQ ID NO:31 and a DNA comprising the nucleotide sequence of SEQ ID NO:32,
  (b) a DNA comprising the nucleotide sequence of SEQ ID NO:20 and a DNA comprising the nucleotide sequence of SEQ ID NO:22, (c) a DNA comprising the nucleotide sequence of SEQ ID NO:21 and a DNA comprising the nucleotide sequence of SEQ ID NO:30,
(d) a DNA comprising the nucleotide sequence of SEQ ID NO:24 and a DNA comprising the nucleotide sequence of SEQ ID NO:25,
(e) a DNA comprising the nucleotide sequence of SEQ ID NO:23 and a DNA comprising the nucleotide sequence of SEQ ID NO:27,
(f) a DNA comprising the nucleotide sequence of SEQ ID NO:23 and a DNA comprising the nucleotide sequence of SEQ ID NO:28,
(g) a DNA comprising the nucleotide sequence of SEQ ID NO:23 and a DNA comprising the nucleotide sequence of SEQ ID NO:29,
(h) a DNA comprising the nucleotide sequence of SEQ ID NO:26 and a DNA comprising the nucleotide sequence of SEQ ID NO:27,
(i) a DNA comprising the nucleotide sequence of SEQ ID NO:26 and a DNA comprising the nucleotide sequence of SEQ ID NO:28,
(j) a DNA comprising the nucleotide sequence of SEQ ID NO:26 and a DNA comprising the nucleotide sequence of SEQ ID NO:29,
(k) a DNA comprising the nucleotide sequence of SEQ ID NO:34 and a DNA comprising the nucleotide sequence of SEQ ID NO:28,
(l) a DNA comprising the nucleotide sequence of SEQ ID NO:34 and a DNA comprising the nucleotide sequence of SEQ ID NO:29,
(m) a DNA comprising the nucleotide sequence of SEQ ID NO:33 and a DNA comprising the nucleotide sequence of SEQ ID NO:29, or,
(n) a DNA comprising the nucleotide sequence of SEQ ID NO:18 and a DNA comprising the nucleotide sequence of SEQ ID NO:19.

(23) A method for identifying a substance that regulates transcription of a gene encoding an AID protein comprising the amino acid sequence of SEQ ID NO:2 or 8 into mRNA, or production of the AID protein, the method comprising the steps of:
(a) culturing, separately in the presence and the absence of the substance, cells producing the AID protein and
(b) (i) comparing the level of the AID protein produced by the cells cultured in the presence of the substance with the level of the AID protein produced by the cells cultured in the absence of the substance or
(ii) comparing the level of the AID protein-encoding mRNA transcribed in the cells cultured in the presence of the substance with the level of the AID protein-encoding mRNA transcribed in the cells cultured in the absence or the substance.

(24) A method for identifying a substance that regulates transcription of a gene encoding an AID protein comprising the amino acid sequence of SEQ ID NO:2 or 8 into mRNA, or production of the AID protein, the method comprising the steps of:
(a) culturing, separately in the presence and the absence of the substance, cells producing the AID protein and a protein other than the AID protein, wherein transcription of a gene encoding the other protein into mRNA is dependent in the cells on the degree of a signal of transcription of the gene encoding the AID protein into mRNA and
(b) comparing the level of the other protein produced by the cells cultured in the presence of the substance with the level of the other protein produced by the cells cultured in the absence of the substance.

(25) The method of (23) or (24), wherein the cells are transgenic cells transformed with a gene encoding the protein.
(26) The method of (24), wherein the cells are transgenic cells transformed with a gene encoding the protein and a gene encoding the other protein.
(27) The method of (26), wherein the protein is a reporter protein.
(28) The method of (27), wherein comparison of the level of the other protein is comparison of the level of a signal generated by the reporter protein.
(29) The method of (27) or (28), wherein the reporter protein is luciferase.
(30) A method for identifying a substance that inhibits an enzyme activity of an AID protein comprising the amino acid sequence of SEQ ID NO:2 or 8, the method comprising the step of (a) or (b) below:
(a) culturing, separately in the presence and the absence of the substance, mammal-derived B cells or tissues comprising the B cells, and comparing enzyme activities of the AID protein in the B cells separately cultured or
(b) (i) administering the substance separately to an AID gene knockout mouse whose endogenous AID gene is inactivated so that transcription of the endogenous AID gene into mRNA is inhibited, and to a normal mouse and
(ii) comparing enzyme activities of the AID proteins in the B cells isolated from the respective mice.
(31) The method of (30), wherein the enzyme activity is a cytidine deaminase activity.

Hereafter, the present invention is explained in detail, by clarifying the terms used in the present invention and general methods for producing the proteins, DNAs, antibodies, and cells of the present invention.

The "protein or a fragment thereof" means a protein and a fragment thereof derived from a mammal such as human, bovine, sheep, pig, goat, rabbit, rat, hamster, guinea pig, mouse, and so on, preferably a protein or a fragment thereof derived from human, rabbit, rat, or mouse, and particularly preferably, a protein or a fragment thereof derived from human or mouse.

As a particularly preferred embodiment, it means any protein or a fragment thereof below.
(1) A protein or a fragment thereof comprising the amino acid sequence of SEQ ID NO:2 or 8.
(2) A protein or a fragment thereof comprising substantially the same amino acid sequence as that of SEQ ID NO:2 or 8 and having a cytidine deaminase activity.
(3) A mammal-derived protein that comprises an amino acid sequence encoded by a DNA hybridizing under stringent conditions with a DNA comprising the nucleotide sequence of SEQ ID NO:1, that is homologous to a protein comprising the amino acid sequence of SEQ ID NO:2, and that has a cytidine deaminase activity.
(4) A mammal-derived protein that comprises an amino acid sequence encoded by a DNA hybridizing under stringent conditions with a DNA comprising the nucleotide sequence of SEQ ID NO:7, that is homologous to a protein comprising the amino acid sequence of SEQ ID NO:8, and that has a cytidine deaminase activity.

Here, "having substantially the same amino acid sequence" means that a protein has an amino acid sequence where multiple amino acids, preferably 1 to 10 amino acids, particularly preferably 1 to 5 amino acids, in the amino acid sequence shown in the references are substituted, deleted, and/or modified, and that a protein has an amino acid sequence where multiple amino acids, preferably 1 to 10 amino acids, particularly preferably 1 to 5 amino acids, are added to the amino acid sequence shown in the references.

The protein of the present invention includes monomer molecules, homodimers in which one strand binds to another strand comprising an identical amino acid sequence, heterodimers in which one strand binds to another strand comprising a different amino acid sequence, and oligomers such as trimers or tetramers.

Also, a "fragment of a protein" means an arbitrary partial sequence (fragment) in the amino acid sequence that the above-mentioned AID protein of the present invention comprises. For example, it includes an enzyme active site required for the AID protein to exert an enzyme activity represented by a cytidine deaminase activity, and an interaction site required for the AID protein to bind or associate with substrates (e.g. mRNA, etc.) or various auxiliary proteins.

Alphabetical triplet or single letter codes used to represent amino acids in the present specification or figures mean amino acids as follows:

(Gly/G), glycine; (Ala/A), alanine; (Val/V), valine; (Leu/L), leucine; (Ile/I), isoleucine; (Ser/S), serine; (Thr/T), threonine; (Asp/D), aspartic acid; (Glu/E), glutamic acid; (Asn/N), asparagines; (Gln/Q) glutamine; (Lys/K), lysine; (Arg/R), arginine; (Cys/C), cysteine; (Met/M), methionine; (Phe/F), phenylalanine; (Tyr/Y), tyrosine; (Trp/W), tryptophan; (His/H), histidine; (Pro/P), proline.

The proteins and fragments of the present invention can be produced by properly using, in addition to genetic engineering technique mentioned below, methods well known in the art, such as chemical synthesis, cell culture method, and so on, or their modified methods.

Also, the AID protein of the present invention can be produced as a recombinant fusion protein with another protein (e.g. GST (Glutathione S-transferase), etc.). In this case, the fusion protein is advantageous in that it can be extremely easily purified by affinity chromatography employing adsorbent on which another molecule binding specifically to GST is immobilized. Moreover, since various antibodies reactive to GST are provided, the quantification of the fusion protein can be simply carried out by immunoassay (e.g. ELISA, etc.) using antibodies against GST.

The DNA of the present invention is a DNA encoding a protein of the present invention and a fragment thereof, and it includes any nucleotide sequence encoding the protein of the present invention and includes both genomic DNAs and cDNAs. Also, the DNA includes any DNA composed of any codons as long as the codons encode identical amino acids.

Also, the DNA of the present invention includes a DNA encoding a mammalian AID protein, and, as a preferred embodiment, a DNA encoding a mouse AID protein or a human AID protein can be exemplified.

Examples of specific embodiments are as follows:

(1) A DNA encoding a protein comprising the amino acid sequence of SEQ ID NO:2 or 8.
(2) The DNA of (1), wherein the protein has a cytidine deaminase activity.
(3) A DNA comprising the nucleotide sequences of SEQ ID NO:1 or 7.
(4) A DNA comprising nucleotides s 93 to 689 of SEQ ID NO:1.
(5) A DNA comprising nucleotides 80 to 676 of SEQ ID NO:7.
(6) A DNA that hybridizes under stringent conditions with a DNA comprising the nucleotide sequence of SEQ ID NO:1 and that encodes a mammal-derived protein being homologous to a protein that comprises the amino acid sequence of SEQ ID NO:2 and having a cytidine deaminase activity.
(7) A DNA that hybridizes under stringent conditions with a DNA comprising the nucleotide sequence of SEQ ID NO:7 and that encodes a mammal-derived protein being homologous to a protein that comprises the amino acid sequence of SEQ ID NO:8 and having a cytidine deaminase activity.
(8) A genomic DNA or a fragment thereof comprising a nucleotide sequence of any one of (a) to (c) below:
 (a) SEQ ID NO:9,
 (b) SEQ ID NO:10, or
 (c) SEQ ID NO:35.
(9) A genomic DNA or a fragment thereof comprising a nucleotide sequence of any one of (a) to (e) below:
 (a) SEQ ID NO:11,
 (b) SEQ ID NO:12,
 (c) SEQ ID NO:13,
 (d) SEQ ID NO:14, or
 (e) SEQ ID NO:15.
(10) A DNA comprising a complementary nucleotide sequence to an arbitrary partial sequence of a nucleotide sequence of any one of (a) to (h) below:
 (a) SEQ ID NO:9,
 (b) SEQ ID NO:10,
 (c) SEQ ID NO:11,
 (d) SEQ ID NO:12,
 (e) SEQ ID NO:13,
 (f) SEQ ID NO:14,
 (g) SEQ ID NO:15, or
 (h) SEQ ID NO:35.
(11) A DNA comprising a nucleotide sequence of any one of (a) to (q) below:
 (a) SEQ ID NO:18,
 (b) SEQ ID NO:19,
 (c) SEQ ID NO:20,
 (d) SEQ ID NO:21,
 (e) SEQ ID NO:22,
 (f) SEQ ID NO:23,
 (g) SEQ ID NO:24,
 (h) SEQ ID NO:25,
 (i) SEQ ID NO:26,
 (j) SEQ ID NO:27,
 (k) SEQ ID NO:28,
 (l) SEQ ID NO:29,
 (m) SEQ ID NO:30,
 (n) SEQ ID NO:31,
 (O) SEQ ID NO:32,
 (p) SEQ ID NO:33, or,
 (q) SEQ ID NO:34.

Furthermore, a DNA encoding a mutant protein or a fragment thereof obtained by substituting, deleting, and/or modifying multiple amino acids, preferably 1 to 10 amino acids, particularly preferably 1 to 5 amino acids, or by inserting multiple amino acids, preferably 1 to 10 amino acids, particularly preferably 1 to 5 amino acids in the amino acid sequence constituting the above-defined AID protein of the present invention or a fragment thereof is included in the DNA of the present invention.

The term "under stringent conditions" used herein means, for example, the following conditions. For example, in the case of carrying out hybridization using a probe with not less than 50 bases in 0.9% NaCl, target temperature of causing 50% dissociation (Tm) can be calculated from the formula below, and the hybridization temperature can be set as the formula below.

$$Tm = 82.3°°C. + 0.41'(G+C)\% - 500/n - 0.61 \times (\text{formamide})\%$$

(n means the number of bases of the probe)
Temperature=Tm−25° C.

Also, in the case of using a probe with not less than 100 bases (G+C=40 to 50%), the changes of Tm as (1) and (2) below can be used as the indicator.

Every 1% mismatch decreases Tm by approximately 1° C.
(2) Every 1% formamide decreases Tm by 0.6 to 0.7° C.

Thus, the temperature condition in the case of combination of complete complementary strands can be set as below.
(A) 65 to 75° C. (without formamide)
(B) 35 to 45° C. (with 50% formamide)

The temperature condition in the case of combination of incomplete complementary strands can be set as below.
(A) 45 to 55° C. (without formamide)
(B) 35 to 42° C. (with 30% formamide)

In the case of using probes with not more than 23 bases, temperature can be 37° C., or the formula below can also be used as an indicator.

$$\text{Temperature} = 2° C. \times (\text{number of } A+T) + 4° C. \times (\text{number of } C+G) - 5° C.$$

The DNA of the present invention can be a DNA obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

The invention also includes a polypeptide, or fragment thereof, that differs from the corresponding sequence shown as SEQ ID NO:2 or 8. The differences are, preferably, differences or changes at a non-essential residue or a conservative substitution. In one embodiment, the polypeptide includes an amino acid sequence at least about 60% identical to a sequence shown as SEQ ID NO:2 or 8, or a fragment thereof. Preferably, the polypeptide is at least 65%, 70%, 75%, 80%, 85%, 90%, 95%, 98%, 99% or more identical to SEQ ID NO:2 or 8 and has at least one cytidine deaminase function or activity described herein. Preferred polypeptide fragments of the invention are at least 10%, preferably at least 20%, 30%, 40%, 50%, 60%, 70%, or more, of the length of the sequence shown as SEQ ID NO:2 or 8 and have at least one cytidine deaminase activity described herein. Or alternatively, the fragment can be merely an immunogenic fragment.

As used herein, "% identity" of two amino acid sequences, or of two nucleic acid sequences, is determined using the algorithm of Karlin and Altschul (PNAS USA 87:2264–2268, 1990), modified as in Karlin and Altschul, PNAS USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al (Nucleic Acids Res. 25:3389–3402, 1997). When utilizing BLAST and GappedBLAST programs the default parameters of the respective programs (e.g., XBLAST and NBLAST) are used to obtain nucleotide sequences homologous to a nucleic acid molecule of the invention.

Accordingly, in one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NO:1 or 7. More preferably, the isolated nucleic acid molecule is at least 65%, 70%, 75%, 80%, 85%, 90%, 91%, 92%, 93%, 94%, 95% 96%, 97%, 98%, 99%, or more, identical to the nucleotide sequence shown in SEQ ID NO:1 or 7. In the case of an isolated nucleic acid molecule which is longer than or equivalent in length to the reference sequence, e.g., SEQ ID NO:1 or 7, the comparison is made with the full length of the reference sequence. Where the isolated nucleic acid molecule is shorter that the reference sequence, e.g., shorter than SEQ ID NO:1 or 7, the comparison is made to a segment of the reference sequence of the same length (excluding any loop required by the homology calculation).

The DNA encoding the protein of the present invention can be prepared by the usual methods: cloning cDNA from mRNA encoding the protein of the present invention, isolating genomic DNA and splicing it, chemical synthesis, and so on.

(1) cDNA can be cloned from mRNA encoding the protein of the present invention by, for example, the method described below.

First, the mRNA encoding the protein of the present invention is prepared from the above-mentioned tissues or cells expressing and producing the protein of the present invention. mRNA can be prepared by isolating total RNA by a known method such as guanidine-thiocyanate method (Chirgwin et al., Biochemistry, 18:5294, 1979), hot phenol method, or AGPC method, and subjecting it to affinity chromatography using oligo-dT cellulose or poly-U Sepharose.

Then, with the mRNA obtained as a template, cDNA is synthesized, for example, by a well-known method using reverse transcriptase, such as the method of Okayama et al (Mol. Cell. Biol. 2:161 (1982); Mol. Cell. Biol. 3:280 (1983)) or the method of Hoffman et al. (Gene 25:263 (1983)), and converted into double-stranded cDNA. A cDNA library is prepared by transforming E. coli with plasmid vectors, phage vectors, or cosmid vectors having this cDNA or by transfecting E. coli after in vitro packaging.

The plasmid vectors used in this invention are not limited as long as they are replicated and maintained in hosts. Any phage vector that can be replicated in hosts can also be used. Examples of usually used cloning vectors are pUC19, λgt10, λgt11, and so on. When the vector is applied to immunological screening as mentioned below, a vector having a promoter that can express a gene encoding the desired protein in a host is preferably used.

cDNA can be inserted into a plasmid by, for example, the method of Maniatis et al. (Molecular Cloning, A Laboratory Manual, second edition, Cold Spring Harbor Laboratory, p. 1.53, 1989). cDNA can be inserted into a phage vector by, for example, the method of Hyunh et al. (DNA cloning, a practical approach, 1, p. 49 (1985)). These methods can be simply performed by using a commercially available cloning kit (for example, a product from Takara Shuzo). The recombinant plasmid or phage vector thus obtained is introduced into an appropriate host cell such as a prokaryote (for example, E. coli: HB101, DH5α, MC1061/P3, etc).

Examples of a method for introducing a plasmid into a host are, calcium chloride method, calcium chloride/rubidium chloride method and electroporation method, described in Molecular Cloning, A Laboratory Manual (second edition, Cold Spring Harbor Laboratory, p. 1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

The identification of cDNA encoding protein, its expression being augmented depending on the stimulation of cytokines like AID protein of the present invention, can be carried out by for example suppression subtractive hybridization (SSH)(Proc. Natl. Acad. Sci. USA, 93:6025–6030, 1996; Anal. Biochem., 240:90–97, 1996) taking advantage of suppressive PCR effect (Nucleic Acids Res., 23:1087–1088, 1995), using two cDNA libraries, namely, a cDNA library constructed from mRNA derived from stimulated cells (tester cDNA library) and one constructed from mRNA derived from unstimulated cells (driver cDNA library).

The preparation of cDNA libraries required for subtraction cloning can be performed by using a commercially available kit, for example, PCR-Select Subtraction Kit (CLONTECH, cat: K1804-1). The experiment can be performed according to the instructions accompanying the kit.

An example of a practical experimental procedure is listed below, briefly.

PolyA$^+$ RNA is prepared from cells with or without stimulation with appropriate stimulant as previously reported (Nucleic Acids Res., 26:911–918, 1998). Next, cDNA is prepared, using reverse transcriptase, from each polyA$^+$ RNA sample, as is the commonly used method. cDNA prepared from stimulated cells is used as tester cDNA and that prepared from unstimulated cells as driver cDNA.

According to the previous report mentioned above and experimental manuals accompanying the kit, driver cDNA is added to tester cDNA to perform subtraction. The efficiency of subtraction is monitored by adding small amount of exogenous DNA as a control. After subtraction, the exogenous DNA is concentrated.

The subtracted cDNA is cloned into an appropriate plasmid expression vector to construct a plasmid library by a commonly used method.

Similar to the previously reported method, many colonies are screened by differential hybridization method (Nucleic Acids Res., 26:911–918, 1998; RINSYO-MEN-EKI, 29:451–459, 1997). Here, as the hybridization probes, tester cDNA and driver cDNA mentioned above labeled with radioisotope can be used. Clones containing the objective DNA or containing exogenous DNA can be distinguished by hybridizing the exogenous DNA with replicant filters.

Objective cDNA or its fragment can be obtained by selecting clones giving strong signals against radiolabeled tester cDNA probe rather than radiolabeled driver cDNA probe.

Also, cDNA encoding the protein of the present invention can be accomplished by other general cDNA screening methods.

For instance, cDNA or a fragment encoding the protein of the present invention cloned by subtraction cloning method mentioned above, or chemically synthesized oligonucleotides corresponding to an amino acid sequence of the protein of the present invention, are labeled with $^{32}$P to make probes, then by well-known colony hybridization methods (Crunstein et al., Proc. Natl. Acid. Sci. USA, 72:3961, 1975) or plaque hybridization methods (Molecular Cloning, A Laboratory Manual, second edition, Cold Spring Harbor Laboratory, p.2.108, 1989), commercial or originally prepared cDNA libraries can be screened. Furthermore, a method to amplify DNA including cDNA encoding the protein of the present invention by PCR, by constructing a pair of PCR primers based on cDNA or its fragment encoding the protein of the present invention isolated by the subtraction cloning mentioned above, can be listed.

When a cDNA library prepared using a cDNA expression vector is used, the desired clone can be screened by the antigen-antibody reaction using an antibody against the desired protein. A screening method using PCR methodology is preferably used when many clones are subjected to screening.

The nucleotide sequence of the DNA thus obtained can be determined by the Maxam-Gilbert method (Maxam et al., Proc. Natl. Acad. Sci. USA, 74:560 (1977)) or the dideoxynucleotide synthetic chain termination method using phage M13 (Sanger et al., Proc. Natl. Acad. Sci. USA, 74:5463–5467 (1977)). The nucleotide sequence can be easily determined using a commercial DNA sequencer.

The whole or a part of the gene encoding the protein of the present invention can be obtained by excising the clone obtained as mentioned above with restriction enzymes and so on.

(2) Also, the DNA encoding the protein of the present invention can be isolated from genomic DNA derived from the cells expressing the protein of the present invention as mentioned above by the following methods.

Such cells are solubilized preferably by SDS or proteinase K, and the DNAs are deproteinized by repeating phenol extraction. RNAs are digested preferably with ribonuclease. The DNAs obtained are partially digested with appropriate restriction enzymes, and the DNA fragments obtained are amplified with appropriate phage or cosmid to generate a library. Then, clones having the desired sequence are detected, for example, by using radioactively labeled DNA probes, and the whole or a portion of the gene encoding the protein of the present invention is obtained from the clones by excision with restriction enzymes, etc.

For example, cDNA encoding a human-derived protein can be obtained by preparing a cosmid library into which human genomic DNAs (chromosomal DNAs) are introduced ("Laboratory Manual Human Genome Mapping," M. Hori and Y Nakamura, eds., Maruzen), screening the cosmid library to obtain positive clones containing DNA corresponding to the coding region of the desired protein, and screening the above cDNA library using the coding region DNA excised from the positive clones as a probe.

Also, the present invention relates to any fragment of DNA (cDNA, genomic DNA, etc.) encoding an AID protein (especially a human AID protein) of the present invention described above. DNA with a nucleotide sequence complementary to any nucleotide sequence of cDNA or genomic DNA is useful as a primer DNA in polymerase chain reaction (PCR). By PCR using a pair of primer DNAs, any partial nucleotide sequence of genomic DNA encoding AID protein (especially human AID protein) of the present invention can be amplified.

For instance, in the case that mutation or deletion of genomic DNA (especially exon) encoding the AID protein is presumed to cause a certain immunodeficiency or allergy, the existence of such a mutation or deletion can be analyzed by PCR described below.

(1) Prepare a pair of primers comprising nucleotide sequence complementary to any partial nucleotide sequence of genomic DNA encoding an AID protein of the present invention.

(2) Amplify the objective partial nucleotide sequence of the genomic DNA using the pair of primers, using genomic DNA encoding AID protein obtained from tissue or cells of immunodeficiency or allergy patients as templates.

(3) Analyze the existence of PCR products and the nucleotide sequence of the PCR products, and identify the mutation and deletion in the genomic DNA by comparing the nucleotide sequence and corresponding nucleotide sequence of genomic DNA encoding AID protein derived from a normal human.

Thus, the method described above can not only elucidate, for example, the relationship between immunodeficiency and/or allergy and AID protein, but also be used for the diagnosis of a certain kind of disease, in the case that AID protein is the cause of the disease.

Examples of the nucleotide sequence of the primer DNA are as follows:

(1) A DNA comprising a complementary nucleotide sequence to an arbitrary partial sequence of a nucleotide sequence of any one of (a) to (h) below:
 (a) SEQ ID NO:9,
 (b) SEQ ID NO:10,
 (c) SEQ ID NO:11,
 (d) SEQ ID NO:12,
 (e) SEQ ID NO:13,
 (f) SEQ ID NO:14,
 (g) SEQ ID NO:15, or
 (h) SEQ ID NO:35.

(2) A DNA comprising a nucleotide sequence of any one of (a) to (q) below:
 (a) SEQ ID NO:18,
 (b) SEQ ID NO:19,
 (c) SEQ ID NO:20,
 (d) SEQ ID NO:21,
 (e) SEQ ID NO:22,
 (f) SEQ ID NO:23,
 (g) SEQ ID NO:24,
 (h) SEQ ID NO:25,
 (i) SEQ ID NO:26,
 (j) SEQ ID NO:27,
 (k) SEQ ID NO:28,
 (l) SEQ ID NO:29,
 (m) SEQ ID NO:30,
 (n) SEQ ID NO:31,
 (O) SEQ ID NO:32,
 (p) SEQ ID NO:33, or,
 (q) SEQ ID NO:34.

Also, the present invention relates to the use of the above-mentioned DNA fragment as a primer DNA in polymerase chain reaction.

Examples of the combination of primer DNAs for PCR in diagnosis accomplished by PCR gene amplification and by analyzing it are as follows:

(1) a DNA comprising the nucleotide sequence of SEQ ID NO:31 and a DNA comprising the nucleotide sequence of SEQ ID NO:32, (2) a DNA comprising the nucleotide sequence of SEQ ID NO:20 and a DNA comprising the nucleotide sequence of SEQ ID NO:22, (3) a DNA comprising the nucleotide sequence of SEQ ID NO:21 and a DNA comprising the nucleotide sequence of SEQ ID NO:30, (4) a DNA comprising the nucleotide sequence of SEQ ID NO:24 and a DNA comprising the nucleotide sequence of SEQ ID NO:25, (5) a DNA comprising the nucleotide sequence of SEQ ID NO:23 and a DNA comprising the nucleotide sequence of SEQ ID NO:27, (6) a DNA comprising the nucleotide sequence of SEQ ID NO:23 and a DNA comprising the nucleotide sequence of SEQ ID NO:28, (7) a DNA comprising the nucleotide sequence of SEQ ID NO:23 and a DNA comprising the nucleotide sequence of SEQ ID NO:29, (8) a DNA comprising the nucleotide sequence of SEQ ID NO:26 and a DNA comprising the nucleotide sequence of SEQ ID NO:27, (9) a DNA comprising the nucleotide sequence of SEQ ID NO:26 and a DNA comprising the nucleotide sequence of SEQ ID NO:28,

(10) a DNA comprising the nucleotide sequence of SEQ ID NO:26 and a DNA comprising the nucleotide sequence of SEQ ID NO:29,

(11) a DNA comprising the nucleotide sequence of SEQ ID NO:34 and a DNA comprising the nucleotide sequence of SEQ ID NO:28,

(12) a DNA comprising the nucleotide sequence of SEQ ID NO:34 and a DNA comprising the nucleotide sequence of SEQ ID NO:29,

(13) a DNA comprising the nucleotide sequence of SEQ ID NO:33 and a DNA comprising the nucleotide sequence of SEQ ID NO:29, or,

(14) a DNA comprising the nucleotide sequence of SEQ ID NO:18 and a DNA comprising the nucleotide sequence of SEQ ID NO:19.

Moreover, the present invention also relates to a recombinant vector comprising the DNA encoding the protein of the present invention. As a recombinant vector of the present invention, any vector can be used as long as it is capable of retaining replication or self-multiplication in each host cell of prokaryotic and/or eukaryotic cells, including plasmid vectors and phage vectors.

The recombinant vector can easily be prepared by ligating the DNA encoding a protein of the present invention with a vector for recombination available in the art (plasmid DNA and bacteriophage DNA) by the usual method.

Specific examples of the vectors used for recombination are *E. coli*-derived plasmids such as pBR322, pBR325, pUC12, pUC13, and pUC19, yeast-derived plasmids such as pSH19 and pSH15, and *Bacillus subtilis*-derived plasmids such as pUB110, pTP5, and pC194. Examples of phages are a bacteriophage such as λ phage, and an animal or insect virus (pVL1393, Invitrogen) such as a retrovirus, vaccinia virus, and nuclear polyhedrosis virus.

An expression vector is useful for expressing the DNA encoding the protein of the present invention and for producing the protein of the present invention. The expression vector is not limited as long as it expresses the gene encoding the protein of the present invention in various prokaryotic and/or eukaryotic host cells and produces this protein. Examples thereof are pMAL C2, pEF-BOS (Nucleic Acids Res. 18:5322 (1990) and so on), pME18S (Experimental Medicine: SUPPLEMENT, "Handbook of Genetic Engineering" (1992) and so on), etc.

Also, the protein of the present invention can be produced as a fusion protein with other proteins. It can be prepared as a fusion protein, for example, with GST (Glutathione S-transferase) by subcloning a cDNA encoding the protein of the present invention, for example, into plasmid pGEX4T1 (Pharmacia), by transforming *E. coli* DH5α, and by culturing the transformant.

When bacteria, particularly *E. coli*, are used as host cells, an expression vector generally comprises, at least, a promoter/operator region, an initiation codon, the DNA encoding the protein of the present invention, termination codon, terminator region, and replicon.

When yeast, animal cells, or insect cells are used as hosts, an expression vector is preferably comprising, at least, a promoter, an initiation codon, the DNA encoding the protein of the present invention, and a termination codon. It may also comprise the DNA encoding a signal peptide, enhancer sequence, 5'- and 3'-untranslated region of the gene encoding the protein of the present invention, splicing junctions, polyadenylation site, selectable marker region, and a replicon. The expression vector may also contain, if required, a gene for gene amplification (marker) that is usually used.

A promoter/operator region to express the protein of the present invention in bacteria comprises a promoter, an operator, and a Shine-Dalgarno (SD) sequence (for example, AAGG). For example, when the host is *Escherichia*, it preferably comprises Trp promoter, lac promoter, recA promoter, λPL promoter, lpp promoter, tac promoter, or the like. Examples of a promoter to express the protein of the present invention in yeast are PH05 promoter, PGK promoter, GAP promoter, ADH promoter, and so on. When the host is *Bacillus*, examples thereof are SL01 promoter, SP02 promoter, penP promoter, and so on. When the host is a eukaryotic cell such as a mammalian cell, examples thereof are SV40-derived promoter, retrovirus promoter, heat shock promoter, and so on, and preferably an SV-40 or retrovirus-derived one. As a matter of course, the promoter is not limited to the above examples. In addition, using an enhancer is effective for expression.

A preferable initiation codon is, for example, a methionine codon (ATG).

A commonly used termination codon (for example, TAG, TAA, TGA) is exemplified as a termination codon.

Usually, natural or synthetic terminators are used as a terminator region.

A replicon means a DNA capable of replicating the whole DNA sequence in host cells, and includes a natural plasmid, an artificially modified plasmid (DNA fragment prepared from a natural plasmid), a synthetic plasmid, and so on. Examples of preferable plasmids are pBR322 or its artificial derivatives (DNA fragment obtained by treating pBR322 with appropriate restriction enzymes) for *E. coli*, yeast 2µ plasmid or yeast chromosomal DNA for yeast, and pRSV-neo ATCC 37198, pSV2dhfr ATCC 37145, pdBPV-MMT-neo ATCC 37224, pSV2neo ATCC 37149, and such for mammalian cells.

An enhancer sequence, polyadenylation site, and splicing junction that are usually used in the art, such as those derived from SV40, can also be used.

A selectable marker usually employed can be used according to the usual method. Examples thereof are resistance genes for antibiotics, such as tetracycline, ampicillin, or kanamycin.

Examples of genes for gene amplification are dihydrofolate reductase (DHFR) gene, thymidine kinase gene, neomycin resistance gene, glutamate synthase gene, adenosine deaminase gene, ornithine decarboxylase gene, hygromycin-B-phosphotransferase gene, aspartate transcarbamylase gene, etc.

The expression vector of the present invention can be prepared by continuously and circularly linking at least the above-mentioned promoter, initiation codon, DNA encoding the protein of the present invention, termination codon, and terminator region, to an appropriate replicon. If desired, appropriate DNA fragments (for example, linkers, restriction sites, and so on), can be used by the usual method such as digestion with a restriction enzyme or ligation using T4 DNA ligase.

Transformants of the present invention can be prepared by introducing the expression vector mentioned above into host cells.

Host cells used in the present invention are not limited as long as they are compatible with an expression vector mentioned above and can be transformed. Examples thereof are various cells such as wild-type cells or artificially established recombinant cells usually used in the technical field of the present invention (for example, bacteria (*Escherichia* and *Bacillus*), yeast (*Saccharomyces, Pichia*, and such), animal cells, or insect cells).

*E. coli* or animal cells are preferably used. Specific examples are *E. coli* (DH5α, TB1, HB101, and such), mouse-derived cells (COP, L, C127, Sp2/0, NS-1, NIH 3T3, and such), rat-derived cells (PC12, PC12h), hamster-derived cells (BHK, CHO, and such), monkey-derived cells (COS1, COS3, COS7, CV1, Velo, and such), and human-derived cells (Hela, diploid fibroblast-derived cells, myeloma cells, and HepG2, and such).

An expression vector can be introduced (transformed (transfected)) into host cells by known methods.

Transformation can be performed, for example, according to the method of Cohen et al. (Proc. Natl. Acad. Sci. USA, 69:2110 (1972)), the protoplast method (Mol. Gen. Genet., 168:111 (1979)), or the competent method (J. Mol. Biol., 56:209 (1971)) when the hosts are bacteria (*E. coli, Bacillus subtilis*, and such), the method of Hinnen et al. (Proc. Natl. Acad. Sci. USA, 75:1927 (1978)), or the lithium method (J. Bacteriol., 153:163 (1983)) when the host is *Saccharomyces cerevisiae*, the method of Graham (Virology, 52:456 (1973)) when the hosts are animal cells, and the method of Summers et al. (Mol. Cell. Biol., 3:2156–2165 (1983)) when the hosts are insect cells.

The protein of the present invention can be produced by cultivating transformants (in the following, this term includes transfectants) comprising an expression vector prepared as mentioned above in nutrient media.

The nutrient media preferably comprises a carbon source, an inorganic nitrogen source, or an organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meat extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on).

Cultivation is performed by a method known in the art. Cultivation conditions such as temperature, pH of the media, and cultivation time are selected appropriately so that the protein of the present invention is produced in large quantities.

Specific media and cultivation conditions used depending on host cells are illustrated below, but are not limited thereto.

When the hosts are bacteria, actinomycetes, yeast, or filamentous fungi, liquid media comprising the nutrient source mentioned above are appropriate. Media with a pH of 5 to 8 are preferably used.

When the host is *E. coli*, examples of preferable media are LB media, M9 media (Miller et al. Exp. Mol. Genet., Cold Spring Harbor Laboratory, p. 431 (1972)), and so on. Using these media, cultivation can be performed usually at 14 to 43° C. for about 3 to 24 hours with aeration and stirring, if necessary.

When the host is *Bacillus*, cultivation can be performed usually at 30 to 40° C. for about 16 to 96 hours with aeration and stirring, if necessary.

When the host is yeast, an example of medium is Burkholder minimal medium (Bostian, Proc. Natl. Acad. Sci. USA, 77:4505 (1980)). The pH of the medium is preferably 5 to 8. Cultivation can be performed usually at 20 to 35° C. for about 14 to 144 hours with aeration and stirring, if necessary.

When the host is an animal cell, examples of media are MEM containing about 5 to 20% fetal bovine serum (Science, 122:501 (1952)), DMEM (Virology, 8:396 (1959)), RPMI1640 medium (J. Am. Med. Assoc., 199:519 (1967)), 199 medium (Proc. Soc. Exp. Biol. Med., 73:1 (1950)), and so on. The pH of the medium is preferably about 6 to 8. Cultivation can be performed usually at about 30 to 40° C. for about 15 to 72 hours with aeration and stirring, if necessary.

When the host is an insect cell, an example of medium is Grace's medium containing fetal bovine serum (Proc. Natl. Acad. Sci. USA, 82:8404 (1985)). The pH thereof is preferably about 5 to 8. Cultivation can be performed usually at about 20 to 40° C. for 15 to 100 hours with aeration and stirring, if necessary.

The protein of the present invention can be produced by cultivating transformants, especially mammalian cells, as mentioned above and allowing them to secrete the protein into the culture supernatant.

A culture filtrate (supernatant) is obtained by a method such as filtration or centrifugation of the obtained culture, and the protein of the present invention is purified and isolated from the culture filtrate by methods commonly used in order to purify and isolate a natural or synthetic protein.

Examples of the isolation and purification method are a method utilizing solubility, such as salting out and solvent precipitation method; a method utilizing the difference in molecular weight, such as dialysis, ultrafiltration, gel filtration, and sodium dodecyl sulfate-polyacrylamide gel electrophoresis; a method utilizing charge, such as ion exchange chromatography and hydroxylapatite chromatography; a method utilizing specific affinity, such as affinity column chromatography; a method utilizing the difference in hydrophobicity, such as reverse phase high performance liquid chromatography; and a method utilizing the difference in isoelectric point, such as isoelectric focusing.

When the protein of the present invention exists in the periplasm or cytoplasm of cultured transformants (for example, *E. coli*), first, the cells are harvested by a usual method such as filtration or centrifugation and suspended in appropriate buffer. After the cell wall and/or cell membrane of the cells and such are disrupted by a method such as lysis with sonication, lysozyme, and freeze-thawing, the membrane fraction comprising the protein of the present invention is obtained by a method such as centrifugation or filtration. The membrane fraction is solubilized with a detergent such as Triton-X100 to obtain the crude extract. Finally, the protein is isolated and purified from the crude extract by a usual method as illustrated above.

By using a DNA (cDNA or genomic DNA) encoding a human-derived AID protein included in the protein of the present invention, transgenic non-human mammals secreting the human AID protein in their body can be prepared. Namely, by integrating the human-derived DNA into an endogenous locus of non-human mammals (e.g. mouse), the human AID protein of the present invention encoded by the DNA is expressed and secreted in their body. The transgenic non-human mammals are included in the present invention.

The transgenic non-human mammals can be prepared according to the method usually used for producing a transgenic animal (for example, see "Newest Manual of Animal Cell Experiment," LIC press, Chapter 7, pp. 361–408, (1990)).

Specifically, for example, a transgenic mouse can be produced as follows. Embryonic stem cells (ES cells) obtained from normal mouse blastocysts are transformed with an expression vector in which the gene encoding the human AID protein of the present invention and a marker gene (for example, neomycin resistance gene) have been inserted in an expressible manner. ES cells in which the gene encoding the human AID protein of the present invention has been integrated into the endogenous gene are screened by a usual method based on expression of the marker gene. Then, the ES cells screened are microinjected into a fertilized egg (blastocyst) obtained from another normal mouse (Proc. Natl. Acad. Sci. USA, 77:7380–7384 (1980); U.S. Pat. No. 4,873,191).

The blastocyst is transplanted into the uterus of another normal mouse as the foster mother. Then, founder mice are born from the foster mother. By mating the founder mice with normal mice, heterozygous transgenic mice are obtained. By mating the heterozygous transgenic mice with each other, homozygous transgenic mice are obtained according to Mendel's laws.

Also, a so-called "knockout mouse" can be generated based on the nucleotide sequence of DNA encoding mouse AID protein included in the present invention. The "knockout mouse" in the present invention means the mouse in which the endogenous gene encoding the mouse AID protein of the present invention is knocked-out (inactivated). For example, it can be generated by positive-negative selection method applying homologous recombination (U.S. Pat. Nos. 5,464,764; 5,487,992; 5,627,059; Proc. Natl. Acad. Sci. USA, 86:8932–8935, 1989; Nature, 342:435–438, 1989; etc.), and such knockout mice are one embodiment of the present invention.

The "antibody" in the present invention means a polyclonal antibody (antiserum) or a monoclonal antibody, and preferably a monoclonal antibody.

Specifically, it includes an antibody reactive to the above-mentioned protein of the present invention and a fragment thereof.

The "antibody" of the present invention also includes a natural antibody that can be prepared by immunizing mammals such as mice, rats, hamsters, guinea pigs, or rabbits with the protein of the present invention (including natural, recombinant, and chemically synthesized protein and cell), a fragment thereof, or a transformant highly expressing the protein of interest by recombinant technology mentioned above; a chimeric antibody and a humanized antibody (CDR-grafted antibody) that can be produced by recombinant technology; and a human monoclonal antibody that can be produced by using human antibody-producing transgenic animals.

The monoclonal antibody includes those having any one of the isotypes of IgG, IgM, IgA, IgD, or IgE. IgG or IgM is preferable.

The polyclonal antibody (antiserum) or monoclonal antibody of the present invention can be produced by known methods. Namely, mammals, preferably, mice, rats, hamsters, guinea pigs, rabbits, cats, dogs, pigs, goats, horses, or cows, or more preferably, mice, rats, hamsters, guinea pigs, or rabbits are immunized, for example, with an antigen mentioned above with Freund's adjuvant, if necessary. The polyclonal antibody can be obtained from the serum obtained from the animal so immunized. The monoclonal antibodies are produced as follows. Hybridomas are produced by fusing the antibody-producing cells obtained from the animal so immunized and myeloma cells incapable of producing autoantibodies. Then the hybridomas are cloned, and clones producing the monoclonal antibodies showing the specific affinity to the antigen used for immunizing the mammal are screened.

Specifically, the monoclonal antibody can be produced as follows. Immunizations are done by injecting or implanting once or several times the above-mentioned protein of the present invention, a fragment thereof, the cells that express the protein, and so on, as an immunogen, if necessary, with Freund's adjuvant, subcutaneously, intramuscularly, intravenously, through the footpad, or intraperitoneally into mice, rats, hamsters, guinea pigs, or rabbits, preferably mice, rats or hamsters (including transgenic animals generated so as to produce antibodies derived from another animal such as a transgenic mouse producing human antibodies). Usually, immunizations are performed one to four times every one to fourteen days after the first immunization. Antibody-producing cells are obtained from the mammal so immunized in about one to five days after the last immunization.

Hybridomas that secrete a monoclonal antibody can be prepared by the method of Köhler and Milstein (Nature, 256:495–497 (1975)) and by its modified method. Namely, hybridomas are prepared by fusing antibody-producing cells contained in a spleen, lymph node, bone marrow, or tonsil obtained from the non-human mammal immunized as mentioned above, preferably a spleen, with myeloma cells without autoantibody-producing ability, which are derived from, preferably, a mammal such as mice, rats, guinea pigs, hamsters, rabbits, or humans, or more preferably, mice, rats, or humans.

For example, mouse-derived myeloma P3/X63-AG8.653 (653; ATCC No. CRL1580), P3/NSI/1-Ag4-1 (NS-1), P3/X63-Ag8.U1 (P3U1), SP2/0-Ag14 (Sp2/0, Sp2), PAI, F0, or BW5147; rat-derived myeloma 210RCY3-Ag.2.3.; or human-derived myeloma U-266AR1, GM1500-6TG-A1-2, UC729-6, CEM-AGR, D1R11, or CEM-T15 can be used as a myeloma used for the cell fusion.

Hybridoma clones producing monoclonal antibodies can be screened by cultivating the hybridomas, for example, in microtiter plates and by measuring the reactivity of the culture supernatant in the well in which hybridoma growth is observed, to the immunogen used for the immunization mentioned above, for example, by an enzyme immunoassay such as RIA and ELISA.

The monoclonal antibodies can be produced from hybridomas by cultivating the hybridomas in vitro or in vivo such as in the ascites of mice, rats, guinea pigs, hamsters, or rabbits, preferably mice or rats, more preferably mice and isolating the antibodies from the resulting culture supernatant or ascites fluid of a mammal.

In vitro cultivation can be performed depending on the property of cells to be cultured, on the object of a test study, and on various culture, by using known nutrient media or any nutrient media derived from known basal media for growing, maintaining, and storing the hybridomas to produce monoclonal antibodies in the culture supernatant.

Examples of basal media are low calcium concentration media such as Ham'F12 medium, MCDB153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Monoclonal antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), affinity chromatography using anti-immunoglobulin column or protein A column.

Furthermore, monoclonal antibodies can be obtained in a large quantity by cloning a gene encoding a monoclonal antibody from the hybridoma, generating transgenic bovines, goats, sheep, or pigs in which the gene encoding the antibody is integrated in its endogenous gene using transgenic animal generating technique, and recovering the monoclonal antibody derived from the antibody gene from milk of the transgenic animals (Nikkei Science, No. 4, pp. 78–84 (1997)).

The "chimeric antibody" of the present invention means a monoclonal antibody prepared by genetic engineering, and specifically, a chimeric monoclonal antibody, for example, mouse/human chimeric antibody, whose variable region is a mouse immunoglobulin-derived variable region and whose constant region is a human immunoglobulin-derived constant region.

The constant region derived from human immunoglobulin has the amino acid sequence inherent in each isotype such as IgG, IgM, IgA, IgD, IgE, etc. The constant region of the recombinant chimeric monoclonal antibody of the present invention can be that of human immunoglobulin belonging to any isotype. Preferably, it is the constant region of human IgG.

The chimeric monoclonal antibody of the present invention can be produced, for example, as follows. Needless to say, the production method is not limited thereto.

For example, mouse/human chimeric monoclonal antibody can be prepared, by referring to Experimental Medicine: SUPPLEMENT, 1.6, No. 10 (1988); and Examined Published Japanese Patent Application (JP-B) No. Hei 3-73280. Namely, it can be prepared by ligating CH gene (C gene encoding the constant region of H chain) obtained from the DNA encoding human immunoglobulin to the downstream of active VH genes (rearranged VDJ gene encoding the variable region of H chain) obtained from the DNA encoding mouse monoclonal antibody isolated from the hybridoma producing the mouse monoclonal antibody, and by ligating the $C_L$ gene (C gene encoding the constant region of L chain) obtained from the DNA encoding human immunoglobulin to the downstream of active $V_L$ genes (rearranged VJ gene encoding the variable region of L chain) obtained from the DNA encoding the mouse monoclonal antibody isolated from the hybridoma, and operably inserting those into the same or different vectors in an expressible manner, followed by transformation of host cells with the expression vector, and cultivation of the transformants.

Specifically, DNAs are first extracted from mouse monoclonal antibody-producing hybridoma by the usual method, digested with appropriate restriction enzymes (for example, EcoRI and HindIII), electrophoresed (using, for example, 0.7% agarose gel), and analyzed by Southern blotting. After the electrophoresed gel is stained, for example, with ethidium bromide and photographed, the gel is given marker positions, washed twice with water, and soaked in 0.25 M HCl for 15 minutes. Then, the gel is soaked in 0.4 N NaOH solution for 10 minutes with gentle stirring. The DNAs are transferred to a filter for 4 hours following the usual method. The filter is recovered and washed twice with 2×SSC. After the filter is sufficiently dried, it is baked at 75° C. for 3 hours, treated with 0.1×SSC/0.1% SDS at 65° C. for 30 minutes, and then soaked in 3×SSC/0.1% SDS. The filter obtained is treated with prehybridization solution in a plastic bag at 65° C. for 3 to 4 hours.

Next, $^{32}$P-labeled probe DNA and hybridization solution are added to the bag and reacted at 65° C. about 12 hours. After hybridization, the filter is washed under an appropriate salt concentration, reaction temperature, and time (for example, 2×SSC/0.1% SDS, room temperature, 10 minutes). The filter is put into a plastic bag with a little 2×SSC, and subjected to autoradiography after the bag is sealed.

Rearranged VDJ gene and VJ gene encoding H chain and L chain of mouse monoclonal antibody respectively are identified by Southern blotting mentioned above. The region comprising the identified DNA fragment is fractionated by sucrose density gradient centrifugation and inserted into a phage vector (for example, Charon 4A, Charon 28, λEMBL3, λEMBL4, etc.). E. coli (for example, LE392, NM539, etc.) are transformed with the phage vector to generate a genomic library. The genomic library is screened by plaque hybridization such as the Benton-Davis method (Science, 196:180–182 (1977)) using appropriate probes (H chain J gene, L chain (κ) J gene, etc.) to obtain positive clones comprising rearranged VDJ gene or VJ gene respectively. By making the restriction map and determining the nucleotide sequence of the clones obtained, it is confirmed that genes comprising the desired, rearranged $V_H$ (VDJ) gene or $V_L$ (VJ) gene have been obtained.

Separately, human CH gene and human CL gene used for chimerization are isolated. For example, when a chimeric antibody with human IgG1 is produced, $C\gamma_1$ gene is isolated as a $C_H$ gene, and Cκ gene is also isolated as a $C_L$ gene, are isolated. These genes can be isolated from human genomic library with mouse $C\gamma_1$ gene and mouse Cκ gene, corresponding to human $C\gamma_1$ gene and human Cκ gene, respectively, as probes, taking advantage of the high homology between the nucleotide sequences of mouse immunoglobulin gene and that of human immunoglobulin gene.

Specifically, DNA fragments comprising human Cκ gene and an enhancer region are isolated from human λ Charon 4A HaeIII-AluI genomic library (Cell, 15:1157–1174 (1978)), for example, using a 3 kb HindIII-BamHI fragment from clone Ig146 (Proc. Natl. Acad. Sci. USA, 75:4709–4713 (1978)) and a 6.8 kb EcoRI fragment from clone MEP10 (Proc. Natl. Acad. Sci. USA, 78:474–478 (1981)) as probes. In addition, for example, after human fetal hepatocyte DNA is digested with HindIII and fractioned by agarose gel electrophoresis, a 5.9 kb fragment is inserted into λ788 and then human $C\gamma_1$ gene is isolated with the probes mentioned above.

Using a mouse $V_H$ gene, mouse $V_L$ gene, human $C_H$ gene, and human $C_L$ gene so obtained, and taking the promoter region and enhancer region into consideration, human $C_H$ gene is inserted downstream of mouse $V_H$ gene and human $C_L$ gene is inserted downstream of mouse $V_L$ gene in an expression vector such as pSV2gpt or pSV2neo with appropriate restriction enzymes and DNA ligase following the usual method. In this case, chimeric genes of mouse $V_H$ gene/human $C_H$ gene and mouse $V_L$ gene/human $C_L$ gene can be respectively inserted into the same or a different expression vector.

Chimeric gene-inserted expression vector(s) thus prepared are introduced into myeloma cells (e.g., P3X63 Ag8 653 cells or SP210 cells) that do not produce antibodies by the protoplast fusion method, DEAE-dextran method, calcium phosphate method, or electroporation method. The transformants are screened by cultivating them in a medium containing a drug corresponding to the drug resistance gene inserted into the expression vector and, then, cells producing the desired chimeric monoclonal antibodies are obtained.

Desired chimeric monoclonal antibodies are obtained from the culture supernatant of antibody-producing cells thus screened.

The "humanized antibody (CDR-grafted antibody)" of the present invention is a monoclonal antibody prepared by genetic engineering and specifically means a humanized monoclonal antibody wherein a portion or the whole of the complementarity determining regions of the hyper-variable region are derived from those of the hyper-variable region from mouse monoclonal antibody, the framework regions of the variable region are derived from those of the variable region from human immunoglobulin, and the constant region is derived from that from human-immunoglobulin.

The complementarity determining regions of the hyper-variable region exists in the hyper-variable region in the variable region of an antibody and means three regions which directly bind, in a complementary manner, to an antigen (complementarity-determining residues, CDR1, CDR2, and CDR3). The framework regions of the variable region mean four comparatively conserved regions intervening upstream, downstream or between the three complementarity-determining regions (framework region, FR1, FR2, FR3, and FR4).

In other words, a humanized monoclonal antibody means that in which the whole region except a portion or the whole region of the complementarity determining regions of the hyper-variable region of a mouse monoclonal antibody has been replaced with their corresponding regions derived from human immunoglobulin.

The constant region derived from human immunoglobulin has the amino acid sequence inherent in each isotype such as IgG, IgM, IgA, IgD, and IgE. The constant region of a humanized monoclonal antibody of the present invention can be that from human immunoglobulin belonging to any isotype. Preferably, it is the constant region of human IgG. The framework regions of the constant region derived from human immunoglobulin are not particularly limited.

The humanized monoclonal antibody of the present invention can be produced, for example, as follows. Needless to say, the production method is not limited thereto.

For example, a recombinant humanized monoclonal antibody derived from mouse monoclonal antibody can be prepared by genetic engineering, referring to Published Japanese Translations of PCT International Publication No. Hei 4-506458 and Unexamined Published Japanese Patent Application (JP-A) No. Sho 62-296890. Namely, at least one mouse H chain CDR gene and at least one mouse L chain CDR gene corresponding to the mouse H chain CDR gene are isolated from hybridomas producing mouse monoclonal antibody, and human H chain gene encoding the whole region except human H chain CDR corresponding to mouse H chain CDR mentioned above and human L chain gene encoding the whole region except human L chain CDR corresponding to mouse L chain CDR mentioned above are isolated from human immunoglobulin genes.

The mouse H chain CDR gene(s) and the human H chain gene(s) so isolated are inserted, in an expressible manner, into an appropriate vector so that they can be expressed. Similarly, the mouse L chain CDR gene(s) and the human L chain gene(s) are inserted, in an expressible manner, into another appropriate vector so that they can be expressed. Alternatively, the mouse H chain CDR gene(s)/human H chain gene(s) and mouse L chain CDR gene(s)/human L chain gene(s) can be inserted, in an expressible manner, into the same expression vector so that they can be expressed. Host cells are transformed with the expression vector thus prepared to obtain transformants producing humanized monoclonal antibody. By cultivating the transformants, desired humanized monoclonal antibody is obtained from culture supernatant.

The "human antibody" used in the present invention is immunoglobulin in which the entire regions comprising the variable and constant region of the H chain, and the variable and constant region of the L chain constituting immunoglobulin are derived from the genes encoding human immunoglobulin.

The human antibody can be produced in the same way as the production method of polyclonal or monoclonal antibodies mentioned above by immunizing, with an antigen, a transgenic animal which for example, at least human immunoglobulin gene(s) have been integrated into the locus of a non-human mammal such as a mouse by the usual method.

For example, a transgenic mouse producing human antibodies is prepared by the methods described in already published literatures (Nature Genetics, 7:13–21 (1994); Nature Genetics, 15:146–156 (1997); JP-WA Hei 4-504365; WO94/25585; Nikkei Science, No. 6, pp. 40–50 (1995); WO94/25585; Nature, 368:856–859 (1994); JP-WA No. Hei 6-500233).

The "portion of an antibody" used in the present invention means a partial region of the antibody, and preferably the monoclonal antibody of the present invention as mentioned above, and specifically, means F(ab')$_2$, Fab', Fab, Fv (variable fragment of antibody), sFv, dsFv (disulfide stabilized Fv), or dAb (single domain antibody) (Exp. Opin. Ther. Patents, 6, No. 5, pp. 441–456 (1996)).

"F(ab')$_2$" and "Fab'" can be produced by treating immunoglobulin (monoclonal antibody) with a protease such as pepsin and papain, and means an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of $V_L$ (L chain variable region) and $C_L$ (L chain constant region), and an H chain fragment composed of $V_H$ (H chain variable region) and $C_H\gamma 1$ ($\gamma 1$ region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')$_2$.

The "cell producing a monoclonal antibody reactive to a protein or a fragment thereof" of the present invention means any cell producing the above-described monoclonal antibody of the present invention.

More specifically, the following is included:

(1) B cells that are obtained by immunizing the non-human mammals with the above-mentioned protein of the present invention, a fragment thereof, or the cells producing the protein and that produce a monoclonal antibody reactive to the protein of the present invention or a fragment thereof.

(2) The above-mentioned hybridomas (fused cell) prepared by fusing the thus-obtained B cells producing the antibody with myeloma cells derived from mammals.

(3) Monoclonal antibody-producing transformants obtained by transforming cells other than the monoclonal antibody-producing B cells and hybridomas with genes encoding the monoclonal antibody isolated from the monoclonal antibody-producing B cells or hybridomas (either the heavy chain-encoding gene or the light chain-encoding gene, or both).

The monoclonal antibody-producing transformants of (3) mean recombinant cells producing a recombinant monoclonal antibody produced by B cells of (1) or hybridomas of (2). These antibody producing-transformants can be produced by the method as used for producing the above-described chimeric monoclonal antibody and humanized monoclonal antibody.

The "pharmaceutical composition" used herein means a pharmaceutical composition comprising of any of the protein, fragment thereof, antibody, or portion thereof defined hereinabove, and a pharmaceutically acceptable carrier.

The "pharmaceutically acceptable carrier" includes an excipient, a diluent, an expander, a disintegrating agent, a stabilizer, a preservative, a buffer, an emulsifier, an aromatic, a colorant, a sweetener, a viscosity-increasing agent, a flavor, a dissolving agent, or other additives. Using one or more of such carriers, a pharmaceutical composition can be formulated into tablets, pills, powders, granules, injections, solutions, capsules, troches, elixirs, suspensions, emulsions, or syrups. The pharmaceutical composition can be administered orally or parenterally. Other forms for parenteral administration include a solution for external application, suppository for rectal administration, and pessary, prescribed by the usual method, which comprises one or more active ingredient.

The dosage can vary depending on the age, sex, weight, and symptoms of a patient, effect of treatment, administration route, period of treatment, or the kind of active ingredient (protein or antibody mentioned above) contained in the pharmaceutical composition. Usually, the pharmaceutical composition can be administered to an adult in a dose of 10 µg to 1000 mg (or 10 µg to 500 mg) per one administration. Depending on various conditions, the lower dosage may be sufficient in some cases, and a higher dosage may be necessary in other cases.

In particular, the injection can be produced by dissolving or suspending the antibody in a non-toxic, pharmaceutically acceptable carrier such as physiological saline or commercially available distilled water for injections by adjusting the concentration to 0.1 µg antibody/ml carrier to 10 mg antibody/ml carrier. The injection thus produced can be administered to a human patient in need of treatment in a dose of 1 µg to 100 mg/kg body weight, preferably 50 µg to 50 mg/kg body weight, once or more times a day. Examples of administration routes are medically appropriate administration routes such as intravenous injection, subcutaneous injection, intradermal injection, intramuscular injection, or intraperitoneal injection, preferably intravenous injection.

The injection can also be prepared into a non-aqueous diluent (for example, propylene glycol, polyethylene glycol, vegetable oil such as olive oil, and alcohols such as ethanol), suspension, or emulsion.

The injection can be sterilized by filtration with a bacteria-non-penetrable filter, by mixing bacteriocide, or by irradiation. The injection can be prepared at the time of use. Namely, it is freeze-dried to make a sterile solid composition, and can be dissolved in sterile distilled water for injection or another solvent before use.

The pharmaceutical composition of the present invention is useful as a drug for preventing and treating, for example, primary immunodeficiency syndrome with congenital disorder of immune system, mainly immunodeficiency considered to develop by B lymphocyte deficiency, decrease, or dysfunction (e.g., sex-linked agammaglobulinemia, sex-linked agammaglobulinemia with growth hormone deficiency, immunoglobulin deficiency with high IgM level, selective IgM deficiency, selective IgE deficiency, immunoglobulin heavy chain gene deletion, κ chain deficiency, IgA deficiency, IgG subclass selective deficiency, CVID (common variable immunodeficiency), infantile transient dysgammaglobulinemia, Rosen syndrome, severe combined immunodeficiency (sex-linked, autosomal recessive), ADA (adenosine deaminase) deficiency, PNP (purine nucleoside phosphorylase) deficiency, MHC class II deficiency, reticular dysplasia, Wiskott-Aldrich syndrome, ataxia telangiectasia, DiGeorge syndrome, chromosomal aberration, familial Ig hypermetabolism, hyper IgE syndrome, Gitlin syndrome, Nezelof syndrome, Good syndrome, osteodystrophy, transcobalamin syndrome, secretory bead syndrome, etc.), various diseases with antibody production deficiency that are secondary immunodeficiency syndrome with disorder of immune system caused by an acquired etiology (for example, AIDS, etc.), and/or various allergic diseases (e.g., bronchial asthma, atopic dermatitis, conjunctivitis, allergic rhinitis, allergic enteritis, drug-induced allergy, food allergy, allergic urticaria, glomerulonephritis, etc.), and for relieving conditions due to various immunodeficiencies associated with the diseases.

The DNA of the present invention described above, namely, "DNA comprising any partial nucleotide sequence of SEQ ID NO:7, from SEQ ID NO:9 to SEQ ID NO:15, or SEQ ID NO:35, those with partial chemical modification, DNA comprising complementary nucleotide sequences to the partial sequence, or those with partial chemical modification" are included.

Here, the "partial nucleotide sequence" means the partial nucleotide sequence comprising any number of bases at any region included in any nucleotide sequence listed in SEQ ID NO:7, from SEQ ID NO:9 to SEQ ID NO:15, or SEQ ID NO:35.

The DNA is useful as probes in DNA hybridization or RNA hybridization procedures. For the purpose of using the DNA as a probe, continuous nucleotide sequences of over 20 bases, preferably continuous nucleotide sequences of over 50 bases, more preferably over 100 bases, much more preferably over 200 bases, especially preferably over 300 bases, can be used as the partial nucleotide sequences.

Also, the DNA described above, as mentioned before, are useful as primers for PCR. For the purpose of using the DNA as PCR primers, continuous partial nucleotide sequences of from 5 to 100 bases, preferably from 5 to 70 bases, more preferably from 5 to 50 bases, much more preferably from 5 to 30 bases, can be used as the partial nucleotide sequences.

Moreover, the DNA described above are useful as antisense drug. The DNA, by hybridizing to a DNA or an RNA encoding the AID protein of the present invention, can inhibit transcription of the DNA to mRNA or translation of the mRNA into the protein.

For the purpose of using above-mentioned DNA to antisense drug, the partial nucleotide sequence consists of 5 to 100 consecutive nucleotides, preferably 5 to 70 consecutive nucleotides, more preferably 5 to 50 consecutive nucleotides, and still more preferably 5 to 30 consecutive nucleotides.

When the DNA is used as an antisense DNA pharmaceutical, the DNA sequence can be modified chemically in part for extending the half-life (stability) of the blood concentration of the DNA administered to patients, for increasing the intracellular-membrane permeability of the DNA, or for increasing the degradation resistance or the absorption of the orally administered DNA in the digestive organs. The chemical modification includes, for example, the modification of the phosphate bonds, the riboses, the nucleotide bases, the sugar moiety, the 3' end and/or the 5' end in the structure of the oligonucleotide DNA.

The modification of phosphate bonds includes, for example, the conversion of one or more of the bonds to phosphodiester bonds (D-oligo), phosphorothioate bonds, phosphorodithioate bonds (S-oligo), methyl phosphonate (MP-oligo), phosphoroamidate bonds, non-phosphate bonds or methyl phosphonothioate bonds, or combinations thereof. The modification of the ribose includes, for example, the conversion to 2'-fluororibose or 2'-O-methylribose. The modification of the nucleotide base includes, for example, the conversion to 5-propynyluracil or 2-aminoadenine.

Also, another embodiment of the present invention relates to "methods of identifying substances regulating the production of the AID protein of the present invention or the transcription of the gene encoding AID protein to mRNA." The method of the present invention is namely "the method of screening of drugs capable of regulating functions of AID protein or AID gene."

As the cells in the method of the present invention, any cells, as long as capable of producing AID protein of the present invention, can be used. For instance, native cells (preferably of mouse or human), transgenic cells transformed with a gene encoding an AID protein of the present invention, cells introduced with RNA encoding an AID protein of the present invention, etc., can be used.

As the host cells for preparing the transgenic cells, various cells, mentioned in the part explaining in detail the methods of expressing the protein of the present invention using the DNA of the protein described above, can be used.

For instance, various cells such as naturally established cells or artificially established transgenic cells (e.g. bacteria (*Escherichia, Bacillus*), yeast (*Saccharomyces, Pichia*), animal cells and insect cells) can be exemplified.

Preferably, animal cells, namely, cells derived from mouse (COP, L, C127, Sp2/0, NS-1, or NIH3T3, etc.), cells derived from rat (PC 12, PC12h, etc.), cells derived from hamster (BHK, and CHO, etc.), cells derived from monkey (COS1, COS3, COS7, CV1, and Velo, etc.), and cells derived from human (Hela, cells derived from diploid fibroblast, HEK293 cells, myeloma cells, and Namalwa, etc.) can be exemplified.

The "substance" in the present invention means natural substance existing in the nature and any substance prepared artificially. The substances can be grouped into "peptidic substance" and "non-peptidic substance."

As the "non-peptidic substance," "DNA comprising partial nucleotide sequence, or chemically modified DNA derived from it" that are useful as antisense drugs as described above, "antisense RNA" with similar structural and pharmacological property to the antisense DNA, or any chemically synthesized "compounds" can be exemplified. Examples of "compounds" are compounds other than DNA, RNA, and the above-mentioned peptidic substances, which have a molecular weight from approximately 100 to approximately 1000, preferably from approximately 100 to approximately 800, more preferably from approximately 100 to approximately 600.

As the "peptidic substance," antibodies already described above in detail (preferably monoclonal antibodies, more preferably recombinant antibodies or human monoclonal antibodies), oligopeptides, or chemically modified substance derived from them can be exemplified. Examples of an oligopeptide are a peptide comprising 5 to 30 amino acids, preferably 5 to 20 amino acids. The chemical modification can be designed depending on various purposes, for example, for increased half-life in blood in the case of administering in vivo, or for increased tolerance against degradation or increased absorption in digestive tract after oral administration.

Methods described in from (24) to (28) above include so-called reporter gene assays, as one of the method of the present invention.

As the "reporter protein," luciferase derived from firefly or sea pansy, or GFP derived from jellyfish, are preferred.

As the "reporter gene assay," methods described below are representative.

Transgenic cells are generated by transforming cells commonly used in the production of recombinant proteins with expression vector, in which a gene encoding the target protein and a gene encoding the reporter protein are inserted into the vector so that the transcription of the gene encoding the reporter protein to mRNA is induced by the signal of the transcription of the gene of target protein to mRNA. The test substances (described above) are applied to the obtained transformant cells. Analysis that whether the compound affects the expression of transporter molecule can be accomplished by measuring the level of the target protein by indirect measurement of the amount of fluorescence emitted by the reporter protein expressed in parallel with the target protein (for reference, see U.S. Pat. No. 5,436,128 and U.S. Pat. No. 5,401,629).

The identification of the compounds using the present assay can be accomplished by manual operation, but it can also be readily and simply done automatically by so-called High-Throughput Screening using robots (SOSHIKI BAIYO KOUGAKU, 23:521–524; U.S. Pat. No. 5,670, 113).

The terms "cells" and "substances" used in the methods described above have the same meaning as defined above.

The substances identified by the methods of the present invention are very useful as drugs for the therapy of various diseases considered to be caused by the hyperfunction or deficiency of the AID protein of the present invention or by the deficiency or mutation of the AID gene, or for remission of various symptoms associated with the diseases.

DESCRIPTION OF DRAWINGS

FIG. 1(*a*) shows the electrophoresis of DNA including an Sα sequence looped out by class switch recombination, amplified by PCR using DNA derived from mouse B cell clone CH12F3-2 cultured under various conditions.

Lanes 1 and 6 show the electrophoresis of marker DNAs. Lane 2 shows the electrophoresis of PCR products produced using DNA from cells cultured in conditions excluding IL-4, CD40L, TGF β and cycloheximide as a template. Lane 3 shows the electrophoresis of PCR products produced using DNA from cells cultured in the presence of cycloheximide only, as a template. Lane 4 shows the electrophoresis of PCR products produced using DNA from cells cultured in the presence of IL-4, CD40L and TGF β as a template. Lane 5 shows the electrophoresis of PCR products produced using DNA from cells cultured in the presence of IL-4, CD40L, TGF β, and cycloheximide as a template.

FIG. 1(*b*) shows the result of Southern hybridization of DNA including an Sα sequence looped out by class switch recombination, amplified by PCR using DNA derived from mouse B cell clone CH12F3-2 cultured under various conditions.

Lane 1 shows the result of hybridization of PCR products produced using DNA from cells cultured in conditions excluding IL-4, CD40L, TGF β and cycloheximide as a template. Lane 2 shows the result of Southern hybridization of PCR products produced using DNA from cells cultured in the presence of cycloheximide only as a template. Lane 3 shows the result of hybridization of PCR products produced using DNA from cells cultured in the presence of IL-4, CD40L, and TGF α as a template. Lane 4 shows the result of hybridization against PCR products produced using DNA from cells cultured in the presence of IL-4, CD40L, TGF α and cycloheximide as a template.

FIG. 2 is a pair of photographs showing the production of DNA including an Sα sequence looped out by class switch recombination, amplified by PCR using DNA derived from mouse B cell clone CH12F3-2 cultured in various conditions.

FIG. 2(*a*) shows the electrophoresis of DNA including an Sα sequence looped out by class switch recombination in mouse B cell clone CH12F3-2 cultured in various conditions, stained with ethidium bromide.

Lanes 1 and 6 show the electrophoresis of marker DNAs. Lane 2 shows the electrophoresis of PCR products produced using DNA from cells cultured in conditions excluding IL-4, CD40L, TGF β and cycloheximide as a template. Lane 3 shows the electrophoresis of PCR products producing using DNA from cells cultured in the presence of cycloheximide only, as a template. Lane 4 shows the electrophoresis of PCR products produced using DNA from cells cultured in the presence of IL-4, CD40L and TGF β as a template. Lane 5 shows the electrophoresis of PCR products produced using DNA from cells cultured in the presence of Il-4, CD40L, TGF β, and cycloheximide as a template.

Figures 2A, 2B:
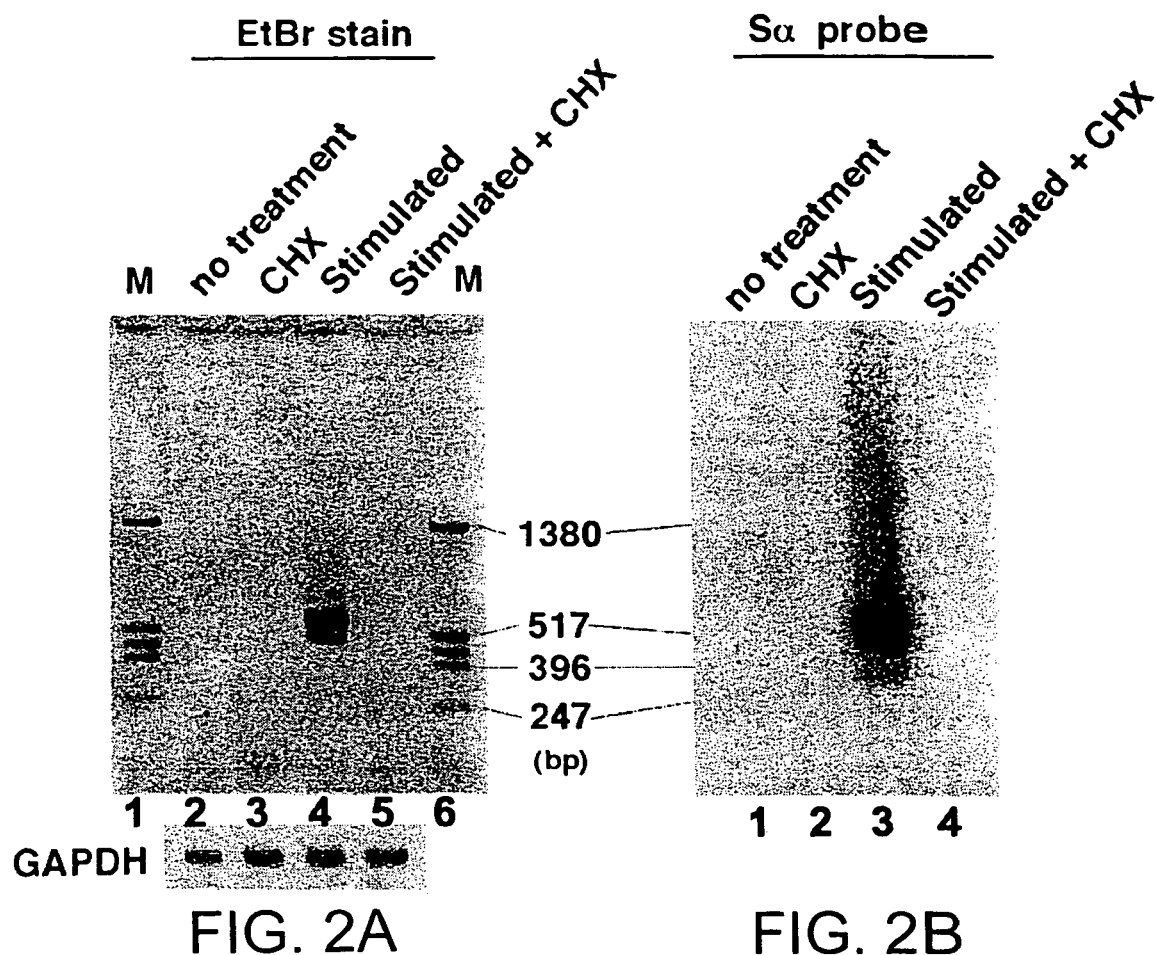

FIG. 2(b) shows the result of Southern hybridization of DNA including an Sα sequence looped out with class switch recombination, amplified by PCR using DNA derived from mouse B cell clone CH12F3-2 cultured under various conditions.

Lane 1 shows the result of hybridization of PCR products produced using DNA from cells cultured under conditions excluding IL-4, CD40L, TGF β and cycloheximide, as a template. Lane 2 shows the result of hybridization against PCR products produced using DNA from cells cultured in the presence of cycloheximide only as a template. Lane 3 shows the result of hybridization against PCR products produced using DNA from cells cultured in the presence of IL-4, CD40L, and TGF β as a template. Lane 4 shows the result of hybridization against PCR products produced using DNA from cells cultured in the presence of IL-4, CD40L, TGF β and cycloheximide as a template.

Figure 3:
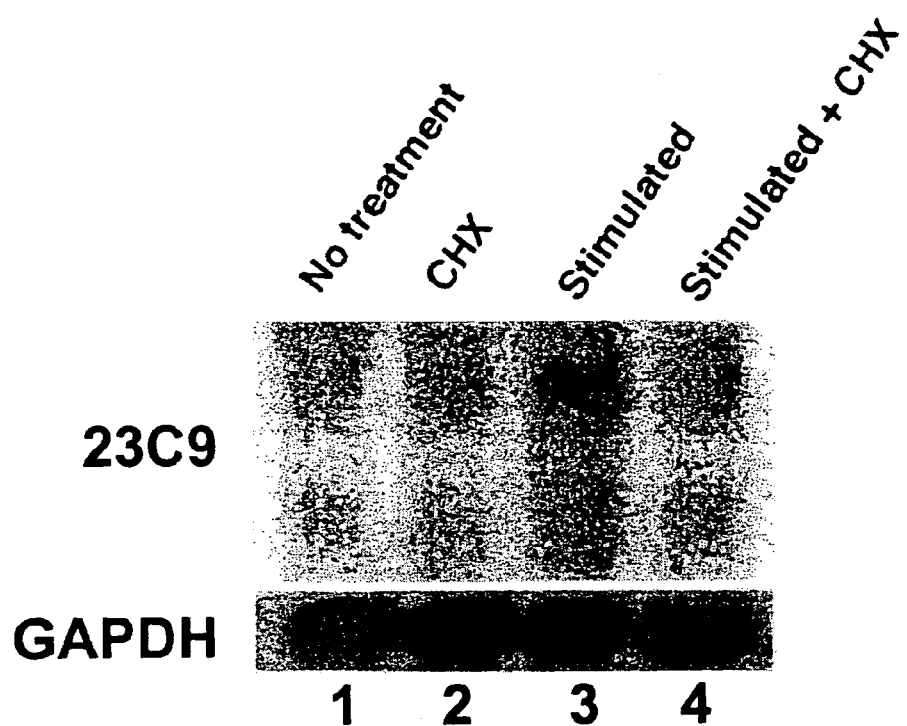

FIG. 3 shows the result of Northern blotting using a radiolabeled cDNA fragment encoding a 23C9 (AID) protein as a probe, against mRNA derived from mouse B cell clone CH12F3-2 cultured under the various conditions.

Lane 1 shows the result of blotting against mRNA from cells cultured in conditions excluding IL-4, CD40L, TGF β and cycloheximide. Lane 2 shows the result of blotting against mRNA from cells cultured in the presence of cycloheximide only. Lane 3 shows the result of blotting against mRNA from cells cultured in the presence of IL-4, CD40L, and TGF β. Lane 4 shows the result of blotting against mRNA from cells cultured in the presence of IL-4, CD40L, TGF β, and cycloheximide.

Figure 4:
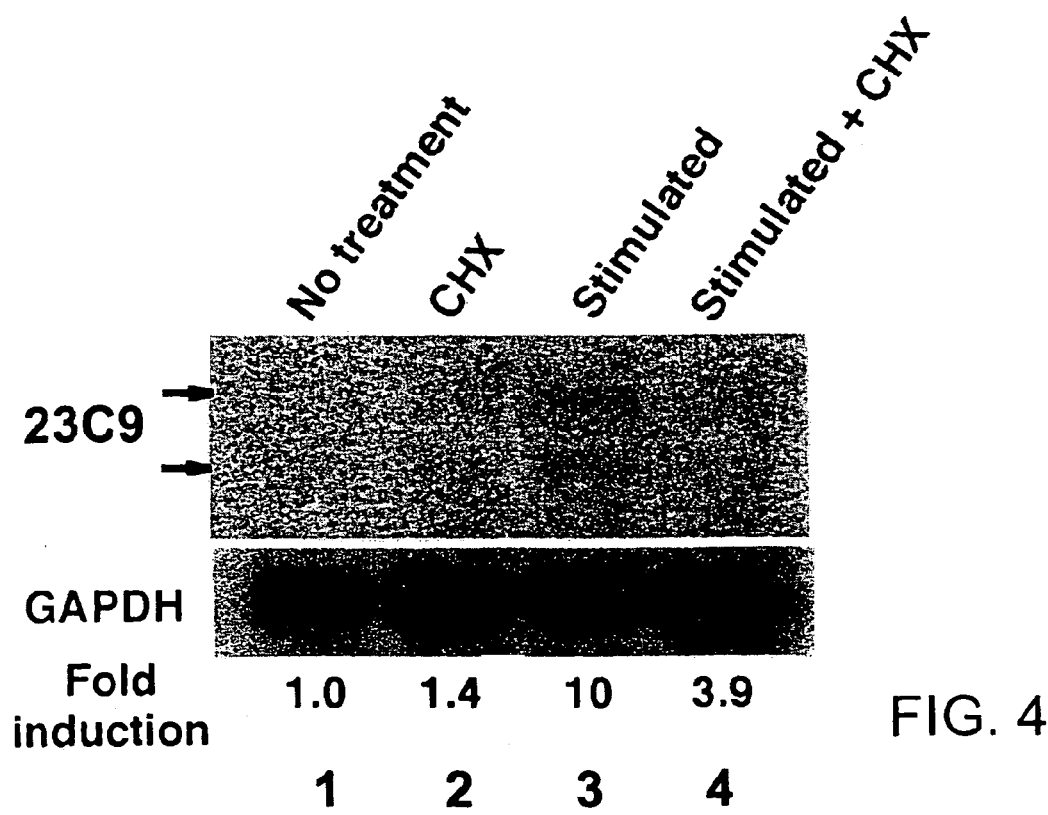

FIG. 4 shows the result of Northern blotting using a radio-labeled cDNA fragment coding 23C9 (AID) protein as a probe against mRNA derived from mouse B cell clone CH12F3-2 cultured in various conditions.

Lane 1 shows the result of blotting against mRNA from cells cultured in conditions excluding IL-4, CD40L, TGF β, and cycloheximide Lane 2 shows the result of blotting against mRNA from cells cultured in the presence of cycloheximide, only. Lane 3 shows the result of blotting against mRNA from cells cultured in the presence of IL-4, CD40L, and TGF β. Lane 4 shows the result of blotting against mRNA from cells cultured in the presence of IL-4, CD40L, TGF β, and cycloheximide.

FIG. 5 shows the homology between an amino acid sequence of mouse AID protein (SEQ ID NO:2) and that of mouse APOBEC-1 (SEQ ID NO:36).

An amino acid in a closed box shows an identical amino acid. A region in an open box indicates a cytidine deaminase motif. An amino acid with an asterisk (*) or an arrow indicates an amino acid conserved among APOBEC-1 proteins derived from rat, mouse, rabbit, and human.

Figure 6:
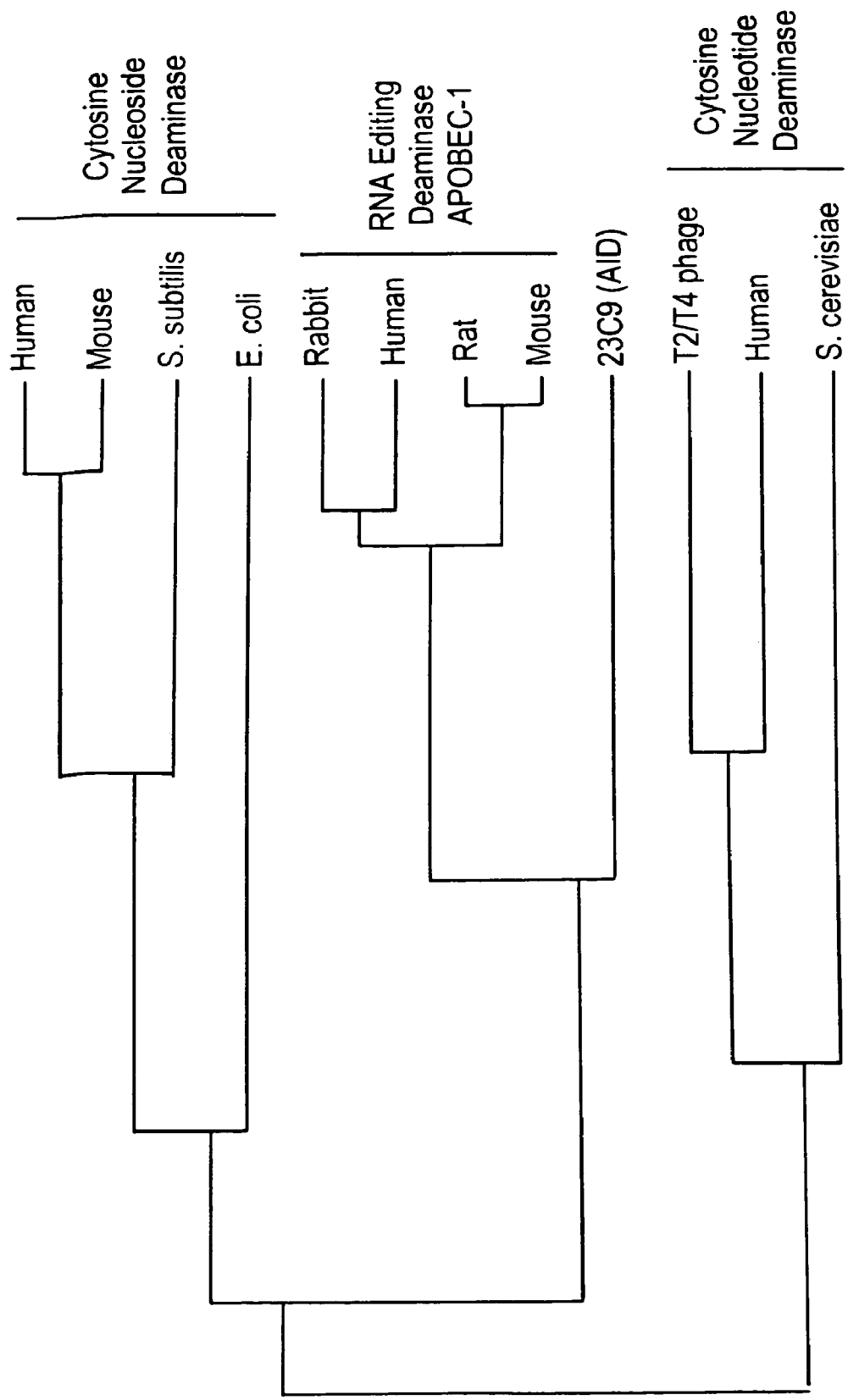

FIG. 6 shows a phylogenic tree of various enzymes belonging to a cytosine nucleoside/nucleotide deaminase family, prepared based on cytidine deaminase motif.

Figures 7, 8:
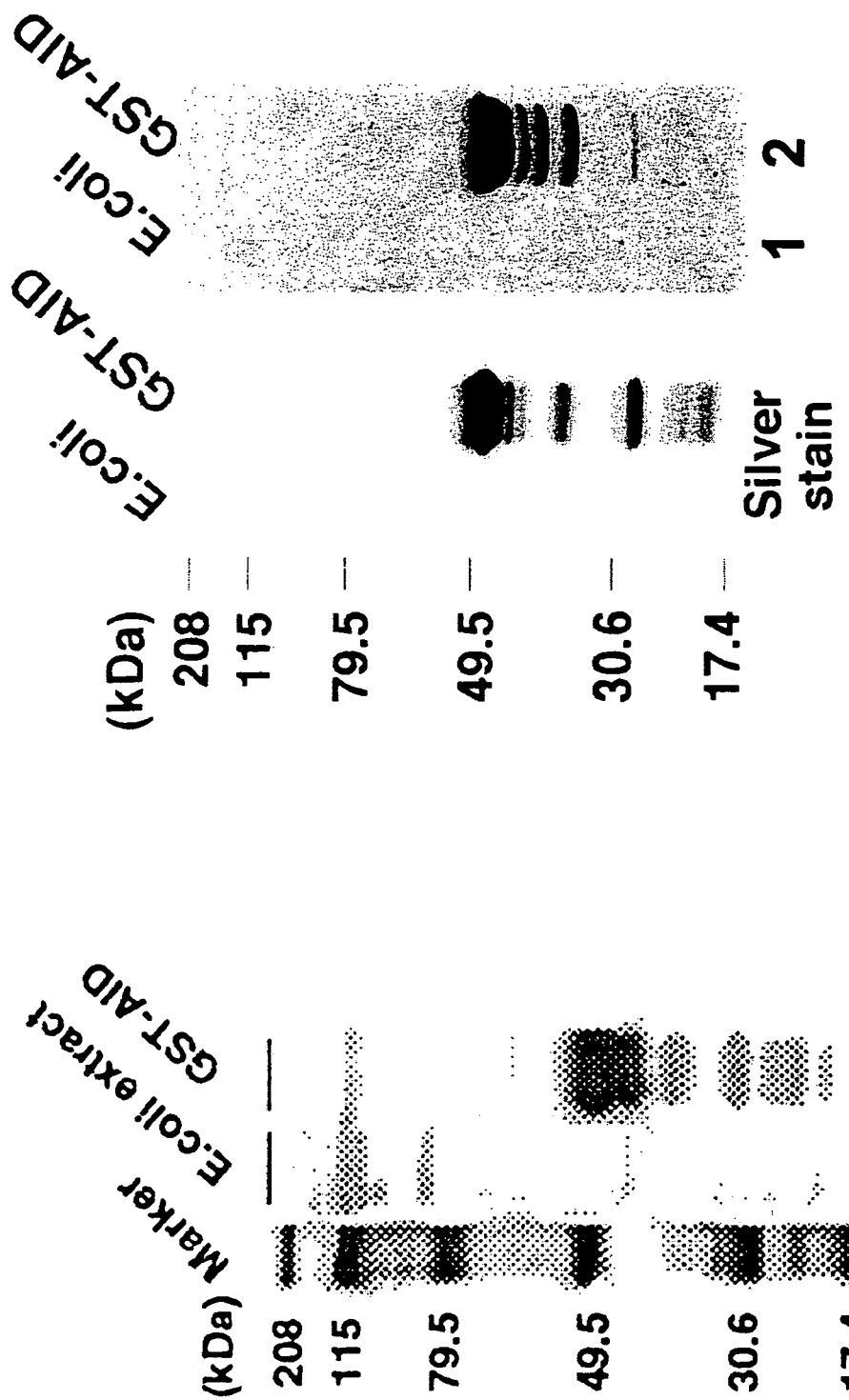

FIG. 7 shows a photograph indicating the electrophoretic state for AID-GST fusion protein in the molecular weight analysis by the gel electrophoresis and silver staining method.

Lane 1 shows the electrophoretic state for a marker molecule. Lane 2 shows the electrophoretic state for various proteins included in extracts from wild type *Escherichia coli* DH 5α. Lane 3 shows the electrophoretic state for purified AID-GST fusion protein.

FIG. 8 shows the electrophoretic state for AID-GST fusion protein by Western blotting using anti-AID protein peptide antibody.

Lane 1 shows the electrophoretic state for various proteins included in the extract from wild type *E. coli* DH5α.

Lane 2 shows the electrophoretic state for purified AID-GST protein.

Figure 9:
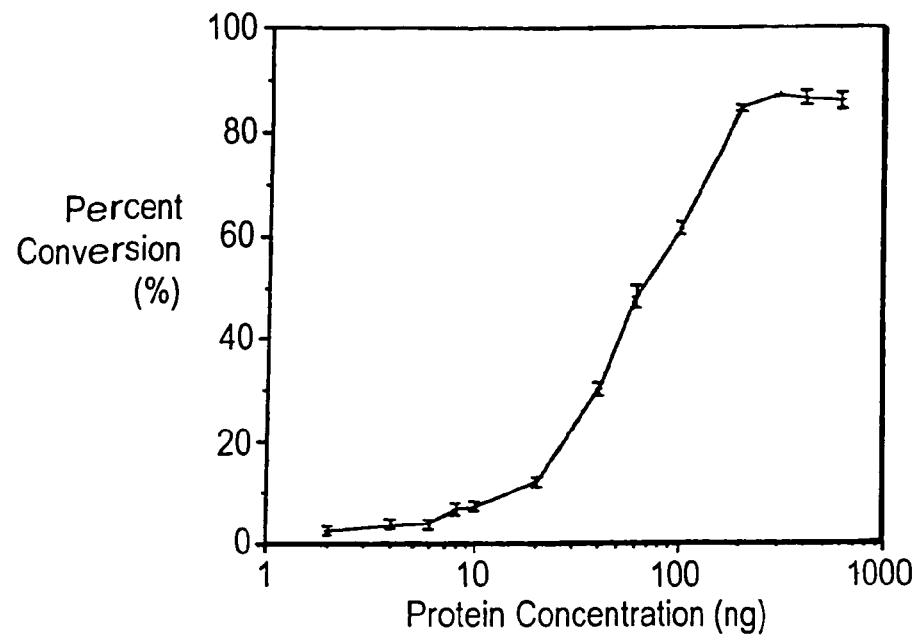

FIG. 9 shows a cytidine deaminase activity depending on the concentrations of AID proteins.

Figure 10:
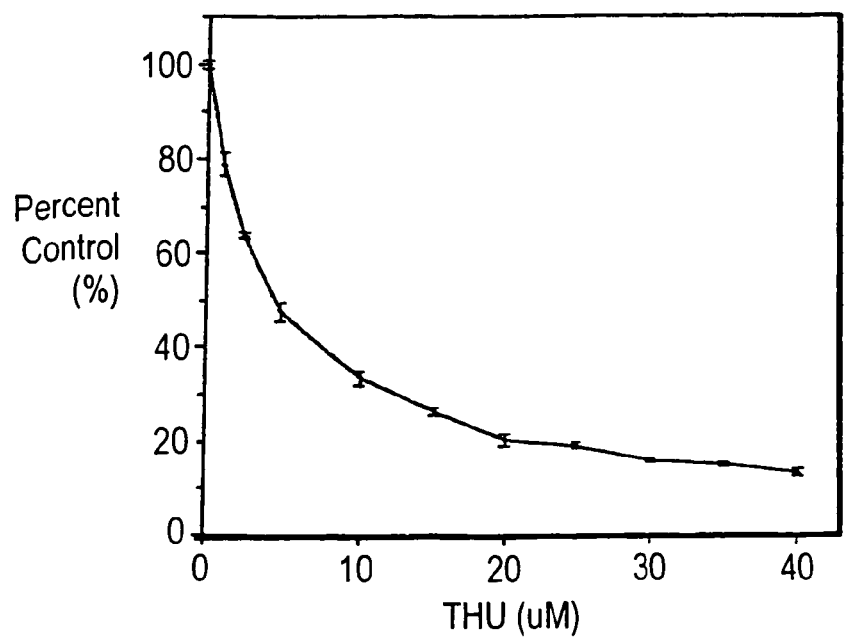

FIG. 10 shows the inhibitory effect of tetrahydrouridine which is an inhibitor specific to cytidine deaminase on a cytidine deaminase activity in AID protein.

Figure 11:
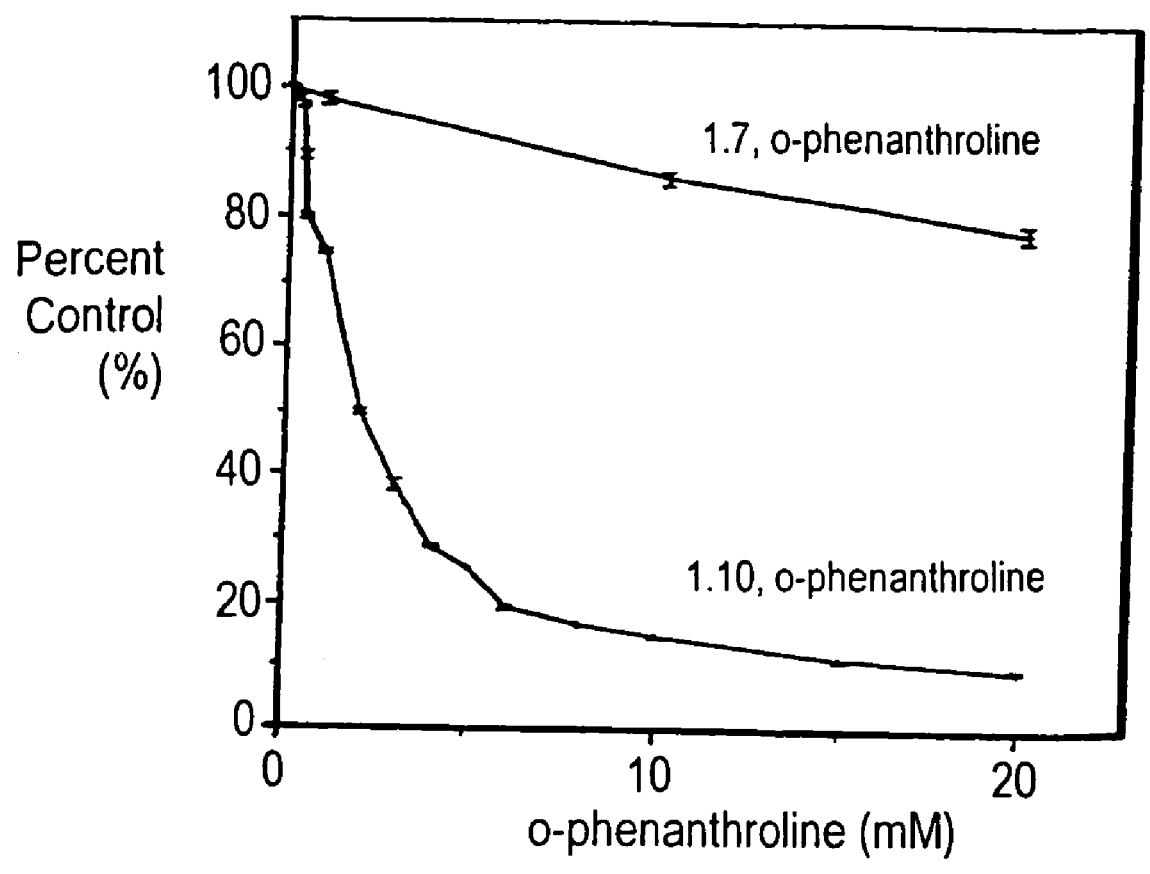

FIG. 11 shows the inhibitory effect of each of 1,10-o-phenanthrolime which is a zinc-chelating agent, and 1,7-o-phenanthroline which is an inactivated isomer thereof on a cytidine deaminase activity in AID protein.

Figure 12:
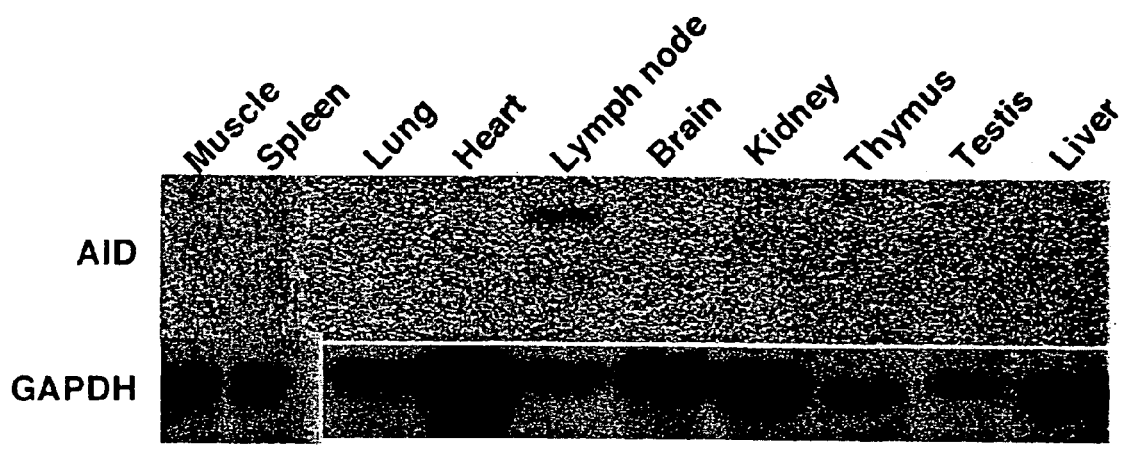

FIG. 12 is a photograph indicating expression state for mRNA of AID in various tissues in mouse, analyzed by Northern blotting method.

Figure 13:
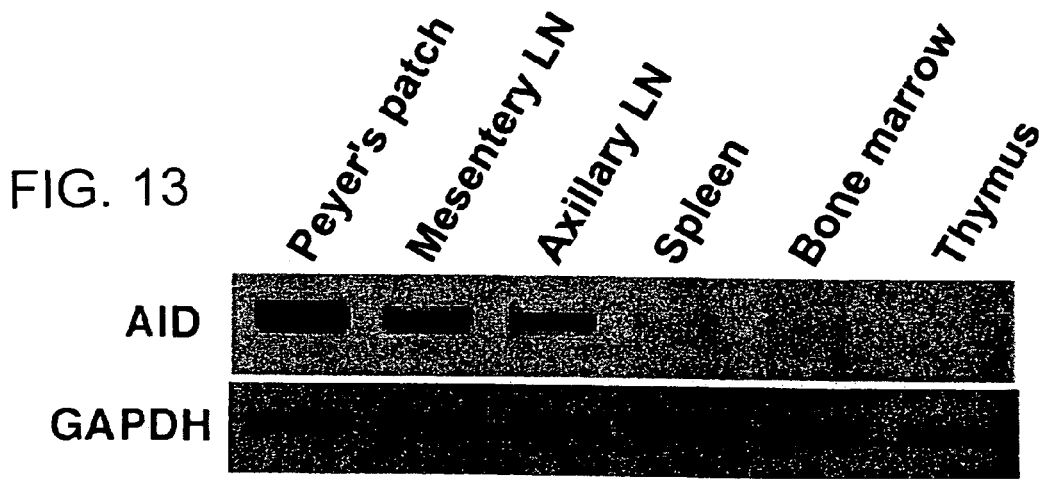

FIG. 13 is a photograph indicating the expression state for mRNA of AID in various lymphatic tissues in mouse, analyzed by RT-PCR method.

Figure 14:
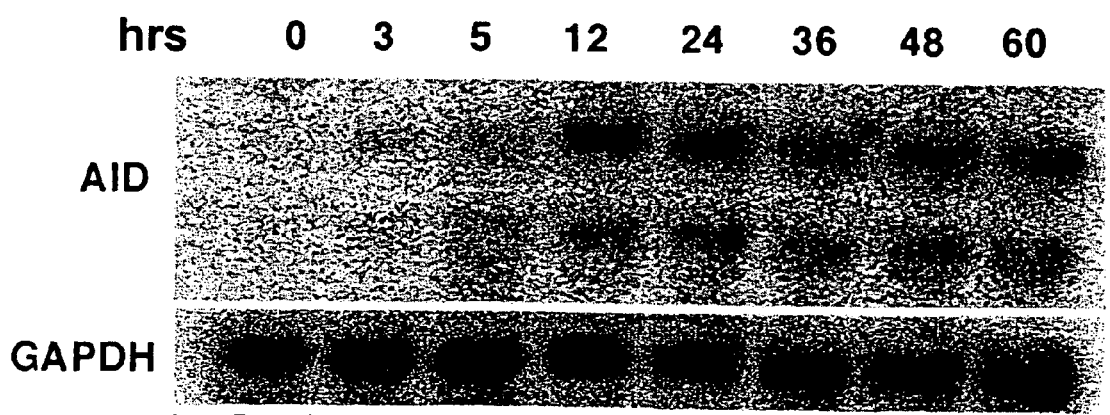

FIG. 14 is the photograph showing expression state for mRNA of AID over time, in activated mouse B cell clone CH12F3-2, analyzed by Northern blotting method.

Figure 15:
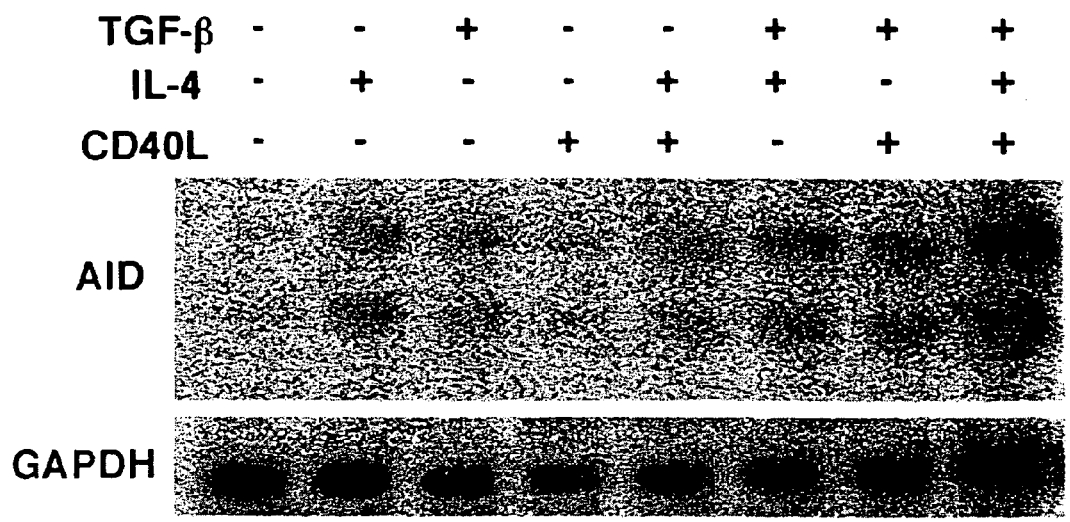

FIG. 15 a photograph showing expression state for mRNA of AID in mouse B cell clone CH12F3-2 stimulated with cytokine in various combinations, analyzed by Northern blotting.

Figure 16:
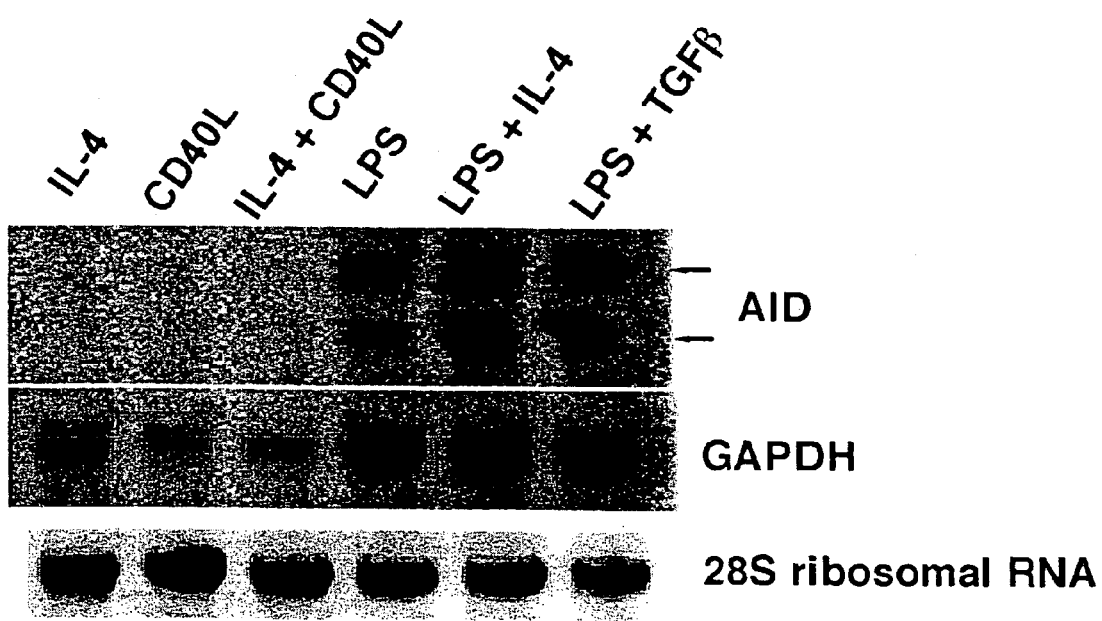

FIG. 16 shows a photograph indicating expression state for mRNA of AID in mouse spleen B cells, stimulated with stimulants in various combinations, analyzed by Northern hybridization method.

Figure 17:
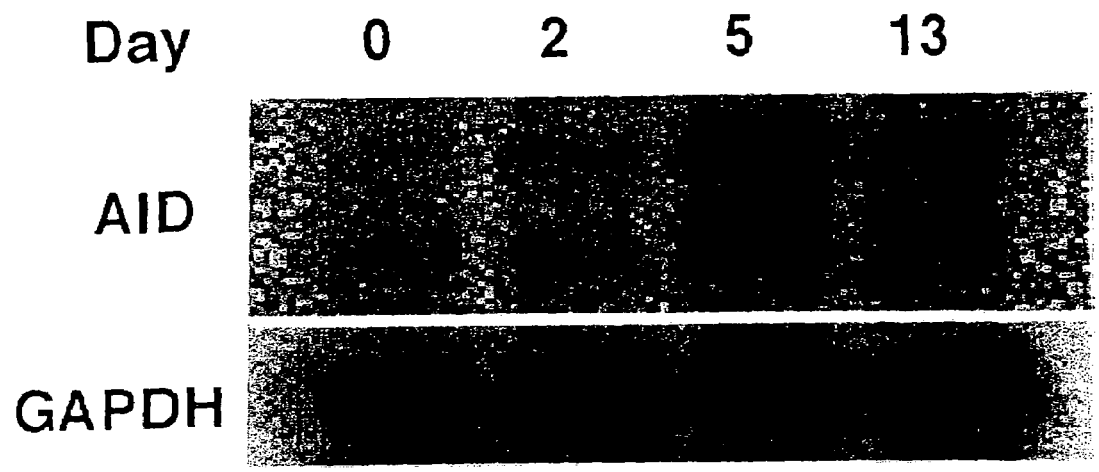

FIG. 17 is a photograph indicating expression state for mRNA of AID in splenocytes derived from mice immunized with sheep red blood cells, analyzed by Northern blotting analysis.

Figure 18:
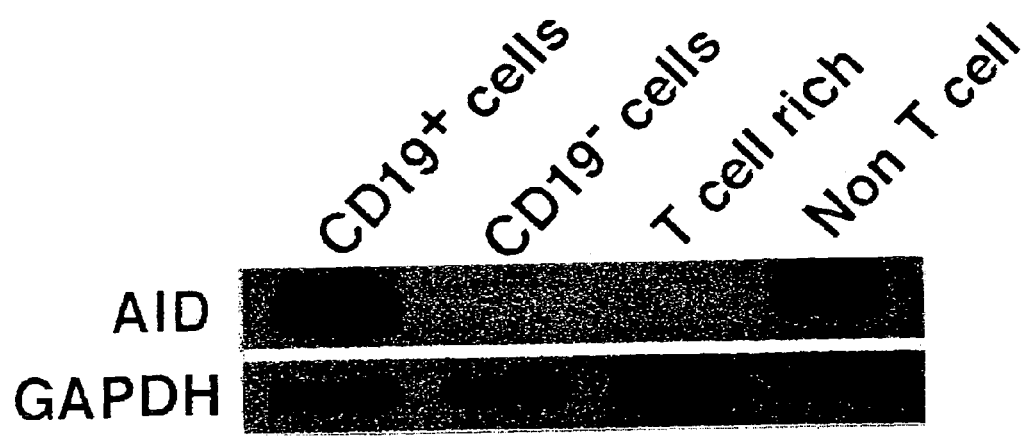

FIG. 18 shows expression state for mRNA of AID in splenocytes derived from mice immunized with sheep red blood cells, analyzed by RT-PCR.

FIG. 19 is a photograph indicating localization of expression for AID mRNA in splenocytes derived from a normal mouse or a mouse immunized by sheep red blood cells, specifically, analyzed by in situ hybridization.

Figure 19A:
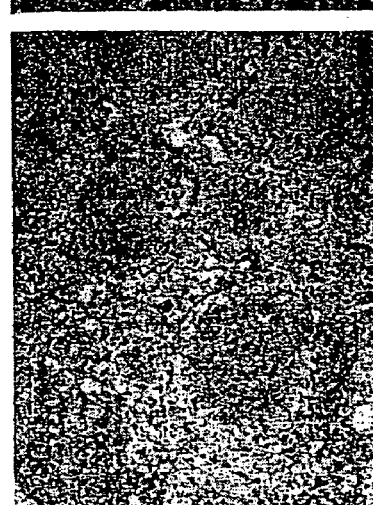
Figure 19B:
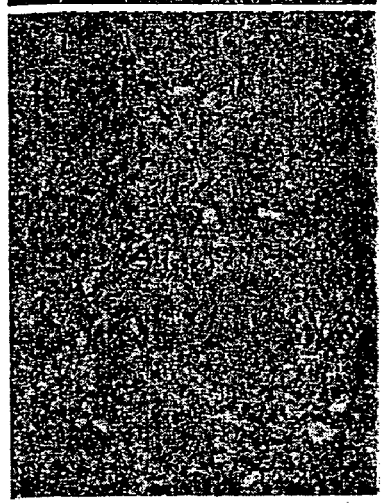
Figure 19C:
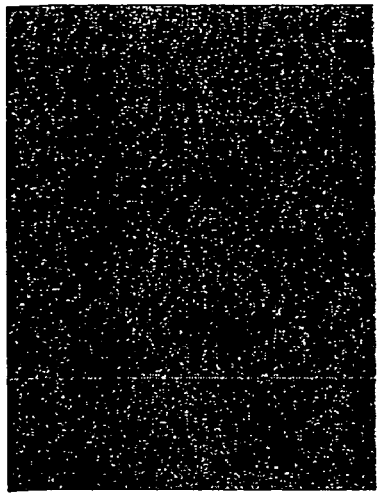
Figure 19D:
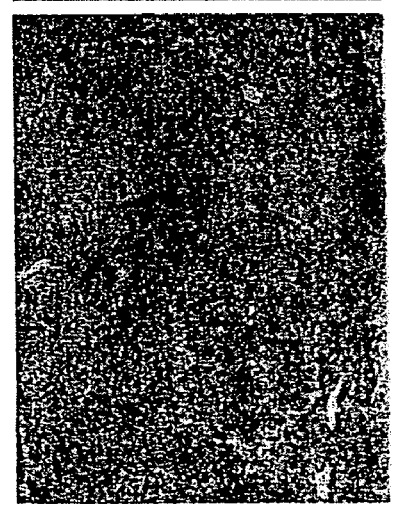

FIGS. 19(A) and (D) indicate the result in the hybridization using a sense AID probe. FIGS. 19(B) and (E) show localization for AID mRNA expression in hybridization using an antisense-AID probe. FIGS. 19(C) and (F) show localization of germinal center in staining test by FITC-labeled PNA. FIGS. 19(A), (B), and (C) indicate the result in the test using spleen tissues derived from normal mouse (before the immunization of sheep red blood cells). FIGS. 19(D), (E), and (F) show the results of the examination using spleen tissue slices prepared 5 days after immunizing a mouse with sheep red blood cells.

FIG. 20 is a photograph showing the localization of expression for AID mRNA in spleen tissue and payer's patch tissue, respectively, derived from a normal mouse or from a mouse immunized with sheep red blood cells, respectively, analyzed by in situ hybridization.

FIGS. 20(A), (D), and (G) show the results in the hybridization using a sense AID probe. FIGS. 20(B), (E), and (H) show the localization of the expression for AID mRNA in hybridization using an antisense AID probe. FIGS. 20(C), (F), and (I) show the localization of germinating center in the staining test by FITC-labeled PNA. FIGS. 20(A), (B), and (C) show the result of the examination using spleen tissues derived from a normal mouse (before immunization by sheep red blood cells). FIGS. 20(D), (E), and (F) show the results of the examination using spleen tissue slices prepared 5 days after immunization of a mouse with sheep red blood cells. FIGS. 20(G), (H), and (I) show the results of test using payer's patch prepared 5 days after the immunization of a mouse with sheep red blood cells.

Figure 21:
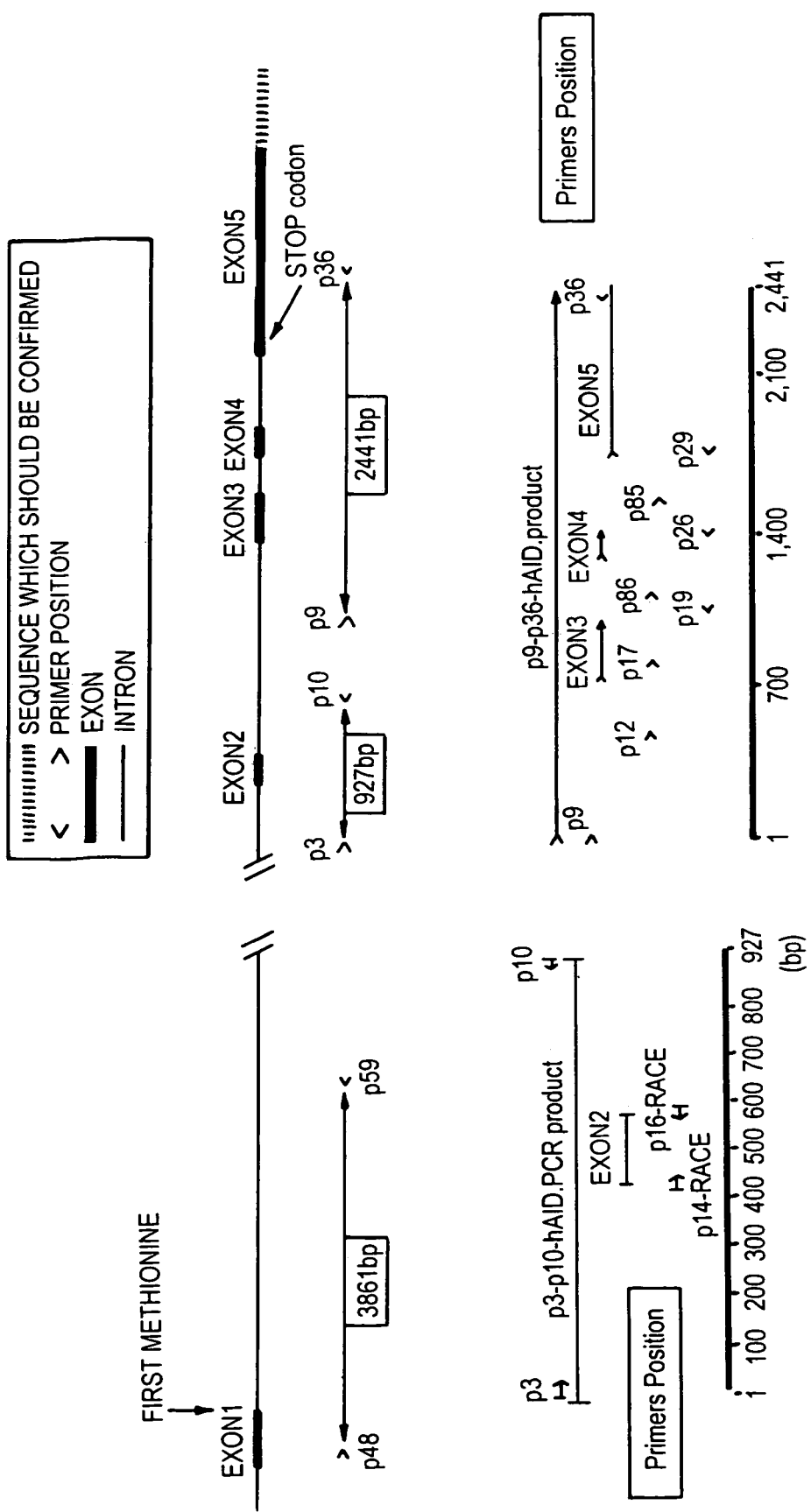

FIG. 21 schematically shows relative locations of partial nucleotide sequences of human genomic DNA coding human AID protein, which was amplified by PCR using various pairs of primers.

FIG. 22 schematically shows a degree of homology between an amino acid sequence of mouse AID protein (SEQ ID NO:2) and that of human AID protein (SEQ ID NO:8). The parts with a closed box are cytidine and deoxycytidylate deaminase zinc-binding region which is an AID protein active region.

FIG. 23 schematically shows the structure of human genomic DNA including a gene coding human AID protein. One to five shows exon 1, exon 2, exon 3, exon 4, and exon 5, respectively.

Figure 24:
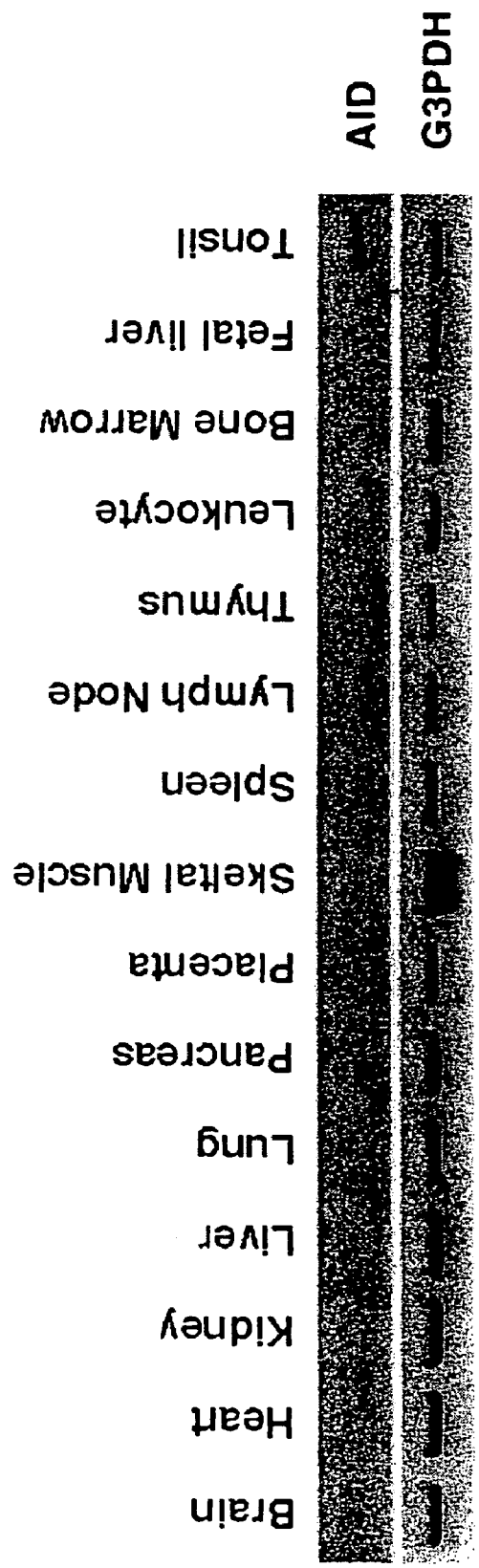

FIG. 24 is a photograph indicating the expression state for human AID mRNA in various types of human tissues, analyzed by RT-PCR.

Figure 25:
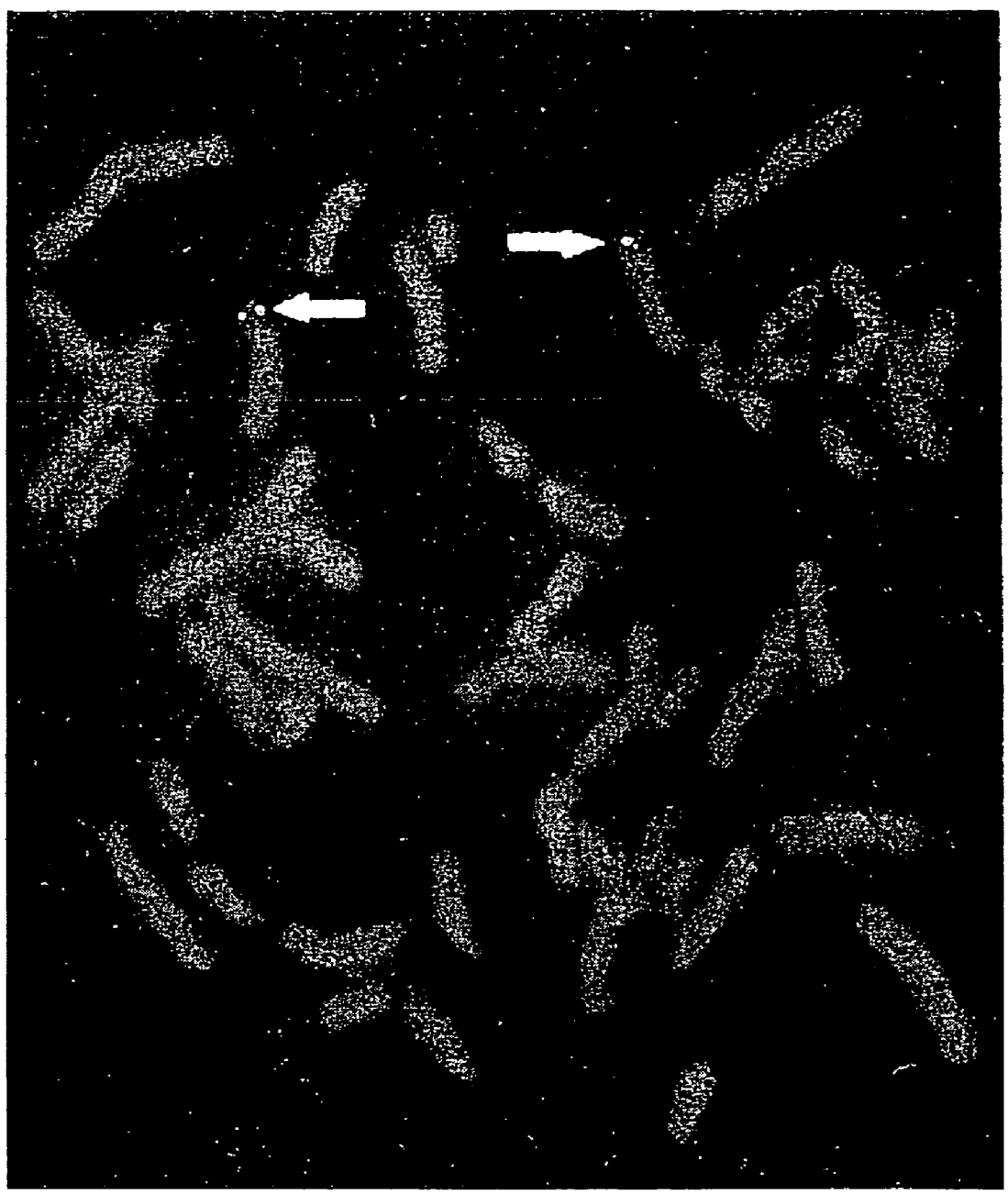

FIG. 25 is a photograph indicating a location (localization) of human AID gene on human chromosome, analyzed by Fluorescence in situ hybridization (FISH) method.

Two points at the tips of arrows show 12p13, where the human AID gene is located.

Like reference symbols in the various drawings indicate like elements.

DETAILED DESCRIPTION OF THE INVENTION

The invention is illustrated in detail by the following Examples, but is not restricted to the embodiments described in the Examples.

EXAMPLE 1

Culture of Mouse B Cell Clone CH12F3-2 and Confirmation of Properties

Mouse B cell clone CH12F3-2 that undergoes class switch recombination (CSR) from IgM to IgA, several hours after stimulation with IL-4, TGF-β, and CD40L, previously isolated by the present inventors, was cultured in the same manner as in the previous report (Immunity, 9:1–10, 1998; Curr. Biol., 8:227–230, 1998; Int. Immunol, 8:193–201, 1996).

When CH12F3-2 cells were stimulated with IL-4, TGF-β, and CD40L, a circular DNA including an S region (switch region) looped out by class switch recombination was detected several hours after the stimulation.

The following manipulation was conducted according to the previously reported method (Curr. Biol., 8:227–230, 1998).

CH12F3-2 B cells, either stimulated by IL-4, TGF-β, and CD40L or unstimulated, were cultured for 6 hours in the presence or absence of cycloheximide (200 ng/ml) which is a protein synthesis inhibitor, respectively. Genomic DNA was extracted from each cell, and PCR was conducted with the DNA as a template following standard methods to amplify circular DNA including an Sμ sequence and an Sα sequence. PCR was conducted using pairs of primers, αF1 and μR3, or αF1 and μR3.

As a control, genomic DNA encoding glyceraldehyde-3-phosphate dehydrogenase (GAPDH) was amplified by PCR.

Figures 1A, 1B:
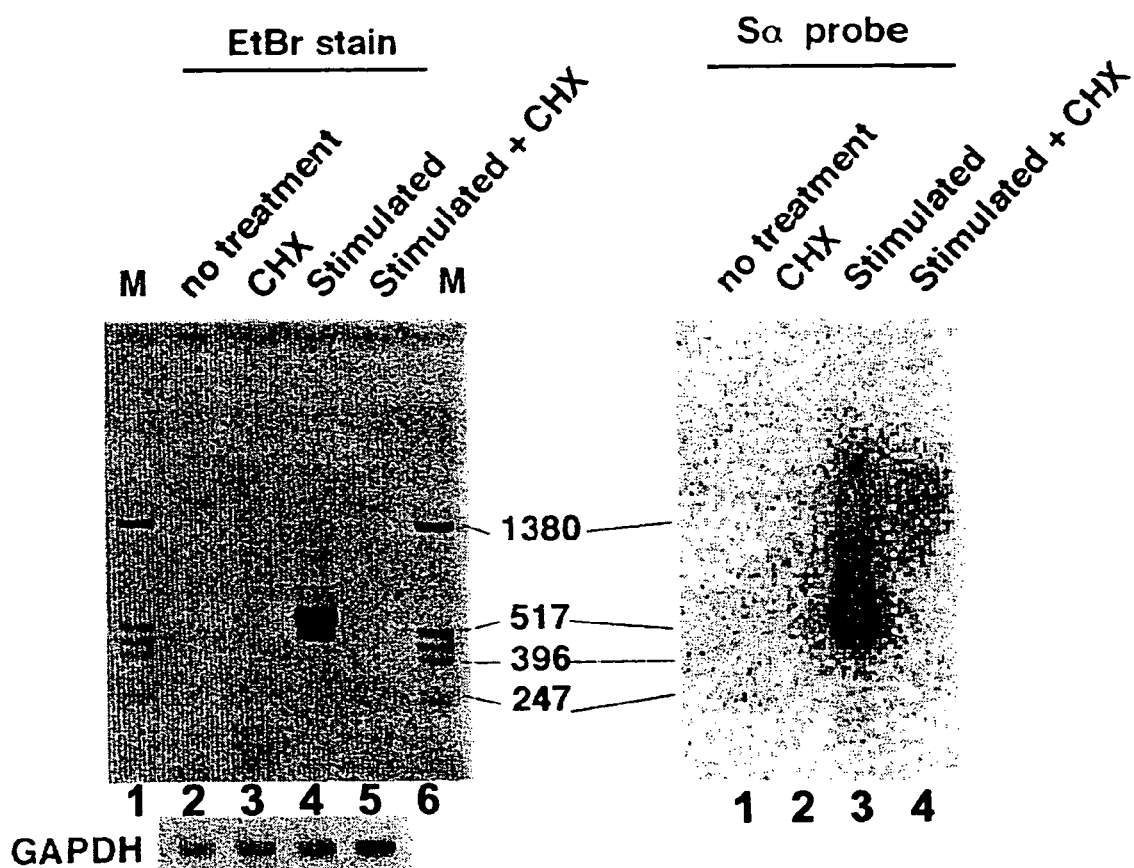
FIG. 1 is a pair of photographs which show the production of DNA including an Sα sequence looped out by class switch recombination in mouse B cell clone CH12F3-2 cultured under various conditions.

The PCR products were subjected to gel electrophoresis and ethidium bromide staining. FIG. 1(a) and FIG. 2(a) show the results.

To confirm the presence or absence of the amplification of a circular DNA including the looped-out S region, Southern hybridization was conducted against the PCR products using a mouse Sα region gene as a hybridization probe, according to standard methods (L. Sambrook E. F., Tom Maniatis., Second edition, Ed. Molecular Cloning (Nolan, C., Ed.) Cold Spring Harbor, 1989). A 1,155 bp DNA fragment obtained by digesting 10 kb EcoRI cleaved fragment IgH703 with Hind III and EarI was used as an Sα gene (Genbank #D11468, DNA No. 1993-3148) (J, Biol. Chem., Vol. 268, p. 4651–4665). FIGS. 1(b) and 2(b) show the results.

It has been shown that mouse B cell CH2F3-2 produces the looped-out DNA containing the Sα sequence with the class switch recombination after stimulation with cytokines, and the production of the DNA is inhibited by the presence of cycloheximide. This result suggested that the occurrence of class switch recombination of an immunoglobulin gene requires de novo protein synthesis in the very early stages after stimulation, and that protein synthesis is deeply involved in the induction of class switch recombination.

EXAMPLE 2

Identification of a Gene Whose Expression is Improved in Mouse B Cell CH12F3-2 Stimulated by Cytokines A gene which is presumably expressed in the early stage after mouse B cell clone CH12F3-2 is stimulated, and presumably plays a role in introducing class switch recombination of an immunoglobulin gene, was attempted to be isolated from CH12F3-2 cells by the suppression subtract hybridization (SSH) (Proc. Natl. Acad. Sci. USA, 93:6025–6030, 1996; Anal. Biochem., 240:90–97, 1996) using the inhibitory PCR effect (Nucleic Acids Res., 23:1087–1088, 1995).

A cDNA library necessary for subtraction cloning was prepared using a PCR-Select Subtraction Kit (CLONTECH, Catalogue NO: K1804-1) by following the instruction manual supplied with the kit.

PolyA$^+$ RNA was isolated from each of: mouse B cell clone CH12F3-2 stimulated with IL-4, TGF-β and CD40L for 5 hours, the same cells stimulated with the cytokines for 12 hours, and cells which were not stimulated, following the reported method (Nucleic Acids Res., 26:911–918, 1998) and treated with DNaseI to eliminate any contaminating genomic DNA. Then cDNA was prepared based on each polyA$^+$ RNA sample using reverse transcriptase according to the standard method. Each cDNA prepared from mouse B cell clone CH12F3-2, treated with the above cytokines for 5 or 12 hours, was mixed in equimolar amounts to be used as a tester cDNA. On the other hand, cDNA derived from unstimulated cells was used as a driver cDNA.

Subtraction was conducted by adding the driver cDNA into the tester cDNA according to the above-referenced previous report and the kit instruction manual. The efficiency of subtraction was monitored by adding a small amount (1:1000 mole ratio) of Φ X174 phage DNA cleaved at the restriction enzyme site Hae III, as a control, into the tester cDNA. After the subtraction, the phage DNA was concentrated to a mole ratio of about 100 times.

The subtracted cDNA was cloned into the T-vector (Promega) according to the standard method to prepare a plasmid library. In the same manner as in the previous report, 2000 colonies in the library were screened by the differential hybridization method (Nucleic Acids Res., 26:911–918, 1998; Medical immunity, 29:17, p. 451–459, 1997). Each of the above tester cDNA and driver cDNA was radiolabeled to be used for hybridization. Clones including Φ X174 phage DNA were selected by hybridizing Φ X174 phage DNA with a replicant filter.

One hundred fifteen clones emitting a stronger signal than the radio-labeled driver cDNA probe against radiolabeled tester cDNA probe were identified and a nucleotide sequence of each clone was determined by using a DNA sequencer.

Northern blotting was conducted against mRNA obtained from mouse B cell clone CH12F3-2 stimulated with IL-4, TGF-β and CD40L or the same cell line unstimulated, using the radio-labeled DNA inserted into the each clone as a probe, according to the standard method (L. Sambrook, E. F., Tom Maniatis., Second edition, Ed. Molecular Cloning (Nolan, C., Ed.), Cold Spring Harbour, 1989). As a result, the enhanced expression corresponding to the stimulation with the above cytokines was observed in 23 out of 115 clones. Gene fragments coding 7 different types of proteins, including genes coding 3 kinds of known proteins and 4 kinds of novel proteins were found to be inserted into the 23 clones. Specifically, the expression of the 7 kinds of genes was found to be enhanced in mouse B cell clone CH12F3-2 by the stimulation with IL-4, TGF-β and CD40L.

<The Known Proteins>
ABCD-1/MDC (8 clones)
IFNγ receptor (2 clones)
I-a (MHC class II) (1 clone)
<Novel Proteins>
23C9 (3 clones)
15B 11 (7 clones)
8B9 (1 clone)
16A9 (1 clone As it has been known that the expression of the above I-a gene and ABCD/MDC gene is enhanced by stimulating mouse spleen B cell with IL-4 and CD40L, it was confirmed that the subtraction cloning was effectively conducted (J. Exp. Med., 188:451–463, 1998; Immunity, 5:319–330, 1996).

EXAMPLE 3

Expression of mRNA for a Novel Protein 23C9 in Mouse B Cell Clone CH12F3-2

The degree of enhanced expression of the gene coding for a novel protein 23C9 in mouse B cell clone CH12F3-2 stimulated with IL-4, TGF-β and CD40L was analyzed according to the standard method (L. Sambrook, E. F., Tom Maniatis., Second edition, Ed. Molecular Cloning (Nolan, C., Ed.), Cold Spring Harbour, 1989) by Northern blotting.

Mouse B cell clone CH12F3-2 was cultured in the presence of one of the following regents for 12 hours.

(1) IL-4, TGF-β and CD40L only.
(2) Cycloheximide which is a protein synthesis inhibitor (200 ng/ml), only
(3) IL-4, TGF-β and CD40L as well as Cycloheximide (200 ng/ml)

Northern blotting was conducted against mRNA (10 μg for each group) obtained in the same manner as previously reported (Nucleic Acid Res., 26:911–918, 1998) from each group of treated cells using a radio-labeled cDNA fragment (1,020 bp) coding for a novel protein 23C9, obtained in the above Example, according to the standard method (L. Sambrook, E. F., Tom Maniatis., Second edition, Ed. Molecular Cloning (Nolan, C., Ed.), Cold Spring Harbour, 1989).

As a control experiment, Northern blotting was conducted for mRNA derived from B cell clone CH12F3-2 cultured without any one of the above cytokines, or cycloheximide.

The amount of mRNA to be electrophoresed was adjusted using the amount of mRNA for glyceraldehyde-3-phosphate dehydrogenase (GAPDH) as an index. DNA amplified by RT-PCR using a GF primer and a GR primer was used as a probe for blots of GAPDH mRNA (Location of nucleotides: 566–1016, Genbank U5299) (Immunity, 9:1–10, 1998).

FIGS. 3 and 4 show the results.

The expression of mRNA for a novel protein 23C9 was extremely strong in mouse B cell clone CH12F3-2 stimulated with IL-4, TGF-β and CD40L, while the expression in unstimulated cells was extremely weak. Expression of the mRNA in the stimulated cells was inhibited by the presence of a protein synthesis inhibitor. Moreover, in the stimulated cells, two bands indicating the expression of mRNAs comprising different nucleotide lengths were detected.

Expression of mRNA for a novel protein 23C9 in each of the following mouse cell lines, which do not originally undergo class switch recombination, was examined by Northern blotting in the same manner as in the above.

B cell lines (lyD9, BA/F3, 70Z/3, WEHI231); T cell lines (EL-4, 2B4); myeloma cell lines (X63, HEHI-3); fibroblast lines (L929, NIH3T3,); and other cell lines (F2, P815, ST2).

The expression of mRNA for the novel protein 23C9 was not observed in any of these cells.

EXAMPLE 4

Cloning of a Full Length cDNA Encoding a Novel Protein 23C9

Four different positive clones were obtained by screening a cDNA library (Nucleic Acids Res., 26:911–918, 1998) prepared from mouse B cell clone CH12F3-2 stimulated with IL-4, TGF-β, and CD40L, using a cDNA fragment (1,020 bp) encoding the novel protein 23C9, obtained in the above Example, as a probe. The nucleotide sequence of each clone was determined by using a DNA sequencer according to the standard method.

One clone comprises a 1.2 kb nucleotide length and a single reading frame (ORF) with 1 polyadenylation site. The other 3 clones comprise a 2.4 kb nucleotide length and 2 polyadenylation sites. The nucleotide sequence of the first 1.2 kb at the 5' end of the latter clones was identical to that of the nucleotides of the 1.2 kb DNA in the former (SEQ ID NO:1).

Two different mRNA transcripts detected in Northern blotting in the above Example (FIGS. 3 and 4) were predicted to correspond to transcripts for each of the above 1.2 kb and 2.4 kb, transcribed until the polyA site at the 3' end and the polyA site at the 5'end.

A cDNA fragment encoding the novel protein 23C9 used as a probe in the above (1,020 bp) was found to have a nucleotide sequence of from 847 to 1866 in the full length cDNA of 23C9.

A nucleotide sequence near a first initiation codon in each cDNA was fit to Kozak's rule (Nucleic Acids Res., 15:8125–8148, 1987). In the 2.4 kb cDNA, ATTTA, which is a motif capable of mediating quick degradation of mRNA (Blood, 83:3182–3187, 1994), was present in the 2 sites in the 3' untranslated region.

An open reading frame (ORF) of cDNA encoding a novel protein 23C9 consisted of 198 amino acids with the expected molecular weight of about 24 kDa (SEQ ID NO:2). As a result of homology searching with known proteins in a database, it was discovered that thean amino acid sequence of the ORF of the novel protein 23C9 comprised 34% amino acid homology with the apolipoprotein B mRNA editing enzyme, catalytic polypeptide-1 (APOBEC-1) (Science, 260:1816–1819, 1993; J. Biol. Chem., 268:20709–20712. 1993). GenBank and EMBL were used as the DNA data bases. SwissPlot was used as the protein database. The BLAST program (J. Mol. Biol., 215:403–410, 1990) and the FASTA program (Proc. Natl. Acad. Sci. USA., 85:2444–2448 1988) were used to search the databases.

FIG. 5 shows an amino acid sequence of the ORF of the novel protein 23C9 and an alignment between the sequence and that of mouse APOBEC-1 amino acid sequence.

Motif searching online using PROSITE (Nucleic Acids Res., 11:2013–2018, 1992) indicates that the APOBEC-1-like novel protein 23C9 comprises a cytidine/deoxycytidine deaminase motif which is conserved in the amino acid sequences of proteins belonging to the cytosine nucleoside/nucleotide deaminase family, which is a large family and is an activation site of a deaminase activity. The cytosine nucleoside/nucleotide deaminase family is classified into RNA editing deaminases, cytidine/deoxycytidylate deaminases, and CMP/dCMP deaminases based on substrate specificity and homology in the activation sites (Cell, 81:187–195, 1995).

A phylogenetic tree was prepared based on the alignment of regions in APOBEC-1, which is an RNA editing deaminases, cytosine nucleoside deaminase, cytosine nucleotide deaminases, and the cytidine deaminase motif in the novel protein 23C9. The sequences of the known proteins used for the comparison were obtained from GenBank, as follows.

Human derived nucleoside deaminase: L27943
    Mouse derived nucleoside deaminase: AA388666
    S. subtilis derived nucleoside deaminase: U18532
    E. coli derived cytidine deaminase: X63144
    Rabbit derived APOBEC-1: U10695
    Human derived APOBEC-1: L25877
    Rat derived APOBEC-1: U10695
    Mouse derived APOBEC-1: U21951

T2/T4 phage derived nucleotide deaminase: J05172

Human derived nucleotide deaminase: L12136
    S. cerevisiae derived nucleotide deaminase: U10397

FIG. 6 shows the result. The cytidine deaminase motif in the novel protein 23C9 was more closely related to a subgroup of RNA editing deaminases than to subgroups of nucleoside deaminase and nucleotide deaminase.

On the other hand, a leucine-rich region existing at the C-terminus of APOBEC-1 is thought to be important for protein-protein interaction (Proc. Natl. Acad. Sci. USA., 91:8522–8526, 1994; J. Biol. Chem., 269:21725–21734, 1994). The novel protein 23C9 also comprised a leucine-rich region at the C-terminus. Four leucines in the region of 23C9 were conserved in the leucine rich regions of APOBEC-1 in rabbit, rat, mouse and human.

It has been known that Phe66, Phe87, His61, Glu63 and Cys93 are essential for binding of APOBEC-1 to RNA, and all these amino acid residues were conserved in the primary structure of 23C9 (Trends Genet., 12:418–424, 1996; Cell, 81:187–195, 1995; J. Biol. Chem., 270:14768–14775 1995; J. Biol. Chem., 270:14762–14767, 1995). From this fact, 23C9 protein is predicted to comprise an RNA editing deaminase activity.

Moreover, cytidine deaminases derived from APOBEC-1 and E. coli (ECCDA) are known to comprise a pseudoactive site domain at the C-terminus, and the 23C9 protein also comprises a pseudoactive site domain, the same as is in the APOBEC-1. This indicates that 23C9 protein is more closely related to APOBEC-1 and ECCDA than to deaminase proteins in the other groups.

From these facts, the novel protein 23C9 was named activation-induced cytidine deaminase (AID). The novel protein 23C9 was called AID hereafter.

EXAMPLE 5

Preparation of the AID-GST Fusion Protein

The cDNA coding the full length AID cloned in the above Example was amplified by PCR with a pair of primers, AID-138 (SEQ ID NO:3) and AID-161 (SEQ ID NO:4), a pair of primers, AID-118 (SEQ ID NO:5) and AID-119 (SEQ ID NO:6), using Taq Polymerase following the standard method. As there is an intron between AID-118 and AID-119, a PCR product derived from AID genomic DNA can be easily distinguished.

The obtained PCR product was subcloned into the pGEX4T1 vector (Pharmacia) according to the standard method. A nucleotide sequence of the vector was determined and the absence of point mutations derived from the use of Taq polymerase in the full length AID cDNA cloned into the vector was confirmed.

E. coli DH5α was transformed with the vector according to the standard method. The obtained transformants were cultured, and a full length AID cDNA was expressed as a fusion protein with glutathione S-transferase (GST). The AID-GST fusion protein was extracted in the same manner as in the previous report, and purified using glutathione agarose affinity chromatography (J. Biol. Chem., 270:14768–14775 1995).

The molecular weight of the purified AID-GST fusion protein was analyzed by following the standard method using 10% SDS-PAGE and silver staining. A protein extracted from wild type E. coli DH5a was used as a control. FIG. 7 shows the results.

As expected, the fusion protein was detected as a band comprising a molecular weight of about 49 kDa. Minor bands detected under about 49 kDa were thought to be decomposed proteins, frequently generated in the purification process in general.

A molecular weight of the purified AID-GST fusion protein was analyzed by the Western blotting according to the standard method (Genomics, 54:89–98, 1998). Anti-AID protein antibody to be used for the assay was prepared by immunizing a commercial rabbit with multiple antigen peptides including synthetic peptides corresponding to amino acids Nos. 116 to 132 of the AID protein of the present invention (Proc. Natl. Acad. Sci. USA., 85:5409, 1988).

FIG. 8 shows the results.

EXAMPLE 6

Cytidine Deaminase Activity of the AID Protein

A cytidine deaminase activity of AID was measured by the same method as in the previous report (J. Biol. Chem. 270:14768–14775, 1995).

The purified AID-GST fusion protein prepared in the above (2, 4, 6, 8, 10, 20, 40, 60, 100, 200, 300, 400, and 600 ng) was incubated in the buffer (pH 7.5, the total amount 10 μl) containing 45 mM Tris with 3.3 μCi [$^3$H] deoxycytidine (24.8 Ci/mmol, DuPont) and 250 μM cytidine for 2 to 4 hours. The reaction was terminated by adding deoxycytidine (2 μl of 10 μg/ml) and deoxyuridine (2 μl of 10 μg/ml). Insoluble substances were removed by centrifugation, and the reaction mixture (4 μl) was subjected to the polyethylene imine-cellulose thin layer chromatography plate (VWR). The plate was developed in isopropyl alcohol/10% HCl (7:2 v/v). The plate was exposed to ultraviolet light (254 nm) for visualization and bands corresponding to deoxycytidine and deoxyuridine were collected, and added to Ultima Gold scintillation solution to be quantified by liquid scintillation photometer (Packard)

FIG. 9 shows the results. The AID protein showed a concentration-dependent cytidine deaminase activity.

The inhibitory effect of tetrahydrouridine (THU; 0 to 40 μM) (Calbiochem, USA), which is an inhibitor specific to cytidine deaminase, on the cytidine deaminase activity in the AID-GST fusion protein (300 ng) was measured by the same method described above.

FIG. 10 shows the results. The cytidine deaminase activity of AID protein was inhibited depending on the concentration of THU.

The inhibitory effect of 1,10-o-phenanthroline (0 to 20 mM), which is a zinc-chelating agent, and its inactive isomer 1,7-o-phenanthroline (0 to 20 mM), on the cytidine deaminase activity of the AID-GST fusion protein was measured in the same manner as described below.

FIG. 11 shows the results. The cytidine deaminase activity of AID protein was inhibited by 20 mM 1,10-o-phenanthroline by about 91%. 1,7-o-phenanthroline, which is the inactive isomer, only inhibited about 13%. These results indicate that the AID protein is a zinc-dependent cytidine deaminase, similar to APOBEC-1.

EXAMPLE 7

Avidity of AID Protein with AU-Rich RNA

A recombinant APOBEC-1 binds to AU-rich RNA (Trends Genet., 12:418–424, 1996; Cell, 81:187–195, 1995; J. Biol. Chem., 270:14768–14775, 1995; J. Biol. Chem., 270:14762–14767, 1995), and progresses RNA editing of apoB in the presence of chicken extract including co-factor.

Since the AID protein has a functional cytidine deaminase activity as well as a structural similarity to APOBEC-1, to examine RNA editing activity in the AID protein, avidity to AU-rich RNA (5-AU) and apoB RNA (which are RNA substrates for APOBEC-1) was examined.

The AID protein did not show avidity to AU-rich RNA (5-AU) in the gel retardation assay. In an in vitro apoB RNA assay, conversion from cytidine (C) to uridine (U) was not observed.

EXAMPLE 8

Expression Distribution of AID mRNA in Tissues

The expression of AID mRNA in each tissue was examined by Northern blotting according to the standard method (L. Sambrook, E. F., Tom Maniatis., Second edition, Ed. Molecular Cloning (Nolan C., Ed.), Cold Spring Harbour, 1989; Experimental Medicine, Suppl., "Genetic Engineering Hand Book", published by Yodosha, p. 133–140, 1992).

PolyA$^+$ RNA (2 μg each) obtained from cells derived from each tissue in mice (muscle, spleen, lung, heart, lymph node, brain, kidney, thymus, testis, liver) according to the previous report (Nucleic Acids Res., 26:911–918, 1998) was used as a sample. Radiolabeled cDNA fragments (1,020 bp) encoding AID (23C9) obtained in the previous Examples was used as a probe for blotting polyA$^+$ RNA.

As a control, mRNA of glyceraldehyde-3-phosphate dehydrogenase (GAPDH) was blotted in the same manner. As a probe for blotting GAPDH mRNA, DNA amplified by PCR using GP primer and GR primer was used. (Nucleotide location: 566–1016, Genbank, U52599) (Immunity, 9:1–10, 1988).

FIG. 12 shows the results.

The results show that AID mRNA was strongly expressed in mesenteric lymph node. In addition, weak expression was observed in spleen.

EXAMPLE 9

Expression of AID mRNA in Various Lymphatic Tissues

The expression of AID mRNA in each lymphatic tissue was analyzed by RT-PCR according to the standard method (Immunity, 9:1–10, 1998).

cDNA was prepared according to the standard method using polyA$^+$ RNA obtained from cells derived from various lymphatic tissues (Payer's patch, mesenteric lymph node, axillary lymph node, spleen, bone marrow, thymus) in the same manner as in the previous report (Nucleic Acids Res., 26:911–918, 1998), for mRNA as a sample, as a template. AID cDNA and GAPDH cDNA were amplified using the obtained cDNA as a template. A first pair of primers, AID-138 (SEQ ID NO:3) and AID-161 (SEQ ID NO. 4) as above, a second pair of primers AID-118 (SEQ ID NO:5) and AID-119 (SEQ ID NO:6), and Taq polymerase were used for PCR of AID cDNA. As there is an intron between AID-118 and AID-119, a PCR product derived from the AID genomic DNA sequence can be easily distinguished.

FIG. 13 shows the results.

AID cDNA was detected in all lymphatic tissues except for thymus. In particular, obvious expression was observed in peripheral lymphatic organs, such as lymph-node or Payer's patch. On the other hand, expression in primary lymphatic organs was weak in comparison with that in the peripheral lymphatic organs.

EXAMPLE 10

Expression of AID mRNA Over Time in Activated Mouse B Cell Clone CH12F3-2

Expression of AID mRNA over time in activated mouse B cell clone CH12F3-2 stimulated with IL-4, TGF-β, and CD40L for 0 to 60 hours was analyzed by Northern blotting according to the standard method (L. Sambrook, E. F., Tom Maniatis., Second edition Ed. Molecular Cloning (Nolan, C., Ed.) Cold Spring Harbor, 1989).

Mouse B cell clone CH12F3-2 was cultured in the presence of IL-4, TGF-β, and CD40L for various periods (0, 3, 5, 12, 24, 36, 48, or 60 hours).

Northern blotting was conducted against mRNA (10 μg in each group) obtained from each culture group in the same manner as in the previous report (Nucleic Acids Res., 26:911–918, 1998) using a radiolabeled cDNA fragment encoding AID (23C9) obtained in the previous Examples, as a probe, according to the standard method (L. Sambrook, E. F., Tom Maniatis., Second edition Ed. Molecular Cloning (Nolan, C., Ed.). Cold Spring Harbor, 1989).

The amount of mRNA to be gel-electrophoresed was adjusted by using mRNA of GAPDH as an index. DNA amplified by RT-PCR using a GF primer and a GR primer was used as a probe for blotting GAPDH mRNA (Nucleotide location: 566–1016, Genbank U52599) (Immunity, 9:1–10, 1998).

FIG. 14 shows the results.

It was shown that the expression of AID mRNA in mouse B cell clone CH12F3-2 was too low to be detected without stimulation by cytokines, but expression was initiated 3 hours after stimulation by cytokines (described in the above), was maximum 12 hours after stimulation (more than about 15 times), and was gradually decreased from 48 hours after the stimulation.

EXAMPLE 11

Cytokine Specificity in the Induction of Expression of AID mRNA in Mouse B Cell Clone CH12F3-2

Cytokine specificity in inducing expression of AID mRNA in mouse B cell clone CH12F3-2 was analyzed by Northern blotting according to the standard method (L. Sambrook, E. F., Tom Maniatis., Second edition Ed. Molecular Cloning (Nolan, C., Ed.), Cold Spring Harbour, 1989).

Mouse B cell clone CH12F3-2 was cultured in the presence of various combinations of cytokines (one or more selected from IL-4, TGF-β, and CD40-L) for 12 hours. Northern blotting was conducted against mRNA (10 μg in each group) obtained from each culture group in the same manner as in the previous report (Nucleic Acids Res., 26:911–918, 1998) using a radio-labeled cDNA fragment (1,020 bp) coding AID (23C9) obtained in the previous Example, according to the standard method (L. Sambrook, E. F., Tom Maniatis., Second Ed. Molecular Cloning (Nolan, C., Ed.). Cold Spring Harbor, 1989).

The amount of mRNA to be gel-electrophoresed was adjusted using mRNA of GAPDH as an index. DNA amplified by RT-PCR using a GF primer and a GR primer was used as a probe for blotting GAPDH mRNA (Nucleotide location: 566–1016, Genbank U52599) (Immunity, 9:1–10, 1998).

FIG. 15 shows the results.

Induction of AID-mRNA expression by solely any one kind of cytokine was small. On the other hand, when 3 kinds of cytokines as described above were used at the same time, maximal induction of AID-mRNA expression was observed.

As described in the above Example 3, because induction of AID mRNA expression was inhibited by cycloheximide, which is an inhibitor of protein synthesis, it is hypothesized that enhanced expression of AID mRNA requires de novo protein synthesis.

EXAMPLE 12

Induction of AID mRNA Expression in Spleen B Cells by Stimulation

The presence or absence of expression of AID mRNA after stimulation which may activate B cells and induce class switch recombination of immunoglobulin was examined.

Spleen B cells were obtained from BALB/c mouse (6 to 12-week old, Shimizu Experimental Materials (SLC)) and purified according to the standard method. Dead cells and cell fragments were removed by Ficoll density gradient centrifugation after the process of removing T cells. The purified spleen B cells were cultured for 4 days in the presence of a stimulus in various combinations (one or more selected from IL-4, TGF-β, CD40L, and LPS (lipopolysaccharide) in the same manner as in the previous report (Nucleic Acids Res., 26:911–918, 1998). LPS derived from *Salmonella* typhosa (50 μg/ml, Sigma) was used.

Northern blotting was conducted against mRNA (15 μg in each group) obtained from each culture group in the same manner as in the previous report (Nucleic Acids Res., 26:911–918, 1998) using a radio-labeled cDNA fragment encoding AID (23C9) obtained in the previous Example, according to the standard method (L. Sambrook, E. F., Tom Maniatis., Second edition Ed. Molecular Cloning (Nolan, C., Ed.) Cold Spring Harbor, 1989).

The amount of mRNA to be gel-electrophoresed was adjusted by using mRNA of GAPDH and 28S ribosomal RNA as an index. DNA amplified by RT-PCR using a GF primer and a GR primer was used as a probe for blotting GAPDH mRNA (Nucleotide location: 566-1016, Genbank U52599) (Immunity, 9:1–10, 1998).

FIG. 16 shows the results.

The enhanced expression of AID mRNA by stimulation with LPS only, LPS+IL-4, or LPS+TGF-β was observed in normal mouse spleen B cells.

EXAMPLE 13

Induced Expression of AID mRNA in vivo

It was examined whether the induction of AID mRNA expression by various stimulations in vitro would also occur in vivo.

BALB/c mice (6 to 12-week old, five individuals in each group, SLC) were immunized by intraperitoneally administering sheep red blood cell (SRBC) ($1 \times 10^8$ cells, Cosmo Bio.). In the living body immunized by SRBC, it has been known that clonal expansion and germinal center formation occur after the immunoresponse, and class switch recombination of an immunoglobulin gene and affinity maturation are caused.

PolyA$^+$ RNA was prepared from splenocytes isolated from spleen excised from each individual before (day 0) and after (day 2, 5 and 13) the immunization.

The polyA$^+$ RNA (2 μg each) was subjected to Northern blotting using the radiolabeled cDNA fragment (1,020 bp) encoding AID (23C9) as a probe in the same manner as the above Examples. The amount of mRNA to be gel-electrophoresed was adjusted using mRNA of GAPDH as an index in the same manner as in the above Examples.

FIG. 17 shows the results.

The minimum amount of expressed AID mRNA was detected before immunization of SRBC (day 0), however, a significant enhancement of expression (about 4 to 5 times) was observed day 5 and day 13 after the immunization.

Moreover, to analyze in which cell type enhanced expression of AID mRNA occurs, RT-PCR was conducted by the standard method (Immunity, 9:1–10, 1998).

Red blood cells were removed from splenocytes obtained from spleen which was obtained 5 days after the immunization of SRBC in the same manner as the above, and T cells and non-T cells were separated using nylon fiber (Wako Pure Chemicals) in the same manner as in the previous report (Eur. J. Immunol., 3:645–649, 1973). T cell fractions contained more than 90% of CD3 positive cells, and less than 20% B 220 positive cells.

Concentration of T cell fractions (removal of B cells) and concentration of B cell fractions were carried out by MACS method with magnetic beads conjugated to anti-CD19 antibody (Miltenyi Biotech.). B220 positive B cells included in the fraction in which T cells were removed were 5% or less. On the other hand, B220 positive B cells included in the fraction in which CD19 positive cells were concentrated were 60% or more.

cDNA was prepared by reverse transcriptase according to the standard method using polyA$^+$ RNA prepared from each fractionated cell group. AID cDNA and GAPDH cDNA were amplified by PCR using the obtained cDNA as a template. For PCR of AID cDNA, the previously described pair of primers, AID-138 (SEQ ID NO:3) and AID-161 (SEQ ID NO:4), and the previously described pair of primers, AID-118 (SEQ ID NO:5) and AID-119 (SEQ ID NO:6), as well as Taq polymerase, were used.

FIG. 18 shows the results.

In the CD19 positive B cell fraction and non-T cell fraction, amplification of AID cDNA was observed. Specifically, it was demonstrated that enhanced expression of AID mRNA induced by immunization by SRBC occurs in spleen CD19 positive B cells.

EXAMPLE 14

Localization of AID mRNA Expression in Lymphatic Organs

It was found that timing of enhanced expression of AID mRNA in spleen is almost coincident with the initiation of germinal center (GC) formation after immunization of SRBC, from the result of the previous Examples. In this experiment, the precise localization of AID mRNA expression in lymphatic organs was analyzed using in situ hybridization.

AID cDNA, cleaved out by digesting the pGEX4T1 vector in which cDNA encoding the AID protein has been subcloned with EcoRI and XhoI, was subcloned into plasmid pBluesciptSK (+) (Stratagene). The plasmid was digested with EcoRI or XhoI to obtain linearized plasmid DNA and transcribed into RNA using the plasmid as a template in the presence of digoxigenin-labeled rUTP (Boehringer-Mannheim) using T3 RNA polymerase or T7 RNA polymerase to prepare digoxigenin-labeled antisense probes and sense probes.

Frozen tissue slices were prepared by immobilizing with paraformaldehyde from each of the spleen and Payer's patch in a normal mouse as a lymphatic organ sample. A normal mouse was immunized with SRBC in the same manner as in the above Examples, and frozen tissue slices immobilized with paraformaldehyde were obtained from spleen 5 days after the immunization.

Hybridization was conducted by applying the digoxigenin-labeled antisense AID probes or sense AID probes to each of the slides furnished with each of immobilized slices. Hybridized digoxigenin-labeled AID probe was detected using anti-digoxigenin antibody conjugated with alkaline phosphatase. The localization of anti-digoxigenin antibody conjugated to digoxigenin on the probe was identified by detecting a phosphatase reactant (dark purple color). This analysis was conducted using a light transmission microscope.

In situ hybridization and detection of riboprobes in this experiment were conducted in the same manner as in the previous report (J. Comp. Neurol., 333:398–416, 1993).

The location of the germinal center in each tissue slice was identified by staining with PNA (Vector) conjugate with FITC and observing with a inflorescent microscope.

FIGS. 19 and 20 show the results.

Figure 19E:
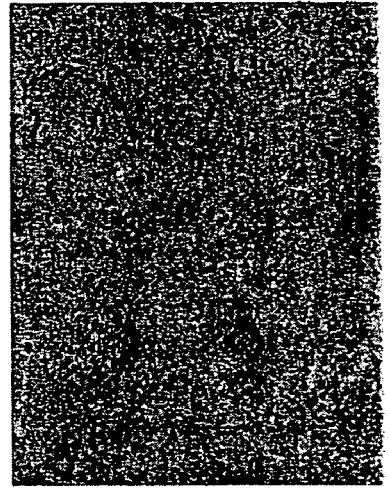
Figure 19F:
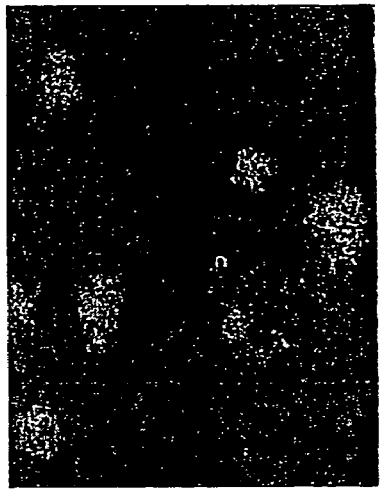

In the experiments using the antisense AID probe, multiple obvious focal signals were observed in spleen tissue slices derived from SRBC immunized mouse (day 5 after the immunization) (FIGS. 19(E) and 20(E)), however, no signals were detected in spleen tissue slices derived from mice which were not immunized with SRBC (FIGS. 19(B) and 20(B)). This result is consistent with the result of Northern blotting obtained in the above Example (FIG. 17). The existence of a germinal center was observed both in spleen tissue slices derived from SRBC-immunized mouse (day 5 after the immunization) (FIGS. 19(F) and 20(F)) as well as in the normal Payer's patch (FIG. 20(I)), by staining with FITC-labeled PNA. The expression of AID mRNA was found to localize in the germinal center in both tissue slices.

In the experiments using the sense AID probe, no background signals were detected in tissue slices of spleen or of Payer's patch regardless of the presence or absence of the immunization by SRBC.

This result indicates that the induction of AID mRNA expression occurs specifically in germinal center B cells activated by stimulation with an antigen.

EXAMPLE 15

Isolation of Human Genomic DNA Encoding the AID Protein 15-1 Preparation of Probes for Hybridization PCR was conducted using an expression vector, prepared by inserting cDNA encoding a full length mouse AID protein, (prepared in Example 5) into a plasmid vector pGEX4T1, as a template, with a pair of primers (Primer 170: SEQ ID NO:16 and primer 181: SEQ ID NO:179), according to the standard method described in the above.

The resulting PCR product was purified by the standard methods described above and a nucleotide sequence of the purified DNA was determined by a direct sequencing method to confirm that the purified DNA is the nucleotide sequence encoding a full length mouse AID protein. This purified DNA was used as a probe for hybridization in the following experiments.

15-2 Screening of Human Genomic DNA Library

The probe prepared in the above was labeled in the same manner as the radioactive probe in the above Northern hybridization to make a probe radio-labeled by a radioactive isomer.

Using the labeled probe, a commercial human genomic DNA library (catalogue No. HL1067j; Lot No. 45003; CLONTECH) was screened by cross hybridization according to the standard method.

Washing after hybridization was conducted twice in 2×SSC (including 0.1% SDS, at room temperature, 10 min), and twice in 2×SSC (including 0.1% SDS, 65° C., 30 min). Phage DNA was subcloned by purifying phage DNA and inserting about 22 kb genomic DNA, obtained by cleaving at NotI restriction enzyme site in the phage DNA, into the Not I restriction enzyme site in plasmid pZero-2.1. This plasmid was named 3CpZero.

A DNA fragment obtained by digesting 3CPZero with PstI was ligated to the PstI site of plasmid pBlueScript KS (Toyobo) and E. coli was transformed with this ligated DNA.

Transformants were screened by the colony hybridization using the labeled probe prepared in the above according to the standard method, and multiple positive clones were obtained.

The nucleotide sequence of human genomic DNA inserted into each positive clone was analyzed and multiple clones containing genomic DNA of DNA encoding a human AID protein were identified.

Among the multiple clones, nucleotide sequences of genomic DNA containing DNA encoding a human AID protein contained in two clones are described in SEQ ID NOs:9 and 10, respectively.

In addition, the nucleotide sequence of genomic DNA including the DNA encoding a human AID protein included in the other positive clone is shown in SEQ ID NO:35.

EXAMPLE 16

Isolation of cDNA Encoding a Full-length Human AID Protein and Preparation of Human AID Protein By comparing the nucleotide sequence of genomic DNA, including the coding region of the human AID protein, with cDNA nucleotide sequence encoding the full-length mouse AID protein (determined in the examples above), a human AID protein encoding region in the human genomic DNA was deduced.

A pair of primers for RACE-PCR was designed based on the deduced nucleotide sequence of the coding region in the human AID protein (Primer 22: SEQ ID NO:18, and primer 25: SEQ ID NO:19).

RACE-PCR was conducted using mRNA prepared from human B Lymphoma cell line RAMOS as a template with the above pair of primers according to a previous report (J. Biol. Chem., 274:18470–18476, 1999) following the standard method. The nucleotide sequence of the resulting PCR product was determined and cDNA encoding a full length human AID protein was obtained (cDNA sequence: SEQ ID NO:7, and amino acid sequence: SEQ ID NO:8).

The results indicate that the human AID protein (SEQ ID NO:8) has extremely high homology in amino acid sequence with the mouse AID protein (SEQ ID NO:2) (FIG. 22). The amino acid sequences in the cytidine and deoxycytidilate deaminase zinc-binding region which is an active region in the AID protein (both mouse AID and human AID amino acid residues 56 to 94 of SEQ ID NOs:2 and 8, respectively) were completely consistent (conserved) between mouse and human.

As the partial amino acid sequence (amino acid NO: 116 to 132 in SEQ ID NO:2) of mouse AID protein used for the preparation of anti-AID protein antibody (Example 5) was completely consistent with the corresponding amino acid sequence (amino acid NO: 116 to 132 in SEQ ID NO:8) of human AID protein, the anti-AID protein antibody was expected to cross-react not only with mouse AID protein but also with human AID protein.

Human AID cDNA obtained in the above was reconstructed according to the standard method in the manner of genetic engineering so that His-AID fusion protein, with His-tag (a peptide of histidine repeated 10 times) added at the N-terminus of the human AID protein, was produced, and an expression vector was prepared by inserting the cDNA into a plasmid pEF-BOS (Unexamined published Japanese patent No. Hei 2-242687). The vector was introduced into a monkey kidney-derived cell line, COS7, by lipofection using LIPOFECTAMINE (GIBCO BRL) according to the standard method. The resulting transgenic cells were cultured by standard methods and His-human AID fusion protein was transiently expressed. His-human AID fusion protein was extracted and purified in the same method as previously reported, and the production of His-human AID fusion protein was analyzed by Western blotting with the anti-AID antibody prepared in Example 5 and a commercial anti-His tag antibody according to the standard method. The His-AID protein was detected as a band comprising about 31 kDa molecular weight in all cases using either antibody.

EXAMPLE 17

Determination of Exons in the Genomic DNA Encoding the Human AID Protein

Based on the information for the nucleotide sequence of the cDNA encoding the full length human AID protein above, exons in the nucleotide sequences for genomic DNA encoding the human AID protein in the above were determined.

As a result, the genomic DNA was confirmed to consist of 5 exons.

Exon 1 (Nucleotide sequence: SEQ ID NO:11);
Exon 2 (Nucleotide sequence: SEQ ID NO:12);
Exon 3 (Nucleotide sequence: SEQ ID NO:13);
Exon 4 (Nucleotide sequence: SEQ ID NO:14); and
Exon 5 (Nucleotide sequence: SEQ ID NO:15).

Exon 1 contains a translation initiation codon ATG which codes for the first methionine (Amino acid No:1 of SEQ ID NO:8) in the human AID protein; the initiation codon corresponds to nucleotides NOs:80 to 82 in SEQ NO:11.

Specifically, the genomic DNA including DNA encoding the human AID obtained in the above Examples (SEQ ID NO:9, SEQ ID NO:10 and SEQ ID NO:35) consists of introns and exons as described below and comprises a full length of about 11 kb. FIG. 23 schematically shows the structure.

<SEQ ID NO:9>
Intron: Nucleotide Nos. from 1 to 1031
Exon 1: Nucleotide Nos. from 1032 to 1118
Intron: Nucleotide Nos. from 1119 to 5514
<SEQ ID NO:10>
Intron: Nucleotide Nos. from 1 to 1064
Exon 2: Nucleotide Nos. from 1065 to 1212
Intron: Nucleotide Nos. from 1213 to 2591
Exon 3: Nucleotide Nos. from 2592 to 2862
Intron: Nucleotide Nos. from 2863 to 3155
Exon 4: Nucleotide Nos. from 3156 to 3271
Intron: Nucleotide Nos. from 3272 to 3740
Exon 5: Nucleotide Nos. from 3741 to 5912
Intron: Nucleotide Nos. from 5913 to 6564
<SEQ ID NO:35>
Intron: Nucleotide Nos. from 1 to 441
Exon 1: Nucleotide Nos. from 442 to 528
Intron: Nucleotide Nos. from 529 to 6279

Exon 2: Nucleotide Nos. from 6280 to 6427
Intron: Nucleotide Nos. from 6428 to 7806
Exon 3: Nucleotide Nos. from 7807 to 8077
Intron: Nucleotide Nos. from 8078 to 8370
Exon 4: Nucleotide Nos. from 8371 to 8486
Intron: Nucleotide Nos. from 8487 to 8955
Exon 5: Nucleotide Nos. from 8956 to 11067
Intron: Nucleotide Nos. from 11068 to 11204

EXAMPLE 18

Amplification of a Given Partial Nucleotide Sequence of Genomic DNA Encoding the Human AID Protein by PCR, and Diagnosis of the Presence or Absence of Mutations in the Partial Nucleotide Sequence The AID protein of the present invention may be involved in the development of various immunodeficiency and allergic diseases. For example, a given immunodeficiency or allergic disease may be caused by mutation or deletion in the nucleotide sequence of genomic DNA (especially in an exon) encoding an AID protein.

The presence or absence of such a mutation or deletion in the genomic DNA can be analyzed by, for example, the following examples.

(1) A pair of primers comprising a nucleotide sequence complementary to a given partial nucleotide sequence of genomic DNA encoding the AID protein in the present invention is prepared.

(2) Using genomic DNA encoding the AID protein obtained from tissues or cells of a patient suffering from immunodeficiency or allergic disease as a template, an objective partial nucleotide sequence of the genomic DNA is amplified with the pair of primers.

(3) By analyzing the presence or absence of a PCR product and a nucleotide sequence of the PCR product, and comparing the nucleotide sequence with a corresponding nucleotide sequence in genomic DNA encoding the AID protein derived from a normal person, a mutation or deletion in the genomic DNA is identified.

Specifically, this method enables, for example, not only elucidation of the relationship between immunodeficiency or allergic disease and the AID protein, but also diagnosis of diseases by the above method in the case that AID protein is a cause of development of a given type of disease (for example, immunodeficiency or allergic disease).

For the above purpose, the following 15 kinds of primers were designed and prepared based on a given partial nucleotide sequence in the genomic DNA encoding the human AID protein.

Primer: p3 (SEQ ID NO:20)
Primer: p9 (SEQ ID NO:21)
Primer: p10 (SEQ ID NO:22)
Primer: p12 (SEQ ID NO:23)
Primer: p14 (SEQ ID NO:24)
Primer: p16 (SEQ ID NO:25)
Primer: p17 (SEQ ID NO:26)
Primer: p19 (SEQ ID NO:27)
Primer: p26 (SEQ ID NO:28)
Primer: p29 (SEQ ID NO:29)
Primer: p36 (SEQ ID NO:30)
Primer: p48 (SEQ ID NO:31)
Primer: p59 (SEQ ID NO:32)
Primer: p85 (SEQ ID NO:33)
Primer: p86 (SEQ ID NO:34)

By PCR using the above primers in pairs in the following combinations, and genomic DNA isolated from human B lymphoma cell RAMOS as a template, a partial nucleotide sequence coding each target human AID protein was amplified. FIG. 21 shows the relative locations of genomic DNA partial nucleotide sequences amplified by each primer pair.

(1) DNA comprising the nucleotide sequence of SEQ ID NO:31 and DNA comprising the nucleotide sequence of SEQ ID NO:32;
(2) DNA comprising the nucleotide sequence of SEQ ID NO:20 and DNA comprising the nucleotide sequence of SEQ ID NO:22;
(3) DNA comprising the nucleotide sequence of SEQ ID NO:21 and DNA comprising the nucleotide sequence of SEQ ID NO:30;
(4) DNA comprising the nucleotide sequence of SEQ ID NO:24 and DNA comprising the nucleotide sequence of SEQ ID NO:25;
(5) DNA comprising the nucleotide sequence of SEQ ID NO:23 and DNA comprising the nucleotide sequence of SEQ ID NO:27;
(6) DNA comprising the nucleotide sequence of SEQ ID NO:23 and DNA comprising the nucleotide sequence of SEQ ID NO:28;
(7) DNA comprising the nucleotide sequence of SEQ ID NO:23 and DNA comprising the nucleotide sequence of SEQ ID NO:29;
(8) DNA comprising the nucleotide sequence of SEQ ID NO:26 and DNA comprising the nucleotide sequence of SEQ ID NO:27;
(9) DNA comprising the nucleotide sequence of SEQ ID NO:26 and DNA comprising the nucleotide sequence of SEQ ID NO:28;
(10) DNA comprising the nucleotide sequence of SEQ ID NO:26 and DNA comprising the nucleotide sequence of SEQ ID NO:29;
(11) DNA comprising the nucleotide sequence of SEQ ID NO:34 and DNA comprising the nucleotide sequence of SEQ ID NO:28;
(12) DNA comprising the nucleotide sequence of SEQ ID NO:34 and DNA comprising the nucleotide sequence of SEQ ID NO:29;
(13) DNA comprising the nucleotide sequence of SEQ ID NO:33 and DNA comprising the nucleotide sequence of SEQ ID NO:29; or,
(14) DNA comprising the nucleotide sequence of SEQ ID NO:18 and DNA comprising the nucleotide sequence of SEQ ID NO:19;

The condition for PCR was set by the following manner.
<Reaction Solution>
A total amount of 20.2 µl consisting of DDW (8 µl), 10× buffer (2 µl), dNTP (2.5 mM each, 2 µl), 2 mM primer 1 (2 µl), 2 µM primer 2 (2 µl), genomic DNA isolated from human B Lymphoma cells (185 ng/µl) and Taq polymerase (5 U/ml, 0.2 µl), Ex Taq (TAKARA), or Ampli Taq (Perkin Elmer).
<Reaction>
Reaction was conducted according to the following conditions (A) or (B).

(A) Conducting 1 cycle of [reaction at 94° C. for 30 sec] and 40 cycles of [reaction at 94° C. for 10 sec, reaction at 54° C. for 30 sec, and reaction at 72° C. for 3 min and 30 sec], and subsequently stored at 4° C.

(B) Conducting 1 cycle of [reaction at 94° C. for 30 sec] and 40 cycles of [reaction at 94° C. for 10 sec, reaction at 55° C. for 30 sec, and reaction at 72° C. for 2 min and 10 sec], and subsequently stored at 4° C.

<PCR Equipment>
A commercial PCR device (Perkin Elmer Thermal Cycler 9700 type) was used.

EXAMPLE 19

The expression of Human AID mRNA in Various Human Organ Tissues

The expression of human AID mRNA in various human organ tissues was analyzed by RT-PCR according to the standard method (Immunity, 9:1–10, 1998).

RT-PCR was conducted using various tissues in a human tissue cDNA panel (CLONTECH) as a template according to standard methods.

AID cDNA was amplified using primers p17 (SEQ ID NO:26) and p26 (SEQ ID NO:28) prepared as above, and Taq polymerase.

As a control, RT-PCR was conducted in the same manner using cDNA of G3PDH as a template and GF primer and GR primer (Immunity, 9:1–10, 1998).

FIG. 24 shows the results. As a result, Specific expression of mRNA was confirmed in lymph node and tonsil. This result was consistent with the experimental result in which the expression of mRNA for mouse AID was observed in the various lymphatic tissues (Examples 8 and 9).

On the other hand, when RT-PCR was conducted with a saturated cycle number in the same manner as the above in the above RT-PCR, the expression of AID mRNA was observed in almost all analyzed organs.

EXAMPLE 20

Localization of Human AID Gene on Human Chromosomes

Localization of the human AID gene on human chromosomes was analyzed by fluorescence in situ hybridization (FISH) method (Experimental Medicine, Suppl. "Genetic Engineering Hand Book" published by Yodosha, 1992, p. 271–277).

Genomic DNA including human AID gene (exon 1 to exon 5), isolated in the above, which was labeled with biotin-11-dUTP (Sigma) by the nick translation method, was used as a probe for hybridization.

The probe was hybridized with chromosomes in metaphase human cells. Hybridization signals were detected using fluorescein isothiocyanate-avidin (DCS) (Vector Laboratories).

FIG. 25 shows the results. The human AID gene was found to be localized on chromosome 12p13. This location is near 12p13.1 which is the location for APOBEC-1 which has a relatively high amino acid sequence homology with the AID protein, and has the same cytidine deaminase activity as the AID protein.

It has been reported that some abnormality on human chromosome locus 12p13.3–12p11.2, 12p13.2–12p24.1 and 12p13 may be involved in diseases such as acrocallosal syndrome, inflammatory bowel syndrome, familial periodic fever, respectively, however, the causative gene thereof has not been traced yet. The human AID gene of the present invention may be involved in the development of such diseases.

All references and patents cited herein are incorporated by reference in their entirety.

INDUSTRIAL APPLICABILITY

The AID protein of the present invention can be considered to have a function of regulating various biological mechanisms required for generation of antigen-specific immunoglobulins (specific antibodies), which eliminate non-self antigen (foreign antigen, self-reacting cells, etc.) that triggers various diseases. More specifically, the AID protein of the present invention can be considered to be one of the enzymes that play an important role in genetic editing such as RNA editing, and so on occurring in germinal center B cells, such as the activation of B cells, class switch recombination of immunoglobulin genes, somatic hypermutation, and affinity maturation, which are the mechanisms for generation of immunoglobulins having high specificity for antigens.

The dysfunction of the AID protein of the present invention can be the cause of humoral immunodeficiency since it induces failure of germinal center B cell function, such as antigen-specific B cell activation, class switch recombination, and somatic mutation. Conversely, the breakdown of the regulation of AID protein may induce allergic diseases or autoimmune diseases since it can cause inappropriate B cell activation and needless class switch recombination and somatic mutation.

Therefore, regulation of the function of AID protein and the gene encoding it enables prevention and treatment of various immunodeficiencies, autoimmune diseases, and allergies, which result from, for example, B cell dysfunctions (e.g. IgA deficiency, IgA nephropathy, γ globulinemia, hyper IgM syndrome, etc.) or class switch deficiency of immunoglobulin. Thus, the AID protein and the gene encoding the AID protein can be targets for the development of drugs for therapy of the diseases mentioned above.

Examples of diseases whose onset prevention, symptom remission, therapy and/or symptomatic treatment effect is expected by regulating the function of the AID protein of the present invention or the gene encoding it include, for example, primary immunodeficiency syndrome with congenital disorder of immune system, mainly immunodeficiencies considered to develop by B cell deficiency, decrease, or dysfunction (e.g. sex-linked agammaglobulinemia, sex-linked agammaglobulinemia with growth hormone deficiency, immunoglobulin deficiency with high IgM levels, selective IgM deficiency, selective IgE deficiency, immunoglobulin heavy chain gene deletion, K chain deficiency, IgA deficiency, IgG subclass selective deficiency, CVID (common variable immunodeficiency), infantile transient dysgammaglobulinemia, Rosen syndrome, severe combined immunodeficiency (sex-linked, autosomal recessive), ADA (adenosine deaminase) deficiency, PNP (purine nucleoside phosphorylase) deficiency, MHC class II deficiency, reticular dysplasia, Wiskott-Aldrich syndrome, ataxia telangiectasia, DiGeorge syndrome, chromosomal aberration, familial Ig hypermetabolism, hyper IgE syndrome, Gitlin syndrome, Nezelof syndrome, Good syndrome, osteodystrophy, transcobalamin syndrome, secretary bead syndrome, etc.), various diseases with antibody production deficiency that are secondary immunodeficiency syndromes with a disorder of the immune system caused by an acquired etiology (for example, AIDS, etc.), and/or various allergic diseases (e.g., bronchial asthma, atopic dermatitis, conjunctivitis, allergic rhinitis, allergic enteritis, drug-induced allergy, food allergy, allergic urticaria, glomerulonephritis, etc.). These could be targets for drug development.

Namely, the AID protein of the present invention, a fragment thereof, a DNA encoding the AID protein, a fragment thereof, and an antibody against the AID protein are useful as reagents for developing drugs for prevention and therapy of such diseases.

Also, the DNA itself is useful as an antisense drug regulating the function of the AID gene at the gene level, and in gene therapy. The protein, or the fragments thereof (e.g. enzyme active site), itself is useful as a drug.

Furthermore, an antibody reactive to the AID protein of the present invention or a fragment thereof is extremely useful as an antibody drug to regulate functions of the AID protein.

Furthermore, the gene (DNA), protein, and antibody of the present invention are useful as reagents for searching for substrates (e.g., RNA, etc.) that interact (bind) with the protein (enzyme) of the present invention, or other auxiliary proteins associated with the protein of the present invention, and for developing drugs targeting the substrates and auxiliary proteins.

Furthermore, a method for identifying a substance that regulates production of the AID protein of the present invention, or transcription of a gene encoding the AID protein into mRNA is extremely useful as a means to develop drugs for therapy and prevention of various diseases (especially, immunodeficiency and allergic disease), in which the above-mentioned AID protein or AID gene is considered to be involved.

What is claimed is:

1. A substantially pure polypeptide comprising a fragment of SEQ ID NO:8, wherein the fragment has a cytidine deaminase activity.

2. A substantially pure polypeptide that is at least 95% identical to SEQ ID NO:8, wherein the polypeptide has a cytidine deaminase activity.

3. A substantially pure polypeptide encoded by a nucleic acid comprising a nucleotide sequence that is at least 95% identical to the coding sequence of SEQ ID NO:7, wherein the polypeptide has a cytidine deaminase activity.

4. A substantially pure polypeptide encoded by a nucleic acid that hybridizes to a probe, the sequence of which consists of the complement of the coding sequence of SEQ ID NO:7, in 0.9% NaCl at 75° C., wherein the polypeptide has a cytidine deaminase activity.

5. A substantially pure polypeptide comprising an amino acid sequence wherein 1 to 10 amino acids in the amino acid sequence of SEQ ID NO:8 are substituted, deleted, and/or modified, or an amino acid sequence where 1 to 10 amino acids are added to the amino acid sequence of SEQ ID NO:8, wherein the polypeptide has a cytidine deaminase activity.

6. A substantially pure polypeptide comprising the amino acid sequence of SEQ ID NO:8.

7. A substantially pure polypeptide consisting of the amino acid sequence of SEQ ID NO:8.

* * * * *

SEQUENCE LISTING

```
<160> NUMBER OF SEQ ID NOS: 36

<210> SEQ ID NO 1
<211> LENGTH: 2440
<212> TYPE: DNA
<213> ORGANISM: Mus musculus
<220> FEATURE:
<221> NAME/KEY: CDS
<222> LOCATION: (93)...(686)
<220> FEATURE:
<221> NAME/KEY: 5'UTR
<222> LOCATION: (1)...(92)
<220> FEATURE:
<221> NAME/KEY: 3'UTR
<222> LOCATION: (690)...(2440)
<220> FEATURE:
<221> NAME/KEY: misc_feature
<222> LOCATION: (1)...(2440)
<223> OTHER INFORMATION: n = A,T,C or G

<400> SEQUENCE: 1
ggcacgagca gcactgaagc agccttgctt gaagcaagct tcctttggcc taagactttg        60
agggagtcaa gaaagtcacg ctggagaccg at atg gac agc ctt ctg atg aag       113
                                   Met Asp Ser Leu Leu Met Lys
                                    1               5 caa aag aag ttt ctt tac cat ttc aaa aat gtc cgc tgg gcc aag gga       161
Gln Lys Lys Phe Leu Tyr His Phe Lys Asn Val Arg Trp Ala Lys Gly
         10                  15                  20 cgg cat gag acc tac ctc tgc tac gtg gtg aag agg aga gat agt gcc       209
Arg His Glu Thr Tyr Leu Cys Tyr Val Val Lys Arg Arg Asp Ser Ala
     25                  30                  35 acc tcc tgc tca ctg gac ttc ggc cac ctt cgc aac aag tct ggc tgc       257
Thr Ser Cys Ser Leu Asp Phe Gly His Leu Arg Asn Lys Ser Gly Cys
 40                  45                  50                  55 cac gtg gaa ttg ttg ttc cta cgc tac atc tca gac tgg gac ctg gac       305
His Val Glu Leu Leu Phe Leu Arg Tyr Ile Ser Asp Trp Asp Leu Asp
                 60                  65                  70 ccg ggc cgg tgt tac cgc gtc acc tgg ttc acc tcc tgg agc ccg tgc       353
Pro Gly Arg Cys Tyr Arg Val Thr Trp Phe Thr Ser Trp Ser Pro Cys
             75                  80                  85 tat gac tgt gcc cgg cac gtg gct gag ttt ctg aga tgg aac cct aac       401
Tyr Asp Cys Ala Arg His Val Ala Glu Phe Leu Arg Trp Asn Pro Asn
         90                  95                 100 ctc agc ctg agg att ttc acc gcg cgc ctc tac ttc tgt gaa gac cgc       449
Leu Ser Leu Arg Ile Phe Thr Ala Arg Leu Tyr Phe Cys Glu Asp Arg
    105                 110                 115 aag gct gag cct gag ggg ctg cgg aga ctg cac cgc gct ggg gtc cag       497
Lys Ala Glu Pro Glu Gly Leu Arg Arg Leu His Arg Ala Gly Val Gln
120                 125                 130                 135
```

| | | | | | | | | | | | | | | |
|---|---|---|---|---|---|---|---|---|---|---|---|---|---|---|
| atc | ggg | atc | atg | acc | ttc | aaa | gac | tat | ttt | tac | tgc | tgg | aat | aca | ttt | 545 |
| Ile | Gly | Ile | Met | Thr | Phe | Lys | Asp | Tyr | Phe | Tyr | Cys | Trp | Asn | Thr | Phe | |
| | | | | 140 | | | | | 145 | | | | | 150 | | |

```
atc ggg atc atg acc ttc aaa gac tat ttt tac tgc tgg aat aca ttt      545
Ile Gly Ile Met Thr Phe Lys Asp Tyr Phe Tyr Cys Trp Asn Thr Phe
                140                 145                 150 gta gaa aat cgt gaa aga act ttc aaa gcc tgg gaa ggg cta cat gaa      593
Val Glu Asn Arg Glu Arg Thr Phe Lys Ala Trp Glu Gly Leu His Glu
            155                 160                 165 aat tct gtc cgg cta acc aga caa ctt cgg cgc atc ctt ttg ccc ttg      641
Asn Ser Val Arg Leu Thr Arg Gln Leu Arg Arg Ile Leu Leu Pro Leu
        170                 175                 180 tac gaa gtc gat gac ttg cga gat gca ttt cgt atg ttg gga ttt          686
Tyr Glu Val Asp Asp Leu Arg Asp Ala Phe Arg Met Leu Gly Phe
    185                 190                 195 tgaaagcaac ctcctggaat gtcacacgtg atgaaatttc tctgaagaga ctggatagaa    746
aaacaaccct tcaactacat gttttctcc ttaagtactc acttttataa gtgtaggggg    806
aaattatatg actttttaaa aaatacttga gctgcacagg accgccagag caatgatgta    866
actgagcttg ctgtgcaaca tcgccatcta ctggggaaca gcataacttc cagactttgg    926
gtcgtgaatg atgctctttt ttttcaacag catggaaaag catatggaga cgaccacaca    986
gtttgttaca cccacccctgt gttccttgat tcatttgaat tctcagggt atcagtgacg   1046
gattcttcta ttctttccct ctaaggctca ctttcagggg tccttttctg acaaggtcac   1106
ggggctgtcc tacagtctct gtctgagcaa tcacaagcca ttctctcaaa acattaata    1166
ctcaggcaca tgctgtatgt tttcactgtc cgtcgtgttt ttcacatttg tatgtgaaag   1226
ggcttggggt gggatttgaa gaatgcacga tcgcctctgg gtgatttcaa taaggatct    1286
taaaatgcag atgaggacta cgaagaaatc actctgaaaa tgagttcacg cctcaagaag   1346
caaatcccct ggaaacacag actcttttc attttaatg tcattagttt actcacagtc     1406
ttatcaagaa gaagagttca agggttcaac ccaattttca gatcgcgtcc cttaaacatc    1466
agtaattctg ttaagggat caaacatcct tatttcttaa ctaactggtg ccttgctgta    1526
gagaaggag caaagcgccc agatccaaag tatatagtta tcatagccag gaaccgctac    1586
tcgttttcca ttacaaatgg caaattcttc cccgggctct cctcatagtg cctgagacgg   1646
accacggagg tgatgaacct ccggattctc tggcccaaca cggtggaagc tctgcaaggg   1706
cgcagagaca gaatgcggca gaaattgccc ccgagtccca actctccttt ccttgcgacc   1766
ttgggaacaa gacttaaagg agcctgtgac ttagaaactt ctagtaatgg gtacctggga   1826
gtcgtttgag tatggggcag tgatttattc tctgtgatgg atgccaacac ggttaaacag   1886
aattttagt ttttatatgt gtgtgatgct gctcccccaa attgttaact gtgtaagagg    1946
gtggcaaaat agggaaagtg gcattcacct atagttccag cattcaggaa gctgaggcag   2006
gaggattgta atttgaggc cagtctgagc tgtaaggtga gaccctattt caaacaacac    2066
agccagaatt gggttctggt aaatcatact taacaaggaa aaaatgcaag acgcaagacc   2126
gtggcaagga aatgacgctt tgcccaacga aatgtaggaa accaacatag actcccagtt   2186
tgtccctctt tatgtctggt ctccctaaca acgatctttg ctaatgagaa aaatattaga   2246
aaaaaatatc cctgtgcaat tatcacccag tcgccattat aatgcaatta aaaggcccac   2306
aagaaatcct gtatacacga ccgttattta ttgtatgtaa gttgctgagg aagaggagaa   2366
aaaaataaag atcatccatt ccttcctgca aaaaaaaaa aaaaaanaaa aaaaaaaaa     2426
aaaaaaaaaa aaaa                                                     2440

<210> SEQ ID NO 2
```

```
<211> LENGTH: 198
<212> TYPE: PRT
<213> ORGANISM: Mus musculus

<400> SEQUENCE: 2

Met Asp Ser Leu Leu Met Lys Gln Lys Lys Phe Leu Tyr His Phe Lys
 1               5                  10                  15

Asn Val Arg Trp Ala Lys Gly Arg His Glu Thr Tyr Leu Cys Tyr Val
            20                  25                  30

Val Lys Arg Arg Asp Ser Ala Thr Ser Cys Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Glu
                85                  90                  95

Phe Leu Arg Trp Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Gly Ile Met Thr Phe Lys Asp Tyr
    130                 135                 140

Phe Tyr Cys Trp Asn Thr Phe Val Glu Asn Arg Glu Arg Thr Phe Lys
145                 150                 155                 160

Ala Trp Glu Gly Leu His Glu Asn Ser Val Arg Leu Thr Arg Gln Leu
                165                 170                 175

Arg Arg Ile Leu Leu Pro Leu Tyr Glu Val Asp Asp Leu Arg Asp Ala
            180                 185                 190

Phe Arg Met Leu Gly Phe
        195

<210> SEQ ID NO 3
<211> LENGTH: 30
<212> TYPE: DNA
<213> ORGANISM: Artificial Sequence
<220> FEATURE:
<223> OTHER INFORMATION: Artificially synthesized primer sequence,
      AID138

<400> SEQUENCE: 3
ggaattcgcc atggacagcc ttctgatgaa                                       30

<210> SEQ ID NO 4
<211> LENGTH: 30
<212> TYPE: DNA
<213> ORGANISM: Artificial Sequence
<220> FEATURE:
<223> OTHER INFORMATION: Artificially synthesized primer sequence,
      AID161

<400> SEQUENCE: 4
gccgctcgag tcaaaatccc aacatacgaa                                       30

<210> SEQ ID NO 5
<211> LENGTH: 25
<212> TYPE: DNA
<213> ORGANISM: Artificial Sequence
<220> FEATURE:
<223> OTHER INFORMATION: Artificially synthesized primer sequence,
      AID118
```

<400> SEQUENCE: 5
ggctgaggtt agggttccat ctcag                                              25

<210> SEQ ID NO 6
<211> LENGTH: 25
<212> TYPE: DNA
<213> ORGANISM: Artificial Sequence
<220> FEATURE:
<223> OTHER INFORMATION: Artificially synthesized primer sequence,
      AID119

<400> SEQUENCE: 6
gagggagtca agaaagtcac gctgg                                              25

<210> SEQ ID NO 7
<211> LENGTH: 2818
<212> TYPE: DNA
<213> ORGANISM: Homo sapiens
<220> FEATURE:
<221> NAME/KEY: CDS
<222> LOCATION: (80)...(673)
<220> FEATURE:
<221> NAME/KEY: 5'UTR
<222> LOCATION: (1)...(79)
<220> FEATURE:
<221> NAME/KEY: 3'UTR
<222> LOCATION: (677)...(2818)

<400> SEQUENCE: 7
agagaaccat cattaattga agtgagattt ttctggcctg agacttgcag ggaggcaaga         60
agacactctg acaccact atg gac agc ctc ttg atg aac cgg agg aag ttt        112
                   Met Asp Ser Leu Leu Met Asn Arg Arg Lys Phe
                     1               5                  10 ctt tac caa ttc aaa aat gtc cgc tgg gct aag ggt cgg cgt gag acc        160
Leu Tyr Gln Phe Lys Asn Val Arg Trp Ala Lys Gly Arg Arg Glu Thr
             15                  20                  25 tac ctg tgc tac gta gtg aag agg cgt gac agt gct aca tcc ttt tca        208
Tyr Leu Cys Tyr Val Val Lys Arg Arg Asp Ser Ala Thr Ser Phe Ser
         30                  35                  40 ctg gac ttt ggt tat ctt cgc aat aag aac ggc tgc cac gtg gaa ttg        256
Leu Asp Phe Gly Tyr Leu Arg Asn Lys Asn Gly Cys His Val Glu Leu
     45                  50                  55 ctc ttc ctc cgc tac atc tcg gac tgg gac cta gac cct ggc cgc tgc        304
Leu Phe Leu Arg Tyr Ile Ser Asp Trp Asp Leu Asp Pro Gly Arg Cys
 60                  65                  70                  75 tac cgc gtc acc tgg ttc acc tcc tgg agc ccc tgc tac gac tgt gcc        352
Tyr Arg Val Thr Trp Phe Thr Ser Trp Ser Pro Cys Tyr Asp Cys Ala
                 80                  85                  90 cga cat gtg gcc gac ttt ctg cga ggg aac ccc aac ctc agt ctg agg        400
Arg His Val Ala Asp Phe Leu Arg Gly Asn Pro Asn Leu Ser Leu Arg
             95                 100                 105 atc ttc acc gcg cgc ctc tac ttc tgt gag gac cgc aag gct gag ccc        448
Ile Phe Thr Ala Arg Leu Tyr Phe Cys Glu Asp Arg Lys Ala Glu Pro
        110                 115                 120 gag ggg ctg cgg cgg ctg cac cgc gcc ggg gtg caa ata gcc atc atg        496
Glu Gly Leu Arg Arg Leu His Arg Ala Gly Val Gln Ile Ala Ile Met
    125                 130                 135 acc ttc aaa gat tat ttt tac tgc tgg aat act ttt gta gaa aac cat        544
Thr Phe Lys Asp Tyr Phe Tyr Cys Trp Asn Thr Phe Val Glu Asn His
140                 145                 150                 155 gaa aga act ttc aaa gcc tgg gaa ggg ctg cat gaa aat tca gtt cgt        592
Glu Arg Thr Phe Lys Ala Trp Glu Gly Leu His Glu Asn Ser Val Arg

|  |  |  |  | 160 |  |  |  | 165 |  |  |  | 170 |  |  |  |
|---|---|---|---|---|---|---|---|---|---|---|---|---|---|---|---|---|
| ctc | tcc | aga | cag | ctt | cgg | cgc | atc | ctt | ttg | ccc | ctg | tat | gag | gtt | gat | 640 |
| Leu | Ser | Arg | Gln | Leu | Arg | Arg | Ile | Leu | Leu | Pro | Leu | Tyr | Glu | Val | Asp |  |
|  |  |  | 175 |  |  |  | 180 |  |  |  |  | 185 |  |  |  |  |

| gac | tta | cga | gac | gca | ttt | cgt | act | ttg | gga | ctt | tgatagcaac ttccaggaat | 693 |
|---|---|---|---|---|---|---|---|---|---|---|---|---|
| Asp | Leu | Arg | Asp | Ala | Phe | Arg | Thr | Leu | Gly | Leu |  |  |
|  |  | 190 |  |  |  |  | 195 |  |  |  |  |  |

```
gtcacacacg atgaaatatc tctgctgaag acagtggata aaaaacagtc cttcaagtct    753
tctctgtttt tattcttcaa ctctcacttt cttagagttt acagaaaaaa tatttatata    813
cgactcttta aaaagatcta tgtcttgaaa atagagaagg aacacaggtc tggccaggga    873
cgtgctgcaa ttggtgcagt tttgaatgca acattgtccc ctactgggaa taacagaact    933
gcaggacctg ggagcatcct aaagtgtcaa cgttttttcta tgacttttag gtaggatgag    993
agcagaaggt agatcctaaa aagcatggtg agaggatcaa atgtttttat atcaacatcc   1053
tttattattt gattcatttg agttaacagt ggtgttagtg atagattttt ctattctttt   1113
cccttgacgt ttactttcaa gtaacacaaa ctcttccatc aggccatgat ctataggacc   1173
tcctaatgag agtatctggg tgattgtgac cccaaaccat ctctccaaag cattaatatc   1233
caatcatgcg ctgtatgttt taatcagcag aagcatgttt ttatgtttgt acaaaagaag   1293
attgttatgg gtggggatgg aggtatagac catgcatggt caccttcaag ctactttaat   1353
aaaggatctt aaaatgggca ggaggactgt gaacaagaca ccctaataat gggttgatgt   1413
ctgaagtagc aaatcttctg gaaacgcaaa ctcttttaag gaagtcccta atttagaaac   1473
acccacaaac ttcacatatc ataattagca acaattggaa ggaagttgc ttgaatgttg    1533
gggagaggaa aatctattgg ctctcgtggg tctcttcatc tcagaaatgc aatcaggtc    1593
aaggtttgct acattttgta tgtgtgtgat gcttctccca aaggtatatt aactatataa   1653
gagagttgtg acaaaacaga atgataaagc tgcgaaccgt ggcacacgct catagttcta   1713
gctgcttggg aggttgagga gggaggatgg cttgaacaca ggtgttcaag gccagcctgg   1773
gcaacataac aagatcctgt ctctcaaaaa aaaaaaaaa aaaagaaag agagagggcc     1833
gggcgtggtg gctcacgcct gtaatcccag cactttggga ggccgagccg gcggatcac    1893
ctgtggtcag gagtttgaga ccagcctggc caacatggca aaaccccgtc tgtactcaaa   1953
atgcaaaaat tagccaggcg tggtagcagg cacctgtaat cccagctact gggaggctg    2013
aggcaggaga atcgcttgaa cccaggaggt ggaggttgca gtaagctgag atcgtgccgt   2073
tgcactccag cctgggcgac aagagcaaga ctctgtctca gaaaaaaaaa aaaaaaagag   2133
agagagagag aaagagaaca atatttggga gagaaggatg gggaagcatt gcaaggaaat   2193
tgtgctttat ccaacaaaat gtaaggagcc aataagggat ccctatttgt ctctttttggt  2253
gtctatttgt ccctaacaac tgtctttgac agtgagaaaa atattcagaa taaccatatc   2313
cctgtgccgt tattacctag caacccttgc aatgaagatg agcagatcca caggaaaact   2373
tgaatgcaca actgtcttat tttaatctta ttgtacataa gtttgtaaaa gagttaaaaa   2433
ttgttacttc atgtattcat ttatatttta tattattttg cgtctaatga ttttttatta   2493
acatgatttc ctttctgat atattgaaat ggagtctcaa agcttcataa atttataact   2553
ttagaaatga ttctaataac aacgtatgta attgtaacat tgcagtaatg gtgctacgaa   2613
gccatttctc ttgattttta gtaaacttt atgacagcaa atttgcttct ggctcacttt    2673
caatcagtta aataaatgat aaataatttt ggaagctgtg aagataaaat accaaataaa   2733
ataatataaa agtgatttat atgaagttaa aataaaaaat cagtatgatg gaataaactt   2793
```

-continued

```
gaaaaaaaaa aaaaaaaaaa aaaaa                                          2818
```

<210> SEQ ID NO 8
<211> LENGTH: 198
<212> TYPE: PRT
<213> ORGANISM: Homo sapiens

<400> SEQUENCE: 8

```
Met Asp Ser Leu Leu Met Asn Arg Arg Lys Phe Leu Tyr Gln Phe Lys
 1               5                  10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 9
<211> LENGTH: 5514
<212> TYPE: DNA
<213> ORGANISM: Homo sapiens
<220> FEATURE:
<221> NAME/KEY: intron
<222> LOCATION: (1)...(1031)
<220> FEATURE:
<221> NAME/KEY: exon
<222> LOCATION: (1032)...(1118)
<220> FEATURE:
<221> NAME/KEY: intron
<222> LOCATION: (1119)...(5514)

<400> SEQUENCE: 9

```
acagacgaat acatggtcca agctagggct attgatttga aaatcatcaa ggtatagatg      60
gtatcaaagg cttgaggcag gaagagagca gagacccctag ctgcattgct tagcattgca    120
tccctagcac ctggcatagt ttccattaac agtaggcatg aagtatctac tcagtgaata    180
aatagaatgc atatgggcta cagtaggaga gagaaataaa atctttaata gaccaagttc    240
tatgagagca caaaattaaa gtctttatt tgaagatctt agcctgtttt ccaaattcag     300
tgcagccagt tagacactga ttctgtctgg tgaaacaagc attttgtat tttgggggac     360
```

```
tgctgctgct tctgactcca aattaaggat ttttttttttt tctaaaaaag atggctcatg       420
caaaaatcac tctttggtgt aaatatctag tcttcaagca attcttgtaa tgcaatcaga       480
aagaaaaaaa tccatggttt gggaggcaaa attttttgtgt tctaaattct atataactga     540
gttcatttgc ttaactgcaa agcaggagct gctagtgcct gtctgtactg aggttcagag       600
agactgtggg aatatggggg aattagaggc tatctgaggc tcttcaacac aataacccaa       660
gaagctattt aaatgctctt taaggtattt acataaatat tactattctc attgtgcttt       720
tattttgtgt tatcatgatt ataattgaag tgtctactgt tactgcctcc tgatctttgc       780
tagctatgga gcatggactg ggcttttaga gcagcagccc caaggaacc taaacattaa        840 agcagagctg ccctcaatgg tttaacctgt gtgactctgc ctatgacagc cccacccacc       900
catcttcact ggatccaaat caggagcaag gccgttgggg tacctggtgg gggtgatgct       960
gtcaggggag gagcccaaaa gggcaagctc aaatttgaat gtgaagggcc aatgcactgt      1020
cagactgaga cagagaacca tcattaattg aagtgagatt tttctggcct gagacttgca      1080
gggaggcaag aagacactct ggacaccact atggacaggt aaagaggcag tcttctcgtg      1140
ggtgattgca ctggccttcc tctcagagca aatctgagta atgagactgg tagctatccc      1200
tttctctcat gtaactgtct gactgataag atcagcttga tcaatatgca tatatatttt      1260
ttgatctgtc tcctttttctt ctattcagat cttatacgct gtcagcccaa ttctttctgt     1320
ttcagacttc tcttgatttc cctcttttttc atgtggcaaa agaagtagtg cgtacaatgt     1380
actgattcgt cctgagattt gtaccatggt tgaaactaat ttatggtaat aatattaaca      1440
tagcaaatct ttagagactc aaatcatgaa aaggtaatag cagtactgta ctaaaaacgg      1500
tagtgctaat tttcgtaata attttgtaaa tattcaacag taaaacaact tgaagacaca      1560 cttttcctagg gaggcgttac tgaaataatt tagctatagt aagaaaattt gtaattttag     1620
aaatgccaag cattctaaat taattgcttg aaagtcacta tgattgtgtc cattataagg      1680
agacaaattc attcaagcaa gttatttaat gttaaaggcc caattgttag gcagttaatg      1740
gcacttttac tattaactaa tcttttccatt tgttcagacg tagcttaact tacctcttag    1800
gtgtgaattt ggttaaggtc ctcataatgt ctttatgtgc agttttttgat aggttattgt     1860 catagaactt attctattcc tacatttatg attactatgg atgtatgaga ataacaccta      1920
atccttatac tttacctcaa tttaactcct ttataaagaa cttacattac agaataaaga      1980
ttttttaaaa atatatttttt ttgtagagac agggtcttag cccagccgag gctggtctct     2040
aagtcctggc ccaagcgatc ctcctgcctg ggcctcctaa agtgctggaa ttatagacat      2100
gagccatcac atccaatata cagaataaag atttttaatg gaggatttaa tgttcttcag     2160
aaaattttct tgaggtcaga caatgtcaaa tgtctcctca gtttacactg agattttgaa      2220
aacaagtctg agctataggt ccttgtgaag ggtccattgg aaatacttgt tcaaagtaaa      2280
atggaaagca aaggtaaaat cagcagttga aattcagaga aagacagaaa aggagaaaag      2340
atgaaattca acaggacaga agggaaatat attatcatta aggaggacag tatctgtaga      2400
gctcattagt gatggcaaaa tgacttggtc aggattattt ttaacccgct tgtttctggt      2460
ttgcacggct ggggatgcag ctagggttct gcctcaggga gcacagctgt ccagagcagc      2520
tgtcagcctg caagcctgaa acactccctc ggtaaagtcc ttcctactca ggacagaaat      2580
gacgagaaca gggagctgga acaggccccc taaccagaga agggaagtaa tggatcaaca      2640
aagttaacta gcaggtcagg atcacgcaat tcatttcact ctgactggta acatgtgaca      2700
gaaacagtgt aggcttattg tattttcatg tagagtagga cccaaaaatc cacccaaagt      2760
```

```
cctttatcta tgccacatcc ttcttatcta tacttccagg acacttttc ttccttatga      2820 taaggctctc tctctctcca cacacacaca cacacacaca cacacacaca cacacacaca      2880
cacaaacaca caccccgcca accaaggtgc atgtaaaaag atgtagattc ctctgccttt      2940
ctcatctaca cagcccagga gggtaagtta atataagagg gatttattgg taagagatga      3000
tgcttaatct gtttaacact gggcctcaaa gagagaattt cttttcttct gtacttatta      3060
agcacctatt atgtgttgag cttatatata caaagggtta ttatatgcta atatagtaat      3120
agtaatgktg gttggtacta tggtaattac cataaaaatt awtatccttt taaaataaag      3180
ctaattatta ttggatcttt tttagtattc attttatgtt ttttatgttt ttgatttttt      3240
aaaagacaat ctcaccctgt tacccaggct ggagtgcagt ggtgcaatca tagctttctg      3300
cagtcttgaa ctcctgggct caagcaatcc tcctgccttg gcctcccaaa gtgttgggat      3360
acagtcatga gccactgcat ctggcctagg atccatttag attaaaatat gcattttaaa      3420
ttttaaaata atatggctaa ttttaccttt atgtaatgtg tatactggta ataaatctag      3480
tttgctgcct aaagttttaa gtgctttcca ataagcttca tgtacgtgag gggagacatt      3540
taaagtgaaa cagacagcca ggtgtggtgg ctcacgcctg taatcccagc actctgggag      3600
gctgaggtgg gtggatcgct tgagccctgg agttcaagac cagcctgagc aacatggcaa      3660
aaccctgttt ctataacaaa aattagccgg gcatggtggc atgtgcctgt ggtcccagct      3720 actaggggc tgaggcagga gaatctttgg agcccaggag gtcaaggctg cactgagcag      3780
tgcttgcgcc actgcactcc agcctgggtg acaggaccag accttgcctc aaaaaaataa      3840
gaagaaaaat taaaaataaa tggaaacaac tacaaagagc tgttgtccta gatgagctac      3900
ttagttaggc tgatattttg gtatttaact tttaaagtca gggtctgtca cctgcactac      3960
attattaaaa tatcaattct caatgtatat ccacacaaag actggtacgt gaatgttcat      4020 agtacctta ttcacaaaac cccaaagtag agactatcca aatatccatc aacagtgaa       4080 caaataaaca aaatgtgcta tatccatgca atggaatacc accctgcagt acaaaggaag     4140
aagctacttg gggatgaatc ccaaagtcat gacgctaaat gaaagagtca gacatgaagg     4200
aggagataat gtatgccata cgaaattcta gaaaatgaaa gtaacttata gttacagaaa     4260
gcaaatcagg gcaggcatag aggctcacac ctgtaatccc agcactttga gaggccacgt     4320
gggaagattg ctagaactca ggagttcaag accagcctgg gcaacacagt gaaactccat     4380
tctccacaaa aatgggaaaa aaagaaagca aatcagtggt tgtcctgtgg ggaggggaag     4440
gactgcaaag agggaagaag ctctggtggg gtgagggtgg tgattcaggt tctgtatcct     4500
gactgtggta gcagtttggg gtgtttacat ccaaaaatat tcgtagaatt atgcatctta     4560
aatgggtgga gtttactgta tgtaaattat acctcaatgt aagaaaaaat aatgtgtaag     4620
aaaagtttca attctcttgc cagcaaacgt tattcaaatt cctgagccct ttacttcgca     4680
aattctctgc acttctgccc cgtaccatta ggtgacagca ctagctccac aaattggata     4740
aatgcatttc tggaaaagac tagggacaaa atccaggcat cacttgtgct ttcatatcaa     4800
ccacgctgta cagcttgtgt tgctgtctgc agctgcaatg gggactcttg atttctttaa     4860
ggaaacttgg gttaccagag tatttccaca atgctattc aaattagtgc ttatgatatg      4920
caagacactg tgctaggagc cagaaaacaa agaggaggag aaatcagtca ttatgtggga     4980
acaacatagc aagatattta gatcattttg actagttaaa aaagcagcag agtacaaaat     5040
cacacatgca atcagtataa tccaaatcat gtaaatatgt gcctgtagaa agactagagg     5100
```

| | |
|---|---|
| aataaacaca agaatcttaa cagtcattgt cattagacac taagtctaat tattattatt | 5160 |
| agacactatg atatttgaga tttaaaaaat ctttaatatt ttaaaattta gagctcttct | 5220 |
| attttttccat agtattcaag tttgacaatg atcaagtatt actctttctt tttttttttt | 5280 |
| tttttttttt tttgagatgg agttttggtc ttgttgccca tgctggagtg gaatggcatg | 5340 |
| aycatagctc actgcaacct ccacctcctg ggttcaagca agctgtcgc ctcagcctcc | 5400 |
| cgggtagatg ggattacagg cgcccaccac cacactcggc taatgtttgt attttagta | 5460 |
| gagatggggt ttcaccatgt tggccaggct ggtctcaaac tcctgacctc agag | 5514 |

<210> SEQ ID NO 10
<211> LENGTH: 6564
<212> TYPE: DNA
<213> ORGANISM: Homo sapiens

<400> SEQUENCE: 10

| | |
|---|---|
| gggggcctgt aatcccagct actcaggagg ctgaggcagg aggatccgcg gagcctggca | 60 |
| gatctgcctg agcctgggag gttgaggcta cagtaagcca agatcatgcc agtatacttc | 120 |
| agcctgggcg acaaagtgag accgtaacaa aaaaaaaaaa atttaaaaaa agaaatttag | 180 |
| atcaagatcc aactgtaaaa agtggcctaa acaccacatt aaagagtttg gagtttattc | 240 |
| tgcaggcaga agagaaccat caggggtct tcagcatggg aatggcatgg tgcacctggt | 300 |
| ttttgtgaga tcatggtggt gacagtgtgg ggaatgttat tttggaggga ctggaggcag | 360 |
| acagaccggt taaaggcca gcacaacaga taaggaggaa gaagatgagg gcttggaccg | 420 |
| aagcagagaa gagcaaacag ggaaggtaca aattcaagaa atattggggg gtttgaatca | 480 |
| acacatttag atgattaatt aaatatgagg actgaggaat aagaaatgag tcaaggatgg | 540 |
| ttccaggctg ctaggctgct tacctgaggt ggcaaagtcg ggaggagtgg cagtttagga | 600 |
| caggggcag ttgaggaata ttgttttgat cattttgagt ttgaggtaca agttggacac | 660 |
| ttaggtaaag actggagggg aaatctgaat atacaattat gggactgagg aacaagttta | 720 |
| ttttattttt tgtttcgttt tcttgttgaa gaacaaattt aattgtaatc ccaagtcatc | 780 |
| agcatctaga agacagtggc aggaggtgac tgtcttgtgg gtaagggttt ggggtccttg | 840 |
| atgagtatct ctcaattggc cttaaatata agcaggaaaa ggagtttatg atggattcca | 900 |
| ggctcagcag ggctcaggag ggctcaggca gccagcagag gaagtcagag catcttcttt | 960 |
| ggtttagccc aagtaatgac ttccttaaaa agctgaagga aaatccagag tgaccagatt | 1020 |
| ataaactgta ctcttgcatt ttctctccct cctctcaccc acagcctctt gatgaaccgg | 1080 |
| aggaagtttc tttaccaatt caaaatgtc cgctgggcta agggtcggcg tgagacctac | 1140 |
| ctgtgctacg tagtgaagag gcgtgacagt gctacatcct tttcactgga ctttggttat | 1200 |
| cttcgcaata aggtatcaat taaagtcagc tttgcaagca gtttaatggt caactgtgag | 1260 |
| tgcttttaga gccacctgct gatggtatta cttccatcct tttttggcat ttgtgtctct | 1320 |
| atcacattcc tcaaatcctt ttttttattt cttttccat gtccatgcac ccatattaga | 1380 |
| catgcccaa aatatgtgat ttaattcctc cccagtaatg ctgggcaccc taataccact | 1440 |
| ccttccttca gtgccaagaa caactgctcc caaactgttt accagctttc ctcagcatct | 1500 |
| gaattgccttt tgagattaat taagctaaaa gcatttttat atgggagaat attatcagct | 1560 |
| tgtccaagca aaaatttaa atgtgaaaaa caaattgtgt cttaagcatt tttgaaaatt | 1620 |
| aaggaagaag aatttgggaa aaaattaacg gtggttcaat tctgtttcc aaatgatttc | 1680 |
| ttttccctcc tactcacatg ggtcgtaggc cagtgaatac attcaacatg gtgatcccca | 1740 |

-continued

```
gaaaactcag agaagcctcg gctgatgatt aattaaattg atctttcggc tacccgagag   1800
aattacattt ccaagagact tcttcaccaa atccagatg ggtttacata aacttctgcc    1860
catgggtatc tcctctctcc taacacgctg tgacgtctgg gcttggtgga atctcaggga   1920
agcatccgtg gggtggaagg tcatcgtctg gctcgttgtt tgatggttat attaccatgc   1980
aattttcttt gcctacattt gtattgaata catcccaatc tccttcctat tcggtgacat   2040
gacacattct atttcagaag ctttgatttt tatcaagcac tttcatttac ttctcatggc   2100
agtgcctatt acttctctta caatacccat ctgtctgctt taccaaaatc tatttcccct   2160
tttcagatcc tcccaaatgg tcctcataaa ctgtcctgcc tccacctagt ggtccaggta   2220
tatttccaca atgttacatc aacaggcact tctagccatt tccttctca aaaggtgcaa    2280
aaagcaactt cataaacaca aattaaatct tcggtgaggt agtgtgatgc tgcttcctcc   2340
caactcagcg cacttcgtct tcctcattcc acaaaaaccc atagccttcc ttcactctgc   2400
aggactagtg ctgccaaggg ttcagctcta cctactggtg tgctcttttg agcaagttgc   2460
ttagcctctc tgtaacacaa ggacaatagc tgcaagcatc cccaaagatc attgcaggag   2520
acaatgacta aggctaccag agccgcaata aaagtcagtg aattttagcg tggtcctctc   2580
tgtctctcca gaacggctgc cacgtggaat tgctcttcct ccgctacatc tcggactggg   2640
acctagaccc tggccgctgc taccgcgtca cctggttcac ctcctggagc cctgctacg    2700
actgtgcccg acatgtggcc gactttctgc gagggaaccc caacctcagt ctgaggatct   2760
tcaccgcgcg cctctacttc tgtgaggacc gcaaggctga gccgagggg ctgcggcggc    2820
tgcaccgcgc cggggtgcaa atagccatca tgaccttcaa aggtgcgaaa gggccttccg   2880
cgcaggcgca gtgcagcagc ccgcattcgg gattgcgatg cggaatgaat gagttagtgg   2940
ggaagctcga ggggaagaag tgggcgggga ttctggttca cctctggagc cgaaattaaa   3000
gattagaagc agagaaaaga gtgaatggct cagagacaag gccccgagga aatgagaaaa   3060
tggggccagg gttgcttctt tcccctcgat ttggaacctg aactgtcttc tacccccata   3120
tccccgcctt ttttttcctttt tttttttttt tgaagattat ttttactgct ggaatacttt   3180
tgtagaaaac cacgaaagaa ctttcaaagc ctgggaaggg ctgcatgaaa attcagttcg   3240
tctctccaga cagcttcggc gcatccttt ggtaagggc ttcctcgctt tttaaatttt      3300
ctttctttct ctacagtctt ttttggagtt tcgtatattt cttatatttt cttattgttc   3360
aatcactctc agttttcatc tgatgaaaac tttattctc ctccacatca gcttttttctt   3420
ctgctgtttc accattcaga gccctctgct aaggttcctt ttccctccct tttctttctt   3480
ttgttgtttc acatctttaa atttctgtct ctccccaggg ttgcgtttcc ttcctggtca   3540
gaattctttt ctccttttt tttttttttt ttttttttt taaacaaaca aacaaaaaac     3600
ccaaaaaaac tctttcccaa tttactttct tccaacatgt tacaaagcca tccactcagt   3660
ttagaagact ctccggcccc accgaccccc aacctcgttt tgaagccatt cactcaattt   3720
gcttctctct ttctctacag cccctgtatg aggttgatga cttacgagac gcatttcgta   3780
ctttgggact ttgatagcaa cttccaggaa tgtcacacac gatgaaatat ctctgctgaa   3840
gacagtggat aaaaaacagt ccttcaagtc ttctctgttt ttattcttca actctcactt   3900
tcttagagtt tacagaaaaa atatttatat acgactcttt aaaagatct atgtcttgaa     3960
aatagagaag gaacacaggt ctggccaggg acgtgctgca attggtgcag ttttgaatgc   4020
aacattgtcc cctactggga ataacagaac tgcaggacct gggagcatcc taaagtgtca   4080
```

```
acgtttttct atgactttta ggtaggatga gagcagaagg tagatcctaa aaagcatggt    4140
gagaggatca aatgttttta tatcaacatc ctttattatt tgattcattt gagttaacag    4200
tggtgttagt gatagatttt tctattcttt tcccttgacg tttactttca agtaacacaa    4260
actcttccat caggccatga tctataggac ctcctaatga gagtatctgg gtgattgtga    4320
ccccaaacca tctctccaaa gcattaatat ccaatcatgc gctgtatgtt ttaatcagca    4380
gaagcatgtt tttatgtttg tacaaaagaa gattgttatg ggtggggatg gaggtataga    4440
ccatgcatgg tcaccttcaa gctactttaa taaaggatct taaaatgggc aggaggactg    4500
tgaacaagac accctaataa tgggttgatg tctgaagtag caaatcttct ggaaacgcaa    4560
actcttttaa ggaagtccct aatttagaaa cacccacaaa cttcacatat cataattagc    4620
aaacaattgg aaggaagttg cttgaatgtt gggagagga aaatctattg gctctcgtgg    4680
gtctcttcat ctcagaaatg ccaatcaggt caaggtttgc tacattttgt atgtgtgtga    4740
tgcttctccc aaaggtatat taactatata agagagttgt gacaaaacag aatgataaag    4800
ctgcgaaccg tggcacacgc tcatagttct agctgcttgg gaggttgagg agggaggatg    4860
gcttgaacac aggtgttcaa ggccagcctg gcaacataa caagatcctg tctctcaaaa    4920
aaaaaaaaaa aaaaagaaa gagagagggc cgggcgtggt ggctcacgcc tgtaatccca    4980
gcactttggg aggccgagcc gggcggatca cctgtggtca ggagtttgag accagcctgg    5040
ccaacatggc aaaaccccgt ctgtactcaa aatgcaaaaa ttagccaggc gtggtagcag    5100
gcacctgtaa tcccagctac ttgggaggct gaggcaggaa aatcgcttga acccaggagg    5160
tggaggttgc agtaagctga gatcgtgccg ttgcactcca gcctgggcga caagagcaag    5220
actctgtctc agaaaaaaaa aaaaaaaaga gagagagaga gaaagagaac aatatttggg    5280
agagaaggat ggggaagcat tgcaaggaaa ttgtgcttta tccaacaaaa tgtaaggagc    5340
caataaggga tccctatttg tctcttttgg tgtctatttg tccctaacaa ctgtctttga    5400
cagtgagaaa aatattcaga ataaccatat ccctgtgccg ttattaccta gcaacccttg    5460
caatgaagat gagcagatcc acaggaaaac ttgaatgcac aactgtctta ttttaatctt    5520
attgtacata agtttgtaaa agagttaaaa attgttactt catgtattca tttatatttt    5580
atattatttt gcgtctaatg attttttatt aacatgattt cctttctga tatattgaaa    5640 tggagtctca aagcttcata aatttataac tttagaaatg attctaataa caacgtatgt    5700
aattgtaaca ttgcagtaat ggtgctacga agccatttct cttgattttt agtaaacttt    5760
tatgacagca aatttgcttc tggctcactt tcaatcagtt aaataaatga taaataattt    5820
tggaagctgt gaagataaaa taccaaataa aataatataa aagtgattta tatgaagtta    5880
aaataaaaaa tcagtatgat ggaataaact tgagagtcca gaagttatcc catacatctg    5940
taatcaacta atttctcaca agggtgtaag gaccattcaa tggagaaaaa atgatcttct    6000
caacaaatgg tgctgagcta attggatatt acatgcaaag gaatgaattt gagtctctac    6060
tacacaccat atataaaaat taattaaaaa ttcatcaaat acctaaatat tagagactaa    6120
tttataaacc gtagagagaa acataggtaa aaatgtttat ggctttagat taggcaacag    6180
cttcttaatt atgacatcaa aagcacaagc aaccaaagac aaaaataaat cagttggact    6240
tcatcgaaat taaaaatctt tgtgcatcaa aggacactta gtaagaaagt gaaaagacaa    6300
cccacagaag tgggagaaaa cacttgcaaa tcatatatct gataagggtt gtgatattat    6360
gatatatata taggtttttg tccatagttc ctggcttata acccccctca cccttgttac    6420
agtcatttgt tataaggttg gatggtttag gcctcagaag caaaactctc tctctcacct    6480
```

```
tctccagccc tcctgtctct ggcacctcat tcttccctga ggccacatag aaactagaat    6540
ctctcttcca caaggcggtc aaag                                           6564

<210> SEQ ID NO 11
<211> LENGTH: 87
<212> TYPE: DNA
<213> ORGANISM: Homo sapiens

<400> SEQUENCE: 11
agagaaccat cattaattga agtgagattt ttctggcctg agacttgcag ggaggcaaga     60
agacactctg gacaccacta tggacag                                        87

<210> SEQ ID NO 12
<211> LENGTH: 148
<212> TYPE: DNA
<213> ORGANISM: Homo sapiens

<400> SEQUENCE: 12
cctcttgatg aaccggagga agtttcttta ccaattcaaa aatgtccgct gggctaaggg     60
tcggcgtgag acctacctgt gctacgtagt gaagaggcgt gacagtgcta catccttttc    120
actggacttt ggttatcttc gcaataag                                      148

<210> SEQ ID NO 13
<211> LENGTH: 271
<212> TYPE: DNA
<213> ORGANISM: Homo sapiens

<400> SEQUENCE: 13
aacggctgcc acgtggaatt gctcttcctc cgctacatct cggactggga cctagaccct     60
ggccgctgct accgcgtcac ctggttcacc tcctggagcc cctgctacga ctgtgcccga    120
catgtggccg actttctgcg agggaacccc aacctcagtc tgaggatctt caccgcgcgc    180
ctctacttct gtgaggaccg caaggctgag cccgaggggc tgcggcggct gcaccgcgcc    240
ggggtgcaaa tagccatcat gaccttcaaa g                                  271

<210> SEQ ID NO 14
<211> LENGTH: 116
<212> TYPE: DNA
<213> ORGANISM: Homo sapiens

<400> SEQUENCE: 14 attatttta ctgctggaat acttttgtag aaaaccacga aagaactttc aaagcctggg      60
aagggctgca tgaaaattca gttcgtctct ccagacagct tcggcgcatc cttttg        116

<210> SEQ ID NO 15
<211> LENGTH: 2172
<212> TYPE: DNA
<213> ORGANISM: Homo sapiens

<400> SEQUENCE: 15
cccctgtatg aggttgatga cttacgagac gcatttcgta ctttgggact ttgatagcaa     60
cttccaggaa tgtcacacac gatgaaatat ctctgctgaa gacagtggat aaaaaacagt    120
ccttcaagtc ttctctgttt ttattcttca actctcactt tcttagagtt tacagaaaaa    180
atatttatat acgactcttt aaaaagatct atgtcttgaa aatagagaag gaacacaggt    240
ctggccaggg acgtgctgca attggtgcag ttttgaatgc aacattgtcc cctactggga    300
```

-continued

```
ataacagaac tgcaggacct gggagcatcc taaagtgtca acgtttttct atgactttta    360
ggtaggatga gagcagaagg tagatcctaa aaagcatggt gagaggatca atgttttta     420 tatcaacatc ctttattatt tgattcattt gagttaacag tggtgttagt gatagatttt    480
tctattcttt tcccttgacg tttactttca agtaacacaa actcttccat caggccatga    540
tctataggac ctcctaatga gagtatctgg gtgattgtga ccccaaacca tctctccaaa    600
gcattaatat ccaatcatgc gctgtatgtt ttaatcagca gaagcatgtt tttatgtttg    660
tacaaaagaa gattgttatg ggtggggatg gaggtataga ccatgcatgg tcaccttcaa    720
gctactttaa taaggatct taaaatgggc aggaggactg tgaacaagac accctaataa     780
tgggttgatg tctgaagtag caaatcttct ggaaacgcaa actcttttaa ggaagtccct    840
aatttagaaa cacccacaaa cttcacatat cataattagc aaacaattgg aaggaagttg    900
cttgaatgtt ggggagagga aaatctattg gctctcgtgg gtctcttcat ctcagaaatg    960
ccaatcaggt caaggtttgc tacattttgt atgtgtgtga tgcttctccc aaaggtatat   1020
taactatata agagagttgt gacaaaacag aatgataaag ctgcgaaccg tggcacacgc   1080
tcatagttct agctgcttgg gaggttgagg agggaggatg gcttgaacac aggtgttcaa   1140
ggccagcctg ggcaacataa caagatcctg tctctcaaaa aaaaaaaaa aaaaaagaaa     1200 gagagagggc cgggcgtggt ggctcacgcc tgtaatccca gcactttggg aggccgagcc    1260
gggcggatca cctgtggtca ggagtttgag accagcctgg ccaacatggc aaaacccgt     1320 ctgtactcaa aatgcaaaaa ttagccaggc gtggtagcag gcacctgtaa tcccagctac    1380
ttgggaggct gaggcaggag aatcgcttga acccaggagg tggaggttgc agtaagctga    1440
gatcgtgccg ttgcactcca gcctgggcga agagcaag actctgtctc agaaaaaaaa      1500 aaaaaaaga gagagagaga gaaagagaac aatatttggg agagaaggat ggggaagcat     1560
tgcaaggaaa ttgtgctttta tccaacaaaa tgtaaggagc caataaggga tcccctatttg  1620 tctcttttgg tgtctatttg tccctaacaa ctgtctttga cagtgagaaa atatttcaga   1680
ataaccatat ccctgtgccg ttattaccta gcaacccttg caatgaagat gagcagatcc    1740
acaggaaaac ttgaatgcac aactgtctta ttttaatctt attgtacata agtttgtaaa    1800
agagttaaaa attgttactt catgtattca tttatatttt atattatttt gcgtctaatg    1860 atttttttatt aacatgattt cctttctga tatattgaaa tggagtctca aagcttcata    1920
aatttataac tttagaaatg attctaataa caacgtatgt aattgtaaca ttgcagtaat    1980
ggtgctacga agccatttct cttgattttt agtaaacttt tatgacagca aatttgcttc    2040
tggctcactt tcaatcagtt aaataaatga taaataattt tggaagctgt gaagataaaa    2100
taccaaataa aataatataa aagtgattta tatgaagtta aaataaaaaa tcagtatgat    2160
ggaataaact tg                                                        2172
```

<210> SEQ ID NO 16
<211> LENGTH: 25
<212> TYPE: DNA
<213> ORGANISM: Artificial Sequence
<220> FEATURE:
<223> OTHER INFORMATION: Artificially synthesized primer sequence, 170

<400> SEQUENCE: 16
gagaccgata tggacagcct tctga    25

<210> SEQ ID NO 17
<211> LENGTH: 27

```
<212> TYPE: DNA
<213> ORGANISM: Artificial Sequence
<220> FEATURE:
<223> OTHER INFORMATION: Artificially synthesized primer sequence, 181

<400> SEQUENCE: 17
tcacgtgtga cattccagga ggttgct                                              27

<210> SEQ ID NO 18
<211> LENGTH: 30
<212> TYPE: DNA
<213> ORGANISM: Artificial Sequence
<220> FEATURE:
<223> OTHER INFORMATION: Artificially synthesized primer sequence, 22

<400> SEQUENCE: 18
gtagtgaaga ggcgtgacag tgctacatcc                                           30

<210> SEQ ID NO 19
<211> LENGTH: 27
<212> TYPE: DNA
<213> ORGANISM: Artificial Sequence
<220> FEATURE:
<223> OTHER INFORMATION: Artificially synthesized primer sequence, 25

<400> SEQUENCE: 19
gttccctcgc agaaagtcgg ccacatg                                              27

<210> SEQ ID NO 20
<211> LENGTH: 24
<212> TYPE: DNA
<213> ORGANISM: Artificial Sequence
<220> FEATURE:
<223> OTHER INFORMATION: Artificially synthesized primer sequence, p3

<400> SEQUENCE: 20
gagtttgagg tacaagttgg acac                                                 24

<210> SEQ ID NO 21
<211> LENGTH: 23
<212> TYPE: DNA
<213> ORGANISM: Artificial Sequence
<220> FEATURE:
<223> OTHER INFORMATION: Artificially synthesized primer sequence, p9

<400> SEQUENCE: 21
tatctcctct ctcctaacac gct                                                  23

<210> SEQ ID NO 22
<211> LENGTH: 23
<212> TYPE: DNA
<213> ORGANISM: Artificial Sequence
<220> FEATURE:
<223> OTHER INFORMATION: Artificially synthesized primer sequence, p10

<400> SEQUENCE: 22
acaagctgat aatattctcc cat                                                  23

<210> SEQ ID NO 23
<211> LENGTH: 22
<212> TYPE: DNA
<213> ORGANISM: Artificial Sequence
<220> FEATURE:
<223> OTHER INFORMATION: Artificially synthesized primer sequence, p12

<400> SEQUENCE: 23
```
tcttcggtga ggtagtgtga tg                                          22

<210> SEQ ID NO 24
<211> LENGTH: 30
<212> TYPE: DNA
<213> ORGANISM: Artificial Sequence
<220> FEATURE:
<223> OTHER INFORMATION: Artificially synthesized primer sequence, p14

<400> SEQUENCE: 24
agcctcttga tgaaccggag gaagtttctt                                  30

<210> SEQ ID NO 25
<211> LENGTH: 28
<212> TYPE: DNA
<213> ORGANISM: Artificial Sequence
<220> FEATURE:
<223> OTHER INFORMATION: Artificially synthesized primer sequence, p16

<400> SEQUENCE: 25
ttattgcgaa gataaccaaa gtccagtg                                    28

<210> SEQ ID NO 26
<211> LENGTH: 21
<212> TYPE: DNA
<213> ORGANISM: Artificial Sequence
<220> FEATURE:
<223> OTHER INFORMATION: Artificially synthesized primer sequence, p17

<400> SEQUENCE: 26
tagaccctgg ccgctgctac c                                           21

<210> SEQ ID NO 27
<211> LENGTH: 22
<212> TYPE: DNA
<213> ORGANISM: Artificial Sequence
<220> FEATURE:
<223> OTHER INFORMATION: Artificially synthesized primer sequence, p19

<400> SEQUENCE: 27
cgcatcgcaa tcccgaatgc gg                                          22

<210> SEQ ID NO 28
<211> LENGTH: 28
<212> TYPE: DNA
<213> ORGANISM: Artificial Sequence
<220> FEATURE:
<223> OTHER INFORMATION: Artificially synthesized primer sequence, p26

<400> SEQUENCE: 28
caaaaggatg cgccgaagct gtctggag                                    28

<210> SEQ ID NO 29
<211> LENGTH: 23
<212> TYPE: DNA
<213> ORGANISM: Artificial Sequence
<220> FEATURE:
<223> OTHER INFORMATION: Artificially synthesized primer sequence, p29

<400> SEQUENCE: 29
gttggaagaa agtaaattgg gaa                                         23

<210> SEQ ID NO 30
<211> LENGTH: 21
<212> TYPE: DNA
<213> ORGANISM: Artificial Sequence

```
<220> FEATURE:
<223> OTHER INFORMATION: Artificially synthesized primer sequence, p36

<400> SEQUENCE: 30
gatactctca ttaggaggtc c                                              21

<210> SEQ ID NO 31
<211> LENGTH: 26
<212> TYPE: DNA
<213> ORGANISM: Artificial Sequence
<220> FEATURE:
<223> OTHER INFORMATION: Artificially synthesized primer sequence, p48

<400> SEQUENCE: 31
cattaattga agtgagattt ttctgg                                         26

<210> SEQ ID NO 32
<211> LENGTH: 22
<212> TYPE: DNA
<213> ORGANISM: Artificial Sequence
<220> FEATURE:
<223> OTHER INFORMATION: Artificially synthesized primer sequence, p59

<400> SEQUENCE: 32
agcatttgtg gaaatactct gg                                             22

<210> SEQ ID NO 33
<211> LENGTH: 24
<212> TYPE: DNA
<213> ORGANISM: Artificial Sequence
<220> FEATURE:
<223> OTHER INFORMATION: Artificially synthesized primer sequence, p85

<400> SEQUENCE: 33
aactttattt ctcctccaca tcag                                           24

<210> SEQ ID NO 34
<211> LENGTH: 21
<212> TYPE: DNA
<213> ORGANISM: Artificial Sequence
<220> FEATURE:
<223> OTHER INFORMATION: Artificially synthesized primer sequence, p86

<400> SEQUENCE: 34
gtgaatggct cagagacaag g                                              21

<210> SEQ ID NO 35
<211> LENGTH: 11204
<212> TYPE: DNA
<213> ORGANISM: Homo sapiens

<400> SEQUENCE: 35
aggttcagag agactgtggg aatatggggg aattagaggc tatctgaggc tcttcaacac     60
aataacccaa gaagctattt aaatgctctt taaggtattt acataaatat tactattctc    120
attgtgcttt tattttgtgt tatcatgatt ataattgaag tgtctactgt tactgcctcc    180
tgatctttgc tagctatgga gcatggactg ggcttttaga gcagcagccc caaaggaacc    240
taaacattaa agcagagctg ccctcaatgg tttaacctgt gtgactctgc ctatgacagc    300
cccacccacc catcttcact ggatccaaat caggagcaag gccgttgggg tacctggtgg    360
gggtgatgct gtcaggggag gagcccaaaa gggcaagctc aaatttgaat gtgaagggcc    420
aatgcactgt cagactgaga cagagaacca tcattaattg aagtgagatt tttctggcct    480
```

```
gagacttgca gggaggcaag aagacactct ggacaccact atggacaggt aaagaggcag     540
tcttctcgtg ggtgattgca ctggccttcc tctcagagca atctgagta  atgagactgg     600 tagctatccc tttctctcat gtaactgtct gactgataag atcagcttga tcaatatgca     660
tatatatttt ttgatctgtc tccttttctt ctattcagat cttatacgct gtcagcccaa     720
ttctttctgt ttcagacttc tcttgatttc cctctttttc atgtggcaaa agaagtagtg     780
cgtacaatgt actgattcgt cctgagattt gtaccatggt tgaaactaat ttatggtaat     840
aatattaaca tagcaaatct ttagagactc aaatcatgaa aaggtaatag cagtactgta     900
ctaaaaacgg tagtgctaat tttcgtaata attttgtaaa tattcaacag taaacaact     960 tgaagacaca ctttcctagg gaggcgttac tgaaataatt tagctatagt aagaaaattt    1020
gtaattttag aaatgccaag cattctaaat taattgcttg aaagtcacta tgattgtgtc    1080
cattataagg agacaaattc attcaagcaa gttatttaat gttaaaggcc caattgttag    1140
gcagttaatg gcacttttac tattaactaa tcttttccatt tgttcagacg tagcttaact   1200
tacctcttag gtgtgaattt ggttaaggtc ctcataatgt ctttatgtgc agtttttgat    1260
aggttattgt catagaactt attctattcc tacatttatg attactatgg atgtatgaga    1320
ataacaccta atccttatac tttacctcaa tttaactcct ttataaagaa cttacattac    1380
agaataaaga ttttttaaaa atatatttttt ttgtagagac agggtcttag cccagccgag   1440
gctggtctct aagtcctggc ccaagcgatc ctcctgcctg ggcctcctaa agtgctggaa    1500
ttatagacat gagccatcac atccaatata cagaataaag atttttaatg gaggatttaa    1560
tgttcttcag aaaattttct tgaggtcaga caatgtcaaa tgtctcctca gtttacactg    1620
agattttgaa aacaagtctg agctataggt ccttgtgaag ggtccattgg aaatacttgt    1680
tcaaagtaaa atggaaagca aaggtaaaat cagcagttga aattcagaga aagacagaaa    1740
aggagaaaag atgaaattca acaggacaga agggaaatat attatcatta aggaggacag    1800
tatctgtaga gctcattagt gatggcaaaa tgacttggtc aggattattt ttaacccgct    1860
tgtttctggt ttgcacggct ggggatgcag ctagggttct gcctcaggga gcacagctgt    1920
ccagagcagc tgtcagcctg caagcctgaa acactccctc ggtaaagtcc ttcctactca    1980
ggacagaaat gacgagaaca gggagctgga acaggcccc  taaccagaga agggaagtaa    2040
tggatcaaca aagttaacta gcaggtcagg atcacgcaat tcatttcact ctgactggta    2100
acatgtgaca gaaacagtgt aggcttattg tattttcatg tagagtagga cccaaaaatc    2160
cacccaaagt cctttatcta tgccacatcc ttcttatcta tacttccagg acacttttc     2220 ttccttatga taaggctctc tctctctcca cacacacaca cacacacaca cacacacaca    2280
cacacacaca cacaaacaca caccccgcca accaaggtgc atgtaaaaag atgtagattc    2340
ctctgccttt ctcatctaca cagcccagga gggtaagtta atataagagg gatttattgg    2400
taagagatga tgcttaatct gtttaacact gggcctcaaa gagagaattt cttttcttct    2460
gtacttatta agcacctatt atgtgttgag cttatatata caaagggtta ttatatgcta    2520
atatagtaat agtaatggtg gttggtacta tggtaattac cataaaaatt attatccttt    2580
taaaataaag ctaattatta ttggatctttt tttagtattc atttttatgtt ttttatgttt  2640 ttgattttt  aaaagacaat ctcaccctgt tacccaggct gggagtgcagt ggtgcaatca   2700 tagcttctg  cagtcttgaa ctcctgggct caagcaatcc tcctgccttg gcctcccaaa    2760
gtgttgggat acagtcatga gccactgcat ctggcctagg atccatttag attaaaatat    2820 gcatttttaaa ttttaaaata atatggctaa tttttacctt atgtaatgtg tatactggta   2880
```

```
ataaatctag tttgctgcct aaagttttaaa gtgctttcca ataagcttca tgtacgtgag    2940
gggagacatt taaagtgaaa cagacagcca ggtgtggtgg ctcacgcctg taatcccagc    3000
actctgggag gctgaggtgg gtggatcgct tgagccctgg agttcaagac cagcctgagc    3060
aacatggcaa aaccctgttt ctataacaaa aattagccgg gcatggtggc atgtgcctgt    3120
ggtcccagct actaggggc tgaggcagga gaatctttgg agcccaggag gtcaaggctg    3180
cactgagcag tgcttgcgcc actgcactcc agcctgggtg acaggaccag accttgcctc    3240
aaaaaaataa gaagaaaaat taaaaataaa tggaaacaac tacaaagagc tgttgtccta    3300
gatgagctac ttagttaggc tgatattttg gtatttaact tttaaagtca gggtctgtca    3360
cctgcactac attattaaaa tatcaattct caatgtatat ccacacaaag actggtacgt    3420
gaatgttcat agtacctttta ttcacaaaac cccaaagtag agactatcca aatatccatc    3480
aacaagtgaa caaataaaca aaatgtgcta tatccatgca atggaatacc ccctgcagt    3540 acaaggaag aagctacttg gggatgaatc ccaaagtcat gacgctaaat gaaagagtca    3600
gacatgaagg aggagataat gtatgccata cgaaattcta gaaaatgaaa gtaacttata    3660
gttacagaaa gcaaatcagg gcaggcatag aggctcacac ctgtaatccc agcactttga    3720
gaggccacgt gggaagattg ctagaactca ggagttcaag accagcctgg gcaacacagt    3780
gaaactccat tctccacaaa aatgggaaaa aaagaaagca aatcagtggt tgtcctgtgg    3840
ggaggggaag gactgcaaag agggaagaag ctctggtggg gtgagggtgg tgattcaggt    3900
tctgtatcct gactgtggta gcagtttggg gtgtttacat ccaaaaatat tcgtagaatt    3960
atgcatctta aatgggtgga gtttactgta tgtaaattat acctcaatgt aagaaaaaat    4020
aatgtgtaag aaaagtttca attctcttgc cagcaaacgt tattcaaatt cctgagccct    4080
ttacttcgca aattctctgc acttctgccc cgtaccatta ggtgacagca ctagctccac    4140
aaattggata aatgcatttc tggaaaagac tagggacaaa atccaggcat cacttgtgct    4200
ttcatatcaa ccacgctgta cagcttgtgt tgctgtctgc agctgcaatg gggactcttg    4260
atttctttaa ggaaacttgg gttaccagag tatttccaca aatgctattc aaattagtgc    4320
ttatgatatg caagacactg tgctaggagc cagaaaacaa agaggaggag aaatcagtca    4380
ttatgtggga acaacatagc aagatattta gatcattttg actagttaaa aaagcagcag    4440
agtacaaaat cacacatgca atcagtataa tccaaatcat gtaaatatgt gcctgtagaa    4500
agactagagg aataaacaca agaatcttaa cagtcattgt cattagacac taagtctaat    4560
tattattatt agacactatg atatttgaga tttaaaaaat ctttaatatt ttaaaattta    4620
gagctcttct atttttccat agtattcaag tttgacaatg atcaagtatt actctttctt    4680
tttttttttt tttttttttt tttgagatgg agttttggtc ttgttgccca tgctggagtg    4740
gaatggcatg accatagctc actgcaacct ccacctcctg ggttcaagca agctgtcgc    4800 ctcagcctcc cgggtagatg ggattacagg cgcccaccac cacactcggc taatgtttgt    4860
atttttagta gagatggggt ttcaccatgt tggccaggct ggtctcaaac tcctgacctc    4920
agaggatcca cctgcctcag cctcccaaag tgctgggatt acagatgtag gccactgcgc    4980
ccggccaagt attgctctta tacattaaaa aacaggtgtg agccactgcg cccagccagg    5040
tattgctctt atacattaaa aaataggccg gtgcagtggc tcacgcctgt aatcccagca    5100
ctttgggaag ccaaggcggg cagaacaccc gaggtcagga gtccaaggcc agcctggcca    5160
agatggtgaa accccgtctc tattaaaaat acaaacatta cctgggcatg atggtgggcg    5220
```

-continued

```
cctgtaatcc cagctactca ggaggctgag gcaggaggat ccgcggagcc tggcagatct   5280
gcctgagcct gggaggttga ggctacagta agccaagatc atgccagtat acttcagcct   5340
gggcgacaaa gtgagaccgt aacaaaaaaa aaaaattta aaaaaagaaa tttagatcaa   5400
gatccaactg taaaaagtgg cctaaacacc acattaaaga gtttggagtt tattctgcag   5460
gcagaagaga accatcaggg ggtcttcagc atgggaatgg catggtgcac ctggttttg    5520 tgagatcatg gtggtgacag tgtggggaat gttattttgg agggactgga ggcagacaga   5580
ccggttaaaa ggccagcaca acagataagg aggaagaaga tgagggcttg gaccgaagca   5640
gagaagagca acagggaag gtacaaattc aagaaatatt ggggggtttg aatcaacaca    5700
tttagatgat taattaaata tgaggactga ggaataagaa atgagtcaag gatggttcca   5760
ggctgctagg ctgcttacct gaggtggcaa agtcgggagg agtggcagtt taggacaggg   5820
ggcagttgag gaatattgtt ttgatcattt tgagtttgag gtacaagttg gacacttagg   5880
taaagactgg agggaaatc tgaatataca attatgggac tgaggaacaa gtttatttta    5940
ttttttgttt cgttttcttg ttgaagaaca aatttaattg taatcccaag tcatcagcat   6000
ctagaagaca gtgcaggag gtgactgtct tgtgggtaag ggtttgggt ccttgatgag      6060 tatctctcaa ttggccttaa atataagcag gaaaaggagt ttatgatgga ttccaggctc   6120
agcagggctc aggagggctc aggcagccag cagaggaagt cagagcatct tctttggttt   6180
agcccaagta atgacttcct taaaagctg aaggaaaatc cagagtgacc agattataaa    6240
ctgtactctt gcattttctc tccctcctct caccacagc ctcttgatga accgaggaa      6300 gtttctttac caattcaaaa atgtccgctg gctaagggt cggcgtgaga cctacctgtg     6360
ctacgtagtg aagaggcgtg acagtgctac atccttttca ctggactttg gttatcttcg   6420
caataaggta tcaattaaag tcagctttgc aagcagttta atggtcaact gtgagtgctt    6480
ttagagccac ctgctgatgg tattacttcc atccttttt ggcatttgtg tctctatcac     6540
attcctcaaa tccttttttt tatttctttt tccatgtcca tgcacccata ttagacatgg    6600
cccaaaatat gtgatttaat tcctccccag taatgctggg cacctaata ccactccttc    6660 cttcagtgcc aagaacaact gctcccaaac tgtttaccag ctttcctcag catctgaatt   6720
gcctttgaga ttaattaagc taaaagcatt tttatatggg agaatattat cagcttgtcc   6780
aagcaaaaat tttaaatgtg aaaaacaaat tgtgtcttaa gcattttga aaattaagga    6840 agaagaattt gggaaaaaat taacggtggt tcaattctgt tttccaaatg atttcttttc    6900
cctcctactc acatgggtcg taggccagtg aatacattca acatggtgat ccccagaaaa   6960
ctcagagaag cctcggctga tgattaatta aattgatctt tcggctaccc gagagaatta   7020
catttccaag agacttcttc accaaaatcc agatgggttt acataaactt ctgcccatgg   7080
gtatctcctc tctcctaaca cgctgtgacg tctgggcttg gtggaatctc agggaagcat   7140
ccgtggggtg gaaggtcatc gtctggctcg ttgtttgatg gttatattac catgcaattt   7200
tctttgccta catttgtatt gaatacatcc caatctcctt cctatttcggt gacatgacac   7260 attctatttc agaaggcttt gatttatca agcactttca tttacttctc atggcagtgc    7320
ctattacttc tcttacaata cccatctgtc tgcttacca aaatctattt cccttttca     7380 gatcctccca aatggtcctc ataaactgtc ctgcctccac ctagtggtcc aggtatattt   7440
ccacaatgtt acatcaacag gcacttctag ccatttttcct tctcaaaagg tgcaaaagc   7500 aacttcataa acacaaatta aatcttcggt gaggtagtgt gatgctgctt cctcccaact   7560
cagcgcactt cgtcttcctc attccacaaa aacccatagc cttccttcac tctgcaggac   7620
```

```
tagtgctgcc aagggttcag ctctacctac tggtgtgctc ttttgagcaa gttgcttagc   7680
ctctctgtaa cacaaggaca atagctgcaa gcatcccaa agatcattgc aggagacaat    7740
gactaaggct accagagccg caataaaagt cagtgaattt tagcgtggtc ctctctgtct   7800
ctccagaacg gctgccacgt ggaattgctc ttcctccgct acatctcgga ctgggaccta   7860
gaccctggcc gctgctaccg cgtcacctgg ttcacctcct ggagccctg ctacgactgt    7920 gcccgacatg tggccgactt tctgcgaggg aaccccaacc tcagtctgag gatcttcacc   7980
gcgcgcctct acttctgtga ggaccgcaag gctgagcccg aggggctgcg gcggctgcac   8040
cgcgccgggg tgcaaatagc catcatgacc ttcaaaggtg cgaaagggcc ttccgcgcag   8100
gcgcagtgca gcagcccgca ttcgggattg cgatgcggaa tgaatgagtt agtggggaag   8160 ctcgaggga agaagtgggc ggggattctg gttcacctct ggagccgaaa ttaaagatta    8220
gaagcagaga aaagagtgaa tggctcagag acaaggcccc gaggaaatga gaaaatgggg   8280
ccagggttgc ttctttcccc tcgatttgga acctgaactg tcttctaccc ccatatcccc   8340
gccttttttt cctttttttt tttttgaag attatttta ctgctggaat acttttgtag      8400
aaaaccacga aagaactttc aaagcctggg aagggctgca tgaaaattca gttcgtctct   8460
ccagacagct tcggcgcatc cttttggtaa ggggcttcct cgcttttta attttcttc      8520 tttctctaca gtcttttttg gagtttcgta tatttcttat attttcttat tgttcaatca   8580
ctctcagttt tcatctgatg aaactttat ttctcctcca catcagcttt ttcttctgct    8640
gtttcaccat tcagagccct ctgctaaggt tccttttcc tcccttttct ttctttgtt     8700 gtttcacatc tttaaatttc tgtctctccc cagggttgcg tttccttcct ggtcagaatt   8760
cttttctcct tttttttttt tttttttttt tttttaaac aaacaaacaa aaacccaaa     8820 aaaactcttt cccaatttac tttcttccaa catgttacaa agccatccac tcagtttaga   8880
agactctccg gccccaccga cccccaacct cgttttgaag ccattcactc aatttgcttc   8940
tctctttctc tacagcccct gtatgaggtt gatgacttac gagacgcatt tcgtactttg   9000
ggactttgat agcaacttcc aggaatgtca cacacgatga aatatctctg ctgaagacag   9060
tggataaaaa acagtccttc aagtcttctc tgtttttatt cttcaactct cactttctta   9120
gagtttacag aaaaaatatt tatatacgac tcttaaaaa gatctatgtc ttgaaaatag    9180
agaaggaaca caggtctggc cagggacgtg ctgcaattgg tgcagttttg aatgcaacat   9240
tgtcccctac tgggaataac agaactgcag gacctgggag catcctaaag tgtcaacgtt   9300
tttctatgac ttttaggtag gatgagagca gaaggtagat cctaaaaagc atggtgagag   9360
gatcaaatgt ttttatatca acatccttta ttatttgatt catttgagtt aacagtggtg   9420
ttagtgatag attttctat tcttttccct tgacgtttac tttcaagtaa cacaaactct    9480
tccatcaggc catgatctat aggacctcct aatgagagta tctgggtgat tgtgacccca   9540
aaccatctct ccaaagcatt aatatccaat catgcgctgt atgttttaat cagcagaagc   9600 atgttttat gtttgtacaa aagaagattg ttatgggtgg ggatgaggt atagaccatg     9660 catggtcacc ttcaagctac tttaataaag gatcttaaaa tgggcaggag gactgtgaac   9720
aagcacccct aataatgggt tgatgtctga agtagcaaat cttctggaaa cgcaaactct   9780
tttaaggaag tccctaattt agaaacaccc acaaacttca catatcataa ttagcaaaca   9840
attggaagga agttgcttga atgttgggga gaggaaaatc tattggctct cgtgggtctc   9900
ttcatctcag aaatgccaat caggtcaagg tttgctacat tttgtatgtg tgtgatgctt   9960
```

-continued

```
ctcccaaagg tatattaact ataaagaga gttgtgacaa acagaatga taaagctgcg     10020 aaccgtggca cacgctcata gttctagctg cttgggaggt tgaggaggga ggatggcttg    10080
aacacaggtg ttcaaggcca gcctgggcaa cataacaaga tcctgtctct caaaaaaaaa    10140
aaaaaaaaaa agaaagagag agggccgggc gtggtggctc acgcctgtaa tcccagcact    10200
ttgggaggcc gagccggcg gatcacctgt ggtcaggagt ttgagaccag cctggccaac     10260
atggcaaaac cccgtctgta ctcaaaatgc aaaaattagc caggcgtggt agcaggcacc    10320
tgtaatccca gctacttggg aggctgaggc aggagaatcg cttgaaccca ggaggtggag    10380
gttgcagtaa gctgagatcg tgccgttgca ctccagcctg ggcgacaaga gcaagactct    10440
gtctcagaaa aaaaaaaaa aagagagag agagagaaag agaacaatat tgggagaga      10500 aggatgggga agcattgcaa ggaaattgtg ctttatccaa caaatgtaa ggagccaata     10560 agggatccct atttgtctct tttggtgtct atttgtccct aacaactgtc tttgacagtg    10620
agaaaaatat tcagaataac catatccctg tgccgttatt acctagcaac ccttgcaatg    10680
aagatgagca gatccacagg aaaacttgaa tgcacaactg tcttatttta atcttattgt    10740
acataagttt gtaaaagagt taaaaattgt tacttcatgt attcatttat attttatatt    10800
attttgcgtc taatgatttt ttattaacat gatttccttt tctgatatat tgaaatggag    10860
tctcaaagct tcataaattt ataactttag aaatgattct aataacaacg tatgtaattg    10920
taacattgca gtaatggtgc tacgaagcca tttctcttga tttttagtaa acttttatga    10980
cagcaaattt gcttctggct cactttcaat cagttaaata aatgataaat aattttggaa    11040
gctgtgaaga taaaataacca aataaaataa tataaaagtg atttatatga agttaaaata   11100
aaaaatcagt atgatggaat aaacttgaga gtccagaagt tatcccatac atctgtaatc   11160
aactaatttc tcacaagggt gtaaggacca ttcaatggag aaaa                    11204
```

<210> SEQ ID NO 36
<211> LENGTH: 229
<212> TYPE: PRT
<213> ORGANISM: Mus musculus

<400> SEQUENCE: 36

```
Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Val Trp Arg His Thr Ser Gln Asn Thr Ser Asn His Val Glu Val
    50                  55                  60

Asn Phe Leu Glu Lys Phe Thr Thr Glu Arg Tyr Phe Arg Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg His Pro Tyr Val Thr Leu
            100                 105                 110

Phe Ile Tyr Ile Ala Arg Leu Tyr His His Thr Asp Gln Arg Asn Arg
        115                 120                 125

Gln Gly Leu Arg Asp Leu Ile Ser Ser Gly Val Thr Ile Gln Ile Met
    130                 135                 140

Thr Glu Gln Glu Tyr Cys Tyr Cys Trp Arg Asn Phe Val Asn Tyr Pro
145                 150                 155                 160
```

-continued

```
Pro Ser Asn Glu Ala Tyr Trp Pro Arg Tyr Pro His Leu Trp Val Lys
                165                 170                 175

Leu Tyr Val Leu Glu Leu Tyr Cys Ile Ile Leu Gly Leu Pro Pro Cys
            180                 185                 190

Leu Lys Ile Leu Arg Arg Lys Gln Pro Gln Leu Thr Phe Phe Thr Ile
        195                 200                 205

Thr Leu Gln Thr Cys His Tyr Gln Arg Ile Pro Pro His Leu Leu Trp
    210                 215                 220

Ala Thr Gly Leu Lys
225
```